US008481031B2

(12) United States Patent
Glass et al.

(10) Patent No.: US 8,481,031 B2
(45) Date of Patent: Jul. 9, 2013

(54) METHODS AND COMPOSITIONS USING KLOTHO-FGF FUSION POLYPEPTIDES

(75) Inventors: David Glass, Cortlandt Manor, NY (US); Shou-Ih Hu, New Providence, NJ (US)

(73) Assignee: Novartis AG, Basel (CH)

( * ) Notice: Subject to any disclaimer, the term of this patent is extended or adjusted under 35 U.S.C. 154(b) by 269 days.

(21) Appl. No.: 12/360,970

(22) Filed: Jan. 28, 2009

(65) Prior Publication Data

US 2009/0192087 A1 Jul. 30, 2009

Related U.S. Application Data

(60) Provisional application No. 61/063,015, filed on Jan. 28, 2008.

(51) Int. Cl.
  *A61K 38/18* (2006.01)
  *A61K 39/395* (2006.01)
  *C07K 14/50* (2006.01)
  *C07K 16/00* (2006.01)
  *C12N 1/21* (2006.01)
  *C12N 5/10* (2006.01)
  *C12N 15/21* (2006.01)
  *C12N 15/63* (2006.01)

(52) U.S. Cl.
  USPC ............... 424/134.1; 435/320.1; 435/243; 435/325; 435/69.7; 514/9.1; 514/21.2; 530/399

(58) Field of Classification Search
  None
  See application file for complete search history.

(56) References Cited

U.S. PATENT DOCUMENTS

| | | | |
|---|---|---|---|
| 5,408,038 A * | 4/1995 | Smith et al. ............... | 530/359 |
| 5,541,094 A | 7/1996 | Anton et al. | |
| 7,060,479 B2 | 6/2006 | Dumas Milne Edwards et al. | |
| 7,217,798 B2 | 5/2007 | Hinton et al. | |
| 7,223,563 B2 | 5/2007 | Econs et al. | |
| 7,259,248 B2 | 8/2007 | Itoh et al. | |
| 7,745,406 B2 | 6/2010 | Econs et al. | |
| 2006/0160181 A1* | 7/2006 | Luethy et al. ............... | 435/69.1 |

OTHER PUBLICATIONS

Carpenter et al. J. Clin. Endocrinol. Metab. 95: E352-E357, 2010.*
Kuro-o. Pediatr. Nephrol. 25: 583-590, 2010.*
Drueke et al. Nephrol Dial. Transplant. 22: 1524-1526, 2007.*
Kurosu et al., "Regulation of Fibroblast Growth Factor-23 Signaling by Klotho", Journal of Biological Chemistry, 2006 vol. 281 No. 10 pp. 6120-6123.
Tohyama et al., "Klotho is a Novel beta-Glucoronidase Capable of Hydrolyzing Steroid beta-Glucuronides", Journal of Biological Chemistry, 2004 vol. 279 No. 11 pp. 9777-9784.
Torres et al., "Klotho: An antiaging protein involved in mineral and vitamin D metabolism". Kidney International, 2007 vol. 71 No. 8 pp. 730-737.
Wu et al., "Co-receptor Requirements for Fibroblast Growth Factor-19 Signaling", Journal of Biological Chemistry, 2007 vol. 282 No. 40 pp. 29069-29072.
Razzaue et al., "Therapeutic potential of Klotho—FGF23 fusion polypeptides: WO200909532". Expert Opin. Ther. Patents, 2010 vol. 20 No. 6 pp. 1-5.
Goetz et al, "Molecular Insights into the Klotho-Dependent, Endocrine Mode of Action of Fibroblast Growth Factor 19 Subfamily Members", Mol. and Cell. Bio.; May 2007; 3417.
Hessell et al, "Fc receptor but not complement binding is important in antibody protection against HIV" Nature (2007); vol. 449 p. 101.
Lode et al, "Gene therapy with a single chain interleukin 12 fusion protein induces T cell-dependent protective immunity in a syngeneic model of murine neuroblastoma"; Proc. Nat. Acad. Sci. USA (1998) vol. 95 p. 2475.
Ray, L. Bryan; "Klotho Gets Around"; Sci. STKE (2006) vol. 2006(365) p. tw416.
Urakawa, et al; "Klotho converts canonical FGF receptor into a specific receptor for FGF23"; Nature (2006) vol. 444, p. 770.
The ADHR Consortium; "Autosomal dominant hypophosphataemic rickets is associated with mutations in FGF23"; Nature Genetics; 26:345-348 (2000).
Bai et al.; "The Autosomal Dominant Hypophosphatemic Rickets R176Q Mutation in Fibroblast Growth Factor 23 Resists Proteolytic Cleavage and Enhances in Vivo Biological Potency"; The Journal of Biological Chemistry; 278(11):9843-9849 (2003).
Bai et al.; "Transgenic Mice Overexpressing Human Fibroblast Growth Factor 23 (R176Q) Delineate a Putative Role for Parathyroid Hormone in Renal Phosphate Wasting Disorders"; Endocrinology; 145(11):5269-5279 (2004).
Bai et al.; "Klotho ablation converts the biochemical and skeletal alterations in FGF23 (R176Q) transgenic mice to a Klotho-deficient phenotype"; Am. J. Physiol. Endocrinol. Metab.; 296:E79-E88 (2009).
Ben-Dov et al.; "The parathyroid is a target organ for FGF23 in rats"; The Journal of Clinical Investigation—Research Article; 117(12):4003-4008 (2007).
Berndt et al.; "Biological activity of FGF-23 fragments"; Pflugers Arch—Eur. J. Physiol.; 454:615-623 (2007).
Shimada et al.; "Mutant FGF-23 responsible for autosomal dominant hypophosphatemic rickets is resistant to proteolytic cleavage and causes hypophosphatemia in vivo"; Endocrinology; 143(8):3179-3182 (2002).
Strewler; "FGF23, hypophosphatemia, and rickets: Has phosphatonin been found?"; PNAS—Commentary; 98 (11):5945-5946 (2001).
Urakawa et al; "Klotho converts canonical FGF receptor into a specific receptor for FGF23"; Nature; 444:770-774 (2006)[Supplemental Data List; Supplemental Figures 1-6; Supplemental Discussion; Supplemental Methods and Supplemental Table].
White et al.; "Autosomal-dominant hypophosphatemic rickets (ADHR) mutations stabilize FGF-23"; Kidney International; 60:2079-2086 (2001).
Yu et al.; "FGF23 and disorders of phosphate homeostasis"; Cytokine & Growth Factor Reviews; 16:221-232 (2005).
Ito et al.; "Molecular cloning and expression analyses of mouse bklotho, which encodes a novel Klotho family protein"; Mech. Dev.; 98:115-119 (2000).
Wu et al.; "C-terminal Tail of FGF19 Determines Its Specificity toward Klotho Co-receptors"; J. Biol. Chem.; 283 (48):33304-33309 (2008).

* cited by examiner

*Primary Examiner* — Christine J Saoud

(74) *Attorney, Agent, or Firm* — Frank Wu

(57) ABSTRACT

The present invention is directed to fusion polypeptides comprising Klotho protein or an active fragment thereof and FGF23 or an active fragment thereof.

21 Claims, 8 Drawing Sheets

Figure 1:
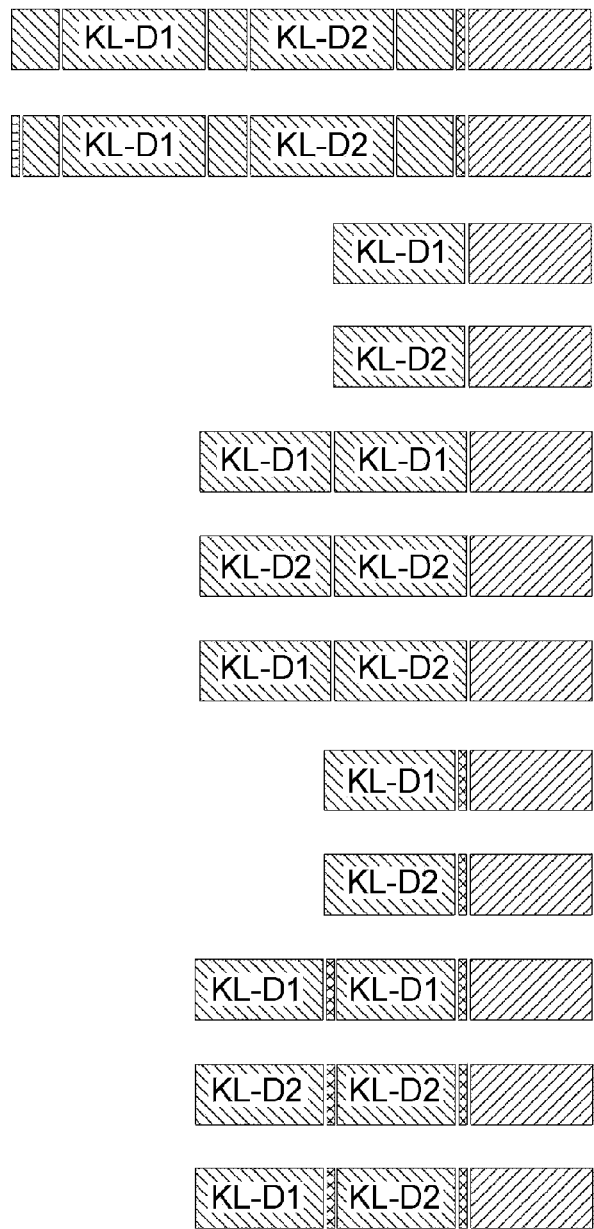
Figure 1:
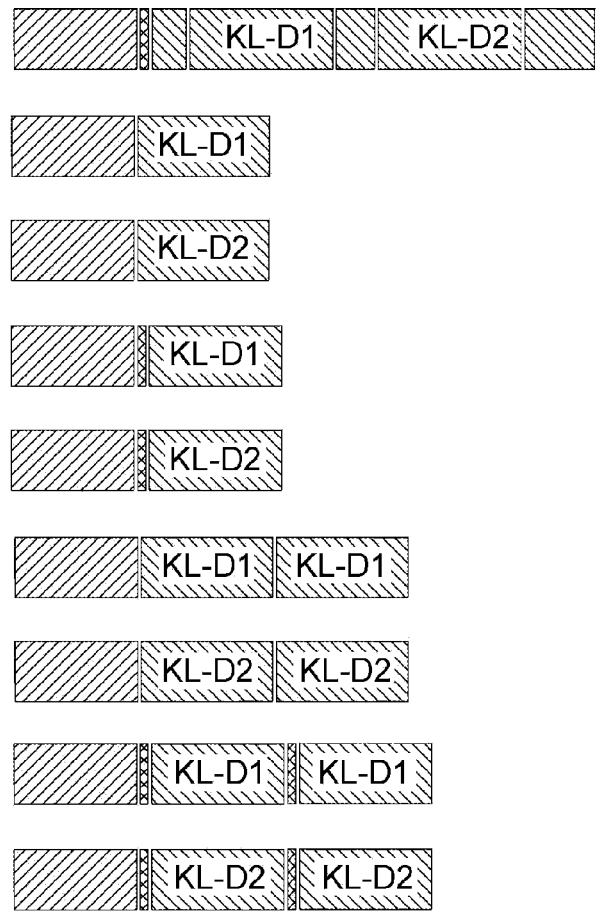

▨ : Klotho (extracellular domain) or active fragment of Klotho;

▨ : FGF23 (R179Q), FGF23, FGF 19, FGF21; ▨: linker; ▋: IgG signal peptide.

lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis;
lane 2, molecular weight marker

SEQUENCE LISTING

<160> NUMBER OF SEQ ID NOS: 45

<210> SEQ ID NO 1
<211> LENGTH: 5003
<212> TYPE: DNA
<213> ORGANISM: Homo Sapiens

<400> SEQUENCE: 1

| | | | | | | |
|---|---|---|---|---|---|---|
| cgcgcagcat | gcccgccagc | gccccgccgc | gccgcccgcg | gccgccgccg | ccgtcgctgt | 60 |
| cgctgctgct | ggtgctgctg | ggcctgggcg | ccgccgcct | gcgtgcggag | ccgggcgacg | 120 |
| gcgcgcagac | ctgggcccgt | tctcgcggc | ctcctgcccc | cgaggccgcg | ggcctcttcc | 180 |
| agggcacctt | ccccgacggc | ttcctctggg | ccgtgggcag | cgccgcctac | cagaccgagg | 240 |
| gcggctggca | gcagcacggc | aagggtgcgt | ccatctggga | tacgttcacc | caccaccccc | 300 |
| tggcaccccc | gggagactcc | cggaacgcca | gtctgccgtt | gggcgccccg | tcgccgctgc | 360 |
| agcccgccac | cggggacgta | gccagcgaca | gctacaacaa | cgtcttccgc | gacacggagg | 420 |
| cgctgcgcga | gctcggggtc | actcactacc | gcttctccat | ctcgtgggcg | cgagtgctcc | 480 |
| ccaatggcag | cgcgggcgtc | cccaaccgcg | aggggctgcg | ctactaccgg | cgcctgctgg | 540 |
| agcggctgcg | ggagctgggc | gtgcagcccg | tggtcaccct | gtaccactgg | gacctgcccc | 600 |
| agcgcctgca | ggacgcctac | ggcggctggg | ccaaccgcgc | cctggccgac | cacttcaggg | 660 |
| attacgcgga | gctctgcttc | cgccacttcg | gcggtcaggt | caagtactgg | atcaccatcg | 720 |
| acaaccccta | cgtggtggcc | tggcacggct | acgccaccgg | gcgcctggcc | cccggcatcc | 780 |
| ggggcagccc | gcggctcggg | tacctggtgg | cgcacaacct | cctcctggct | catgccaaag | 840 |
| tctggcatct | ctacaatact | tctttccgtc | ccactcaggg | aggtcaggtg | tccattgccc | 900 |
| taagctctca | ctggatcaat | cctcgaagaa | tgaccgacca | cagcatcaaa | gaatgtcaaa | 960 |
| aatctctgga | ctttgtacta | ggttggtttg | ccaaacccgt | atttattgat | ggtgactatc | 1020 |
| ccgagagcat | gaagaataac | ctttcatcta | ttctgcctga | ttttactgaa | tctgagaaaa | 1080 |
| agttcatcaa | aggaactgct | gacttttttg | ctctttgctt | tggacccacc | ttgagttttc | 1140 |
| aacttttgga | ccctcacatg | aagttccgcc | aattggaatc | tcccaacctg | aggcaactgc | 1200 |
| tttcctggat | tgaccttgaa | tttaaccatc | ctcaaatatt | tattgtgaa | aatggctggt | 1260 |
| ttgtctcagg | gaccaccaag | agagatgatg | ccaaatatat | gtattacctc | aaaaagttca | 1320 |
| tcatggaaac | cttaaaagcc | atcaagctgg | atggggtgga | tgtcatcggg | tataccgcat | 1380 |
| ggtccctcat | ggatggtttc | gagtggcaca | gaggttacag | catcaggcgt | ggactcttct | 1440 |
| atgttgactt | tctaagccag | gacaagatgt | tgttgccaaa | gtcttcagcc | ttgttctacc | 1500 |
| aaaagctgat | agagaaaaat | ggcttccctc | ctttacctga | aaatcagccc | ctagaaggga | 1560 |
| catttccctg | tgactttgct | tggggagttg | ttgacaacta | cattcaagta | gataccactc | 1620 |
| tgtctcagtt | taccgacctg | aatgtttacc | tgtgggatgt | ccaccacagt | aaaaggctta | 1680 |
| ttaaagtgga | tgggggttgtg | accaagaaga | ggaaatccta | ctgtgttgac | tttgctgcca | 1740 |
| tccagcccca | gatcgcttta | ctccaggaaa | tgcacgttac | acattttcgc | ttctcccctgg | 1800 |
| actgggccct | gattctccct | ctgggtaacc | agtcccaggt | gaaccacacc | atcctgcagt | 1860 |
| actatcgctg | catggccagc | gagcttgtcc | gtgtcaacat | caccccagtg | gtggccctgt | 1920 |
| ggcagcctat | ggccccgaac | caaggactgc | cgcgcctcct | ggccaggcag | ggcgcctggg | 1980 |
| agaaccccta | cactgccctg | gcctttgcag | agtatgcccg | actgtgcttt | caagagctcg | 2040 |

```
gccatcacgt caagctttgg ataacgatga atgagccgta tacaaggaat atgacataca    2100
gtgctggcca caaccttctg aaggcccatg ccctggcttg gcatgtgtac aatgaaaagt    2160
ttaggcatgc tcagaatggg aaaatatcca tagccttgca ggctgattgg atagaacctg    2220
cctgcccttt ctcccaaaag gacaaagagg tggccgagag agttttggaa tttgacattg    2280
gctggctggc tgagcccatt ttcggctctg gagattatcc atgggtgatg agggactggc    2340
tgaaccaaag aaacaatttt cttcttcctt atttcactga gatgaaaaa aagctaatcc    2400 agggtacctt tgacttttg gctttaagcc attataccac catccttgta gactcagaaa    2460
aagaagatcc aataaaatac aatgattacc tagaagtgca agaaatgacc gacatcacgt    2520
ggctcaactc ccccagtcag gtggcggtag tgccctgggg gttgcgcaaa gtgctgaact    2580
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt ttttttcaca    2940
cccgaaagtc tttactggct ttcatagctt ttctattttt tgcttctatt atttctctct    3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg ggcataggtg atcgtaaaat attgaataat gcgaatagtg    3240
cctgaatttg ttctcttttt gggtgattaa aaaactgaca ggcactataa tttctgtaac    3300
acactaacaa aagcatgaaa aataggaacc acaccaatgc aacatttgtg cagaaatttg    3360
aatgacaaga ttaggaatat tttcttctgc acccacttct aaatttaatg ttttttctgga   3420 agtagtaatt gcaagagttc gaatagaaag ttatgtacca agtaaccatt tctcagctgc    3480
cataataatg cctagtggct tcccctctgt caaatctagt ttcctatgga aaagaagatg    3540
gcagatacag gagagacgac agagggtcct aggctggaat gttccttcg aaagcaatgc    3600 ttctatcaaa tactagtatt aatttatgta tctggttaat gacatacttg gagagcaaat    3660
tatggaaatg tgtattttat atgatttttg aggtcctgtc taaaccctgt gtccctgagg    3720
gatctgtctc actggcatct tgttgaggc cttgcacata ggaaacttt gataagtatc     3780 tgcggaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccatttttga gcagatcttg gaatgaatga    3960
catgaccttt ccctagagaa taaggatgaa ataatcactc attctatgaa cagtgacact    4020
actttctatt ctttagctgt actgtaattt ctttgagttg atagttttac aaattcttaa    4080
taggttcaaa agcaatctgg tctgaataac actggatttg tttctgtgat ctctgaggtc    4140
tattttatgt ttttgctgct acttctgtgg aagtagcttt gaactagttt tactttgaac    4200
tttcacgctg aaacatgcta gtgatatcta gaaagggcta attaggtctc atcctttaat    4260
gccccttaaa taagtcttgc tgattttcag acagggaagt ctctctatta cactggagct    4320
gttttataga taagtcaata ttgtatcagg caagataaac caatgtcata acaggcattg    4380
ccaacctcac tgacacaggg tcatagtgta taataatata ctgtactata taatatatca    4440
```

```
tctttagagg tatgattttt tcatgaaaga taagcttttg gtaatattca ttttaaagtg      4500
gacttattaa aattggatgc tagagaatca agtttatttt atgtatatat ttttctgatt      4560
ataagagtaa tatatgttca ttgtaaaaat ttttaaaaca cagaaactat atgcaaagaa      4620
aaaataaaaa ttatctataa tctcagaacc cagaaatagc cactattaac atttcctacg      4680
tattttattt tacatagatc atattgtata tagttagtat ctttattaat ttttattatg      4740
aaactttcct ttgtcattat tagtcttcaa aagcatgatt tttaatagtt gttgagtatt      4800
ccaccacagg aatgtatcac aacttaaccg ttcccgtttg ttagactagt ttcttattaa      4860
tgttgatgaa tgttgtttaa aaataatttt gttgctacat ttactttaat ttccttgact      4920
gtaaagagaa gtaattttgc tccttgataa agtattatat taataataaa tctgcctgca      4980 acttttttgcc ttctttcata atc                                            5003
```

<210> SEQ ID NO 2
<211> LENGTH: 1012
<212> TYPE: PRT
<213> ORGANISM: Homo Sapiens

<400> SEQUENCE: 2

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
```

```
                275                 280                 285
Thr Gln Gly Gly Gln Val Ser Ile Ala Leu Ser Ser His Trp Ile Asn
290                 295                 300

Pro Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
                370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
                450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
                610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
                690                 695                 700
```

-continued

| | | | | | | | | | | | | | | | |
|---|---|---|---|---|---|---|---|---|---|---|---|---|---|---|---|
|Lys|Ala|His|Ala|Leu|Ala|Trp|His|Val|Tyr|Asn|Glu|Lys|Phe|Arg|His|
|705| | | |710| | | |715| | | |720| | | |

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
        740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 3
<211> LENGTH: 3279
<212> TYPE: DNA
<213> ORGANISM: Homo Sapiens

<400> SEQUENCE: 3
atcctcagtc tcccagttca agctaatcat tgacagagct ttacaatcac aagcttttac      60
tgaagctttg ataagacagt ccagcagttg gtggcaaatg aagccaggct gtgcggcagg     120
atctccaggg aatgaatgga ttttcttcag cactgtgaa ataaccacac gctataggaa      180
tacaatgtcc aacgggggat tgcaaagatc tgtcatcctg tcagcactta ttctgctacg     240
agctgttact ggattctctg gagatggaag agctatatgg tctaaaaatc ctaattttac    300
tccggtaaat gaaagtcagc tgtttctcta tgacactttc cctaaaaact ttttctgggg    360

```
tattgggact ggagcattgc aagtggaagg gagttggaag aaggatggaa aaggaccttc    420
tatatgggat catttcatcc acacacacct taaaaatgtc agcagcacga atggttccag    480
tgacagttat attttcctgg aaaaagactt atcagccctg gattttatag gagtttcttt   540
ttatcaattt tcaatttcct ggccaaggct tttccccgat ggaatagtaa cagttgccaa   600
cgcaaaaggt ctgcagtact acagtactct tctggacgct ctagtgctta gaaacattga   660
acctatagtt actttatacc actgggattt gcctttggca ctacaagaaa atatggggg    720 gtggaaaaat gataccataa tagatatctt caatgactat gccacatact gtttccagat    780
gtttggggac cgtgtcaaat attggattac aattcacaac ccatatctag tggcttggca    840
tgggtatggg acaggtatgc atgcccctgg agagaaggga aatttagcag ctgtctacac    900
tgtgggacac aacttgatca aggctcactc gaaagtttgg cataactaca acacacattt    960
ccgcccacat cagaagggtt ggttatcgat cacgttggga tctcattgga tcgagccaaa   1020
ccggtcggaa aacacgatgg atatattcaa atgtcaacaa tccatggttt ctgtgcttgg   1080
atggtttgcc aaccctatcc atggggatgg cgactatcca gaggggatga gaaagaagtt   1140
gttctccgtt ctacccattt tctctgaagc agagaagcat gagatgagag gcacagctga   1200
tttctttgcc ttttcttttg gacccaacaa cttcaagccc ctaaacacca tggctaaaat   1260
gggacaaaat gtttcactta atttaagaga agcgctgaac tggattaaac tggaatacaa   1320
caaccctcga atcttgattg ctgagaatgg ctggttcaca gacagtcgtg tgaaaacaga   1380
agacaccacg gccatctaca tgatgaagaa ttttcctcagc caggtgcttc aagcaataag   1440
gttagatgaa atacgagtgt ttggttatac tgcctggtct ctcctggatg gctttgaatg   1500
gcaggatgct tacaccatcc gccgaggatt attttatgtg gatttttaaca gtaaacagaa   1560 agagcggaaa cctaagtctt cagcacacta ctacaaacag atcatacgag aaaatggttt   1620
ttctttaaaa gagtccacgc cagatgtgca gggccagttt ccctgtgact ctcctgggg    1680 tgtcactgaa tctgttctta gcccgagtc tgtggcttcg tccccacagt tcagcgatcc    1740
tcatctgtac gtgtggaacg ccactggcaa cagactgttg caccgagtgg aagggtgag    1800 gctgaaaaca cgacccgctc aatgcacaga ttttgtaaac atcaaaaaac aacttgagat   1860
gttggcaaga atgaaagtca cccactaccg gtttgctctg gattgggcct cggtccttcc   1920
cactggcaac ctgtccgcgg tgaaccgaca ggccctgagg tactacaggt gcgtggtcag   1980 tgagggggctg aagcttggca ctctccgcgat ggtcacccctg tattatccga cccacgccca   2040
cctaggcctc cccgagcctc tgttgcatgc cgacgggtgg ctgaacccat cgacggccga   2100
ggccttccag gcctacgctg ggctgtgctt ccaggagctg ggggacctgg tgaagctctg   2160
gatcaccatc aacgagccta accggctaag tgacatctac aaccgctctg caacgacac    2220 ctacggggcg gcgcacaacc tgctggtggc ccacgccctg gcctggcgcc tctacgaccg   2280
gcagttcagg ccctcacagc gcgggggccgt gtcgctgtcg ctgcacgcgg actgggcgga   2340
acccgccaac ccctatgctg actcgcactg gaggcggcc gagcgcttcc tgcagttcga   2400
gatcgcctgg ttcgccgagc cgctcttcaa accggggac taccccgcgg ccatgaggga   2460
atacattgcc tccaagcacc gacgggggct ttccagctcg ccctgccgc gcctcaccga   2520 ggccgaaagg aggctgctca agggcacggt cgacttctgc gcgctcaacc acttcaccac   2580
taggttcgtg atgcacgagc agctggccgg cagccgctac gactcggaca gggacatcca   2640
gtttctgcag gacatcaccc gcctgagctc ccccacgcgc ctggctgtga ttccctgggg   2700
ggtgcgcaag ctgctgcggt gggtccggag gaactacggc gacatggaca tttacatcac   2760
```

-continued

```
cgccagtggc atcgacgacc aggctctgga ggatgaccgg ctccggaagt actacctagg    2820
gaagtacctt caggaggtgc tgaaagcata cctgattgat aaagtcagaa tcaaaggcta    2880
ttatgcattc aaactggctg aagagaaatc taaacccaga tttggattct tcacatctga    2940
ttttaaagct aaatcctcaa tacaatttta caacaaagtg atcagcagca ggggcttccc    3000
ttttgagaac agtagttcta gatgcagtca gacccaagaa atacagagt gcactgtctg     3060 cttattcctt gtgcagaaga accactgat attcctgggt tgttgcttct tctccaccct    3120
ggttctactc ttatcaattg ccattttca aaggcagaag agaagaaagt tttggaaagc    3180
aaaaaactta caacacatac cattaaagaa aggcaagaga gttgttagct aaactgatct    3240
gtctgcatga tagacagttt aaaaattcat cccagttcc                           3279
```

<210> SEQ ID NO 4
<211> LENGTH: 1044
<212> TYPE: PRT
<213> ORGANISM: Homo Sapiens

<400> SEQUENCE: 4

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
        50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
                100                 105                 110

Phe Ile His Thr His Leu Lys Asn Val Ser Ser Thr Asn Gly Ser Ser
            115                 120                 125

Asp Ser Tyr Ile Phe Leu Glu Lys Asp Leu Ser Ala Leu Asp Phe Ile
        130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285
```

-continued

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
                340                 345                 350

Pro Ile Phe Ser Glu Ala Glu Lys His Glu Met Arg Gly Thr Ala Asp
                355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
                420                 425                 430

Ile Tyr Met Met Lys Asn Phe Leu Ser Gln Val Leu Gln Ala Ile Arg
                435                 440                 445

Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
                515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
                580                 585                 590

Lys Val Thr His Tyr Arg Phe Ala Leu Asp Trp Ala Ser Val Leu Pro
                595                 600                 605

Thr Gly Asn Leu Ser Ala Val Asn Arg Gln Ala Leu Arg Tyr Tyr Arg
                610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
                660                 665                 670

Tyr Ala Gly Leu Cys Phe Gln Glu Leu Gly Asp Leu Val Lys Leu Trp
                675                 680                 685

Ile Thr Ile Asn Glu Pro Asn Arg Leu Ser Asp Ile Tyr Asn Arg Ser
                690                 695                 700

Gly Asn Asp Thr Tyr Gly Ala Ala His Asn Leu Leu Val Ala His Ala
705                 710                 715                 720

```
Leu Ala Trp Arg Leu Tyr Asp Arg Gln Phe Arg Pro Ser Gln Arg Gly
            725                 730                 735

Ala Val Ser Leu Ser Leu His Ala Asp Trp Ala Glu Pro Ala Asn Pro
            740                 745                 750

Tyr Ala Asp Ser His Trp Arg Ala Glu Arg Phe Leu Gln Phe Glu
            755                 760                 765

Ile Ala Trp Phe Ala Glu Pro Leu Phe Lys Thr Gly Asp Tyr Pro Ala
            770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
            805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
            835                 840                 845

Phe Leu Gln Asp Ile Thr Arg Leu Ser Ser Pro Thr Arg Leu Ala Val
            850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
            885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
            930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
            965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
            995                 1000                1005

Val Leu Leu Leu Ser Ile Ala Ile Phe Gln Arg Gln Lys Arg Arg
            1010                1015                1020

Lys Phe Trp Lys Ala Lys Asn Leu Gln His Ile Pro Leu Lys Lys
            1025                1030                1035

Gly Lys Arg Val Val Ser
            1040
```

<210> SEQ ID NO 5
<211> LENGTH: 449
<212> TYPE: PRT
<213> ORGANISM: Homo Sapiens

<400> SEQUENCE: 5

```
Gln Gly Thr Phe Pro Asp Gly Phe Leu Trp Ala Val Gly Ser Ala Ala
1               5                   10                  15

Tyr Gln Thr Glu Gly Gly Trp Gln Gln His Gly Lys Gly Ala Ser Ile
            20                  25                  30

Trp Asp Thr Phe Thr His His Pro Leu Ala Pro Pro Gly Asp Ser Arg
        35                  40                  45
```

Asn Ala Ser Leu Pro Leu Gly Ala Pro Ser Pro Leu Gln Pro Ala Thr
    50                  55                  60

Gly Asp Val Ala Ser Asp Ser Tyr Asn Asn Val Phe Arg Asp Thr Glu
65                  70                  75                  80

Ala Leu Arg Glu Leu Gly Val Thr His Tyr Arg Phe Ser Ile Ser Trp
                85                  90                  95

Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
    130                 135                 140

Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
            180                 185                 190

Thr Gly Arg Leu Ala Pro Gly Ile Arg Gly Ser Pro Arg Leu Gly Tyr
        195                 200                 205

Leu Val Ala His Asn Leu Leu Leu Ala His Ala Lys Val Trp His Leu
    210                 215                 220

Tyr Asn Thr Ser Phe Arg Pro Thr Gln Gly Gly Gln Val Ser Ile Ala
225                 230                 235                 240

Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
            260                 265                 270

Pro Val Phe Ile Asp Gly Asp Tyr Pro Glu Ser Met Lys Asn Asn Leu
        275                 280                 285

Ser Ser Ile Leu Pro Asp Phe Thr Glu Ser Glu Lys Lys Phe Ile Lys
    290                 295                 300

Gly Thr Ala Asp Phe Phe Ala Leu Cys Phe Gly Pro Thr Leu Ser Phe
305                 310                 315                 320

Gln Leu Leu Asp Pro His Met Lys Phe Arg Gln Leu Glu Ser Pro Asn
                325                 330                 335

Leu Arg Gln Leu Leu Ser Trp Ile Asp Leu Glu Phe Asn His Pro Gln
        340                 345                 350

Ile Phe Ile Val Glu Asn Gly Trp Phe Val Ser Gly Thr Thr Lys Arg
    355                 360                 365

Asp Asp Ala Lys Tyr Met Tyr Tyr Leu Lys Lys Phe Ile Met Glu Thr
370                 375                 380

Leu Lys Ala Ile Lys Leu Asp Gly Val Asp Val Ile Gly Tyr Thr Ala
385                 390                 395                 400

Trp Ser Leu Met Asp Gly Phe Glu Trp His Arg Gly Tyr Ser Ile Arg
                405                 410                 415

Arg Gly Leu Phe Tyr Val Asp Phe Leu Ser Gln Asp Lys Met Leu Leu
            420                 425                 430

Pro Lys Ser Ser Ala Leu Phe Tyr Gln Lys Leu Ile Glu Lys Asn Gly
        435                 440                 445

Phe

<210> SEQ ID NO 6

<211> LENGTH: 437
<212> TYPE: PRT
<213> ORGANISM: Homo Sapiens

<400> SEQUENCE: 6

```
Gly Thr Phe Pro Cys Asp Phe Ala Trp Gly Val Val Asp Asn Tyr Ile
1               5                   10                  15

Gln Val Asp Thr Thr Leu Ser Gln Phe Thr Asp Leu Asn Val Tyr Leu
            20                  25                  30

Trp Asp Val His His Ser Lys Arg Leu Ile Lys Val Asp Gly Val Val
        35                  40                  45

Thr Lys Lys Arg Lys Ser Tyr Cys Val Asp Phe Ala Ala Ile Gln Pro
50                  55                  60

Gln Ile Ala Leu Leu Gln Glu Met His Val Thr His Phe Arg Phe Ser
65                  70                  75                  80

Leu Asp Trp Ala Leu Ile Leu Pro Leu Gly Asn Gln Ser Gln Val Asn
                85                  90                  95

His Thr Ile Leu Gln Tyr Tyr Arg Cys Met Ala Ser Glu Leu Val Arg
            100                 105                 110

Val Asn Ile Thr Pro Val Val Ala Leu Trp Gln Pro Met Ala Pro Asn
        115                 120                 125

Gln Gly Leu Pro Arg Leu Leu Ala Arg Gln Gly Ala Trp Glu Asn Pro
130                 135                 140

Tyr Thr Ala Leu Ala Phe Ala Glu Tyr Ala Arg Leu Cys Phe Gln Glu
145                 150                 155                 160

Leu Gly His His Val Lys Leu Trp Ile Thr Met Asn Glu Pro Tyr Thr
                165                 170                 175

Arg Asn Met Thr Tyr Ser Ala Gly His Asn Leu Leu Lys Ala His Ala
            180                 185                 190

Leu Ala Trp His Val Tyr Asn Glu Lys Phe Arg His Ala Gln Asn Gly
        195                 200                 205

Lys Ile Ser Ile Ala Leu Gln Ala Asp Trp Ile Glu Pro Ala Cys Pro
210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
                245                 250                 255

Val Met Arg Asp Trp Leu Asn Gln Arg Asn Asn Phe Leu Leu Pro Tyr
            260                 265                 270

Phe Thr Glu Asp Glu Lys Lys Leu Ile Gln Gly Thr Phe Asp Phe Leu
        275                 280                 285

Ala Leu Ser His Tyr Thr Thr Ile Leu Val Asp Ser Glu Lys Glu Asp
290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Pro Trp Gly Leu
                325                 330                 335

Arg Lys Val Leu Asn Trp Leu Lys Phe Lys Tyr Gly Asp Leu Pro Met
            340                 345                 350

Tyr Ile Ile Ser Asn Gly Ile Asp Asp Gly Leu His Ala Glu Asp Asp
        355                 360                 365

Gln Leu Arg Val Tyr Tyr Met Gln Asn Tyr Ile Asn Glu Ala Leu Lys
370                 375                 380

Ala His Ile Leu Asp Gly Ile Asn Leu Cys Gly Tyr Phe Ala Tyr Ser
385                 390                 395                 400
```

```
Phe Asn Asp Arg Thr Ala Pro Arg Phe Gly Leu Tyr Arg Tyr Ala Ala
                405                 410                 415

Asp Gln Phe Glu Pro Lys Ala Ser Met Lys His Tyr Arg Lys Ile Ile
            420                 425                 430

Asp Ser Asn Gly Phe
        435

<210> SEQ ID NO 7
<211> LENGTH: 949
<212> TYPE: PRT
<213> ORGANISM: Homo Sapiens

<400> SEQUENCE: 7

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335
```

```
Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Glu Asn Gly Trp
        370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
```

```
                    755                 760                 765
Asp Phe Leu Ala Leu Ser His Tyr Thr Thr Ile Leu Val Asp Ser Glu
            770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
        850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
            915                 920                 925

Phe Cys Pro Glu Glu Phe Thr Val Cys Thr Glu Cys Ser Phe Phe His
        930                 935                 940

Thr Arg Lys Ser Leu
945

<210> SEQ ID NO 8
<211> LENGTH: 33
<212> TYPE: PRT
<213> ORGANISM: Homo Sapiens

<400> SEQUENCE: 8

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala

<210> SEQ ID NO 9
<211> LENGTH: 25
<212> TYPE: PRT
<213> ORGANISM: Homo Sapiens

<400> SEQUENCE: 9

Met Ser Val Leu Thr Gln Val Leu Ala Leu Leu Leu Leu Trp Leu Thr
1               5                   10                  15

Gly Thr Arg Cys Arg Arg Leu Arg Ala
            20                  25

<210> SEQ ID NO 10
<211> LENGTH: 45
<212> TYPE: DNA
<213> ORGANISM: Homo Sapiens

<400> SEQUENCE: 10
ggaggtggag gttcaggagg tggaggttca ggaggtggag gttca              45

<210> SEQ ID NO 11
```

```
<211> LENGTH: 15
<212> TYPE: PRT
<213> ORGANISM: Homo Sapiens

<400> SEQUENCE: 11

Gly Gly Gly Gly Ser Gly Gly Gly Ser Gly Gly Gly Gly Ser
1               5                   10                  15

<210> SEQ ID NO 12
<211> LENGTH: 5
<212> TYPE: PRT
<213> ORGANISM: Homo Sapiens

<400> SEQUENCE: 12

Gly Gly Gly Gly Ser
1               5

<210> SEQ ID NO 13
<211> LENGTH: 1
<212> TYPE: PRT
<213> ORGANISM: Homo Sapiens

<400> SEQUENCE: 13

Gly
1

<210> SEQ ID NO 14
<211> LENGTH: 2
<212> TYPE: PRT
<213> ORGANISM: Homo Sapiens

<400> SEQUENCE: 14

Gly Gly
1

<210> SEQ ID NO 15
<211> LENGTH: 2
<212> TYPE: PRT
<213> ORGANISM: Homo Sapiens

<400> SEQUENCE: 15

Gly Ser
1

<210> SEQ ID NO 16
<211> LENGTH: 3
<212> TYPE: PRT
<213> ORGANISM: Homo Sapiens

<400> SEQUENCE: 16

Gly Gly Ser
1

<210> SEQ ID NO 17
<211> LENGTH: 1
<212> TYPE: PRT
<213> ORGANISM: Homo Sapiens

<400> SEQUENCE: 17

Ala
1

<210> SEQ ID NO 18
<211> LENGTH: 2
<212> TYPE: PRT
<213> ORGANISM: Homo Sapiens
```

<400> SEQUENCE: 18

Ala Ala
1

<210> SEQ ID NO 19
<211> LENGTH: 1228
<212> TYPE: PRT
<213> ORGANISM: Homo Sapiens

<400> SEQUENCE: 19

```
Met Pro Ala Ser Ala Pro Pro Arg Arg Pro Arg Pro Pro Pro Pro Ser
 1               5                  10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350
```

-continued

```
Thr Glu Ser Glu Lys Lys Phe Ile Lys Gly Thr Ala Asp Phe Phe Ala
            355                 360                 365
Leu Cys Phe Gly Pro Thr Leu Ser Phe Gln Leu Leu Asp Pro His Met
    370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
                405                 410                 415
Trp Phe Val Ser Gly Thr Thr Lys Arg Asp Asp Ala Lys Tyr Met Tyr
                420                 425                 430
Tyr Leu Lys Lys Phe Ile Met Glu Thr Leu Lys Ala Ile Lys Leu Asp
            435                 440                 445
Gly Val Asp Val Ile Gly Tyr Thr Ala Trp Ser Leu Met Asp Gly Phe
        450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
            500                 505                 510
Gln Pro Leu Glu Gly Thr Phe Pro Cys Asp Phe Ala Trp Gly Val Val
        515                 520                 525
Asp Asn Tyr Ile Gln Val Asp Thr Thr Leu Ser Gln Phe Thr Asp Leu
    530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
        595                 600                 605
Ser Gln Val Asn His Thr Ile Leu Gln Tyr Tyr Arg Cys Met Ala Ser
    610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
```

```
Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
        820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
        850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
        900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975

His Thr Arg Lys Ser Leu Gly Ser Gly Gly Gly Ser Gly Gly Gly
        980                 985                 990

Gly Ser Gly Gly Gly Gly Ser Leu Lys Tyr Pro Asn Ala Ser Pro Leu
    995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
```

```
                1190                1195                1200
Val Arg Gly Gly Arg Val Asn Thr His Ala Gly Gly Thr Gly Pro
    1205                1210                1215

Glu Gly Cys Arg Pro Phe Ala Lys Phe Ile
    1220                1225

<210> SEQ ID NO 20
<211> LENGTH: 1220
<212> TYPE: PRT
<213> ORGANISM: Homo Sapiens

<400> SEQUENCE: 20

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
                20                  25                  30

Thr Trp Ala Arg Phe Ser Arg Pro Pro Ala Pro Glu Ala Ala Gly Leu
    35                  40                  45

Phe Gln Gly Thr Phe Pro Asp Gly Phe Leu Trp Ala Val Gly Ser Ala
50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205

Arg Asp Tyr Ala Glu Leu Cys Phe Arg His Phe Gly Gly Gln Val Lys
    210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
            260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
    290                 295                 300

Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
                325                 330                 335

Leu Ser Ser Ile Leu Pro Asp Phe Thr Glu Ser Glu Lys Lys Phe Ile
```

```
                340             345             350
Lys Gly Thr Ala Asp Phe Phe Ala Leu Cys Phe Gly Pro Thr Leu Ser
            355                 360                 365
Phe Gln Leu Leu Asp Pro His Met Lys Phe Arg Gln Leu Glu Ser Pro
        370                 375                 380
Asn Leu Arg Gln Leu Leu Ser Trp Ile Asp Leu Glu Phe Asn His Pro
385                 390                 395                 400
Gln Ile Phe Ile Val Glu Asn Gly Trp Phe Val Ser Gly Thr Thr Lys
                405                 410                 415
Arg Asp Asp Ala Lys Tyr Met Tyr Tyr Leu Lys Lys Phe Ile Met Glu
            420                 425                 430
Thr Leu Lys Ala Ile Lys Leu Asp Gly Val Asp Val Ile Gly Tyr Thr
        435                 440                 445
Ala Trp Ser Leu Met Asp Gly Phe Glu Trp His Arg Gly Tyr Ser Ile
        450                 455                 460
Arg Arg Gly Leu Phe Tyr Val Asp Phe Leu Ser Gln Asp Lys Met Leu
465                 470                 475                 480
Leu Pro Lys Ser Ser Ala Leu Phe Tyr Gln Lys Leu Ile Glu Lys Asn
                485                 490                 495
Gly Phe Pro Pro Leu Pro Glu Asn Gln Pro Leu Glu Gly Thr Phe Pro
            500                 505                 510
Cys Asp Phe Ala Trp Gly Val Asp Asn Tyr Ile Gln Val Asp Thr
        515                 520                 525
Thr Leu Ser Gln Phe Thr Asp Leu Asn Val Tyr Leu Trp Asp Val His
        530                 535                 540
His Ser Lys Arg Leu Ile Lys Val Asp Gly Val Val Thr Lys Lys Arg
545                 550                 555                 560
Lys Ser Tyr Cys Val Asp Phe Ala Ala Ile Gln Pro Gln Ile Ala Leu
                565                 570                 575
Leu Gln Glu Met His Val Thr His Phe Arg Phe Ser Leu Asp Trp Ala
            580                 585                 590
Leu Ile Leu Pro Leu Gly Asn Gln Ser Gln Val Asn His Thr Ile Leu
        595                 600                 605
Gln Tyr Tyr Arg Cys Met Ala Ser Glu Leu Val Arg Val Asn Ile Thr
        610                 615                 620
Pro Val Val Ala Leu Trp Gln Pro Met Ala Pro Asn Gln Gly Leu Pro
625                 630                 635                 640
Arg Leu Leu Ala Arg Gln Gly Ala Trp Glu Asn Pro Tyr Thr Ala Leu
                645                 650                 655
Ala Phe Ala Glu Tyr Ala Arg Leu Cys Phe Gln Glu Leu Gly His His
            660                 665                 670
Val Lys Leu Trp Ile Thr Met Asn Glu Pro Tyr Thr Arg Asn Met Thr
        675                 680                 685
Tyr Ser Ala Gly His Asn Leu Leu Lys Ala His Ala Leu Ala Trp His
        690                 695                 700
Val Tyr Asn Glu Lys Phe Arg His Ala Gln Asn Gly Lys Ile Ser Ile
705                 710                 715                 720
Ala Leu Gln Ala Asp Trp Ile Glu Pro Ala Cys Pro Phe Ser Gln Lys
                725                 730                 735
Asp Lys Glu Val Ala Glu Arg Val Leu Glu Phe Asp Ile Gly Trp Leu
            740                 745                 750
Ala Glu Pro Ile Phe Gly Ser Gly Asp Tyr Pro Trp Val Met Arg Asp
        755                 760                 765
```

-continued

Trp Leu Asn Gln Arg Asn Asn Phe Leu Leu Pro Tyr Phe Thr Glu Asp
        770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Pro Trp Gly Leu Arg Lys Val Leu
        835                 840                 845

Asn Trp Leu Lys Phe Lys Tyr Gly Asp Leu Pro Met Tyr Ile Ile Ser
850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
        915                 920                 925

Pro Lys Ala Ser Met Lys His Tyr Arg Lys Ile Ile Asp Ser Asn Gly
930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu Gly Ser
                965                 970                 975

Gly Gly Gly Gly Ser Gly Gly Gly Ser Gly Gly Gly Gly Ser Leu
            980                 985                 990

Lys Tyr Pro Asn Ala Ser Pro Leu Leu Gly Ser Ser Trp Gly Gly Leu
        995                 1000                1005

Ile His Leu Tyr Thr Ala Thr Ala Arg Asn Ser Tyr His Leu Gln
    1010                1015                1020

Ile His Lys Asn Gly His Val Asp Gly Ala Pro His Gln Thr Ile
    1025                1030                1035

Tyr Ser Ala Leu Met Ile Arg Ser Glu Asp Ala Gly Phe Val Val
    1040                1045                1050

Ile Thr Gly Val Met Ser Arg Arg Tyr Leu Cys Met Asp Phe Arg
    1055                1060                1065

Gly Asn Ile Phe Gly Ser His Tyr Phe Asp Pro Glu Asn Cys Arg
    1070                1075                1080

Phe Gln His Gln Thr Leu Glu Asn Gly Tyr Asp Val Tyr His Ser
    1085                1090                1095

Pro Gln Tyr His Phe Leu Val Ser Leu Gly Arg Ala Lys Arg Ala
    1100                1105                1110

Phe Leu Pro Gly Met Asn Pro Pro Tyr Ser Gln Phe Leu Ser
    1115                1120                1125

Arg Arg Asn Glu Ile Pro Leu Ile His Phe Asn Thr Pro Ile Pro
    1130                1135                1140

Arg Arg His Thr Gln Ser Ala Glu Asp Asp Ser Glu Arg Asp Pro
    1145                1150                1155

Leu Asn Val Leu Lys Pro Arg Ala Arg Met Thr Pro Ala Pro Ala
    1160                1165                1170

Ser Cys Ser Gln Glu Leu Pro Ser Ala Glu Asp Asn Ser Pro Met
    1175                1180                1185

-continued

Ala Ser Asp Pro Leu Gly Val Val Arg Gly Gly Arg Val Asn Thr
          1190              1195               1200

His Ala Gly Gly Thr Gly Pro Glu Gly Cys Arg Pro Phe Ala Lys
          1205              1210               1215

Phe Ile
    1220

<210> SEQ ID NO 21
<211> LENGTH: 762
<212> TYPE: PRT
<213> ORGANISM: Homo Sapiens

<400> SEQUENCE: 21

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
        210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

```
Tyr Pro Glu Ser Met Lys Asn Asn Leu Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Ser Gly Gly Gly Ser Gly Gly Gly Gly Ser
            515                 520                 525

Gly Gly Gly Gly Ser Leu Lys Tyr Pro Asn Ala Ser Pro Leu Leu Gly
            530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
                565                 570                 575

His Gln Thr Ile Tyr Ser Ala Leu Met Ile Arg Ser Glu Asp Ala Gly
                580                 585                 590

Phe Val Val Ile Thr Gly Val Met Ser Arg Arg Tyr Leu Cys Met Asp
                595                 600                 605

Phe Arg Gly Asn Ile Phe Gly Ser His Tyr Phe Asp Pro Glu Asn Cys
610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
                645                 650                 655

Leu Pro Gly Met Asn Pro Pro Tyr Ser Gln Phe Leu Ser Arg Arg
            660                 665                 670

Asn Glu Ile Pro Leu Ile His Phe Asn Thr Pro Ile Pro Arg Arg His
            675                 680                 685

Thr Gln Ser Ala Glu Asp Asp Ser Glu Arg Asp Pro Leu Asn Val Leu
            690                 695                 700

Lys Pro Arg Ala Arg Met Thr Pro Ala Pro Ala Ser Cys Ser Gln Glu
705                 710                 715                 720

Leu Pro Ser Ala Glu Asp Asn Ser Pro Met Ala Ser Asp Pro Leu Gly
                725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
```

```
                755                  760

<210> SEQ ID NO 22
<211> LENGTH: 752
<212> TYPE: PRT
<213> ORGANISM: Homo Sapiens

<400> SEQUENCE: 22

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
        355                 360                 365

Val Ala Val Val Pro Trp Gly Leu Arg Lys Val Leu Asn Trp Leu Lys
```

```
                370                 375                 380
Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
            405                 410                 415

Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
            450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
            485                 490                 495

Cys Ser Phe Phe His Thr Arg Lys Ser Leu Gly Ser Gly Gly Gly Gly
            500                 505                 510

Ser Gly Gly Gly Gly Ser Gly Gly Gly Ser Leu Lys Tyr Pro Asn
            515                 520                 525

Ala Ser Pro Leu Leu Gly Ser Ser Trp Gly Gly Leu Ile His Leu Tyr
530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
            565                 570                 575

Arg Ser Glu Asp Ala Gly Phe Val Val Ile Thr Gly Val Met Ser Arg
            580                 585                 590

Arg Tyr Leu Cys Met Asp Phe Arg Gly Asn Ile Phe Gly Ser His Tyr
            595                 600                 605

Phe Asp Pro Glu Asn Cys Arg Phe Gln His Gln Thr Leu Glu Asn Gly
            610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Tyr Ser
            645                 650                 655

Gln Phe Leu Ser Arg Arg Asn Glu Ile Pro Leu Ile His Phe Asn Thr
            660                 665                 670

Pro Ile Pro Arg Arg His Thr Gln Ser Ala Glu Asp Ser Glu Arg
            675                 680                 685

Asp Pro Leu Asn Val Leu Lys Pro Arg Ala Arg Met Thr Pro Ala Pro
690                 695                 700

Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
            725                 730                 735

Ala Gly Gly Thr Gly Pro Glu Gly Cys Arg Pro Phe Ala Lys Phe Ile
            740                 745                 750

<210> SEQ ID NO 23
<211> LENGTH: 1215
<212> TYPE: PRT
<213> ORGANISM: Homo Sapiens

<400> SEQUENCE: 23

Met Pro Ala Ser Ala Pro Pro Arg Arg Pro Arg Pro Pro Pro Pro Ser
```

```
          1               5                  10                 15
Leu Ser Leu Leu Leu Val Leu Leu Gly Leu Gly Gly Arg Arg Leu Arg
                    20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
            370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430
```

-continued

```
Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Thr Phe Pro Asp Gly Phe Leu Trp Ala
        515                 520                 525

Val Gly Ser Ala Ala Tyr Gln Thr Glu Gly Gly Trp Gln Gln His Gly
    530                 535                 540

Lys Gly Ala Ser Ile Trp Asp Thr Phe Thr His His Pro Leu Ala Pro
545                 550                 555                 560

Pro Gly Asp Ser Arg Asn Ala Ser Leu Pro Leu Gly Ala Pro Ser Pro
                565                 570                 575

Leu Gln Pro Ala Thr Gly Asp Val Ala Ser Asp Ser Tyr Asn Asn Val
            580                 585                 590

Phe Arg Asp Thr Glu Ala Leu Arg Glu Leu Gly Val Thr His Tyr Arg
        595                 600                 605

Phe Ser Ile Ser Trp Ala Arg Val Leu Pro Asn Gly Ser Ala Gly Val
    610                 615                 620

Pro Asn Arg Glu Gly Leu Arg Tyr Tyr Arg Arg Leu Leu Glu Arg Leu
625                 630                 635                 640

Arg Glu Leu Gly Val Gln Pro Val Val Thr Leu Tyr His Trp Asp Leu
                645                 650                 655

Pro Gln Arg Leu Gln Asp Ala Tyr Gly Gly Trp Ala Asn Arg Ala Leu
            660                 665                 670

Ala Asp His Phe Arg Asp Tyr Ala Glu Leu Cys Phe Arg His Phe Gly
        675                 680                 685

Gly Gln Val Lys Tyr Trp Ile Thr Ile Asp Asn Pro Tyr Val Val Ala
    690                 695                 700

Trp His Gly Tyr Ala Thr Gly Arg Leu Ala Pro Gly Ile Arg Gly Ser
705                 710                 715                 720

Pro Arg Leu Gly Tyr Leu Val Ala His Asn Leu Leu Leu Ala His Ala
                725                 730                 735

Lys Val Trp His Leu Tyr Asn Thr Ser Phe Arg Pro Thr Gln Gly Gly
            740                 745                 750

Gln Val Ser Ile Ala Leu Ser Ser His Trp Ile Asn Pro Arg Arg Met
        755                 760                 765

Thr Asp His Ser Ile Lys Glu Cys Gln Lys Ser Leu Asp Phe Val Leu
    770                 775                 780

Gly Trp Phe Ala Lys Pro Val Phe Ile Asp Gly Asp Tyr Pro Glu Ser
785                 790                 795                 800

Met Lys Asn Asn Leu Ser Ser Ile Leu Pro Asp Phe Thr Glu Ser Glu
                805                 810                 815

Lys Lys Phe Ile Lys Gly Thr Ala Asp Phe Phe Ala Leu Cys Phe Gly
            820                 825                 830

Pro Thr Leu Ser Phe Gln Leu Leu Asp Pro His Met Lys Phe Arg Gln
        835                 840                 845

Leu Glu Ser Pro Asn Leu Arg Gln Leu Leu Ser Trp Ile Asp Leu Glu
    850                 855                 860
```

```
Phe Asn His Pro Gln Ile Phe Ile Val Glu Asn Gly Trp Phe Val Ser
865                 870                 875                 880

Gly Thr Thr Lys Arg Asp Asp Ala Lys Tyr Met Tyr Leu Lys Lys
                885                 890                 895

Phe Ile Met Glu Thr Leu Lys Ala Ile Lys Leu Asp Gly Val Asp Val
            900                 905                 910

Ile Gly Tyr Thr Ala Trp Ser Leu Met Asp Gly Phe Glu Trp His Arg
        915                 920                 925

Gly Tyr Ser Ile Arg Arg Gly Leu Phe Tyr Val Asp Phe Leu Ser Gln
    930                 935                 940

Asp Lys Met Leu Leu Pro Lys Ser Ser Ala Leu Phe Tyr Gln Lys Leu
945                 950                 955                 960

Ile Glu Lys Asn Gly Phe Pro Glu Phe Gly Ser Gly Gly Gly Gly Ser
                965                 970                 975

Gly Gly Gly Gly Ser Gly Gly Gly Ser Leu Lys Tyr Pro Asn Ala
            980                 985                 990

Ser Pro Leu Leu Gly Ser Ser Trp Gly Gly Leu Ile His Leu Tyr Thr
        995                 1000                1005

Ala Thr Ala Arg Asn Ser Tyr His Leu Gln Ile His Lys Asn Gly
    1010                1015                1020

His Val Asp Gly Ala Pro His Gln Thr Ile Tyr Ser Ala Leu Met
    1025                1030                1035

Ile Arg Ser Glu Asp Ala Gly Phe Val Val Ile Thr Gly Val Met
    1040                1045                1050

Ser Arg Arg Tyr Leu Cys Met Asp Phe Arg Gly Asn Ile Phe Gly
    1055                1060                1065

Ser His Tyr Phe Asp Pro Glu Asn Cys Arg Phe Gln His Gln Thr
    1070                1075                1080

Leu Glu Asn Gly Tyr Asp Val Tyr His Ser Pro Gln Tyr His Phe
    1085                1090                1095

Leu Val Ser Leu Gly Arg Ala Lys Arg Ala Phe Leu Pro Gly Met
    1100                1105                1110

Asn Pro Pro Pro Tyr Ser Gln Phe Leu Ser Arg Arg Asn Glu Ile
    1115                1120                1125

Pro Leu Ile His Phe Asn Thr Pro Ile Pro Arg Arg His Thr Gln
    1130                1135                1140

Ser Ala Glu Asp Asp Ser Glu Arg Asp Pro Leu Asn Val Leu Lys
    1145                1150                1155

Pro Arg Ala Arg Met Thr Pro Ala Pro Ala Ser Cys Ser Gln Glu
    1160                1165                1170

Leu Pro Ser Ala Glu Asp Asn Ser Pro Met Ala Ser Asp Pro Leu
    1175                1180                1185

Gly Val Val Arg Gly Gly Arg Val Asn Thr His Ala Gly Gly Thr
    1190                1195                1200

Gly Pro Glu Gly Cys Arg Pro Phe Ala Lys Phe Ile
    1205                1210                1215

<210> SEQ ID NO 24
<211> LENGTH: 1189
<212> TYPE: PRT
<213> ORGANISM: Homo Sapiens

<400> SEQUENCE: 24

Met Pro Ala Ser Ala Pro Pro Arg Arg Pro Arg Pro Pro Pro Ser
1               5                   10                  15
```

```
Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
            35                  40                  45

Trp Gly Val Val Asp Asn Tyr Ile Gln Val Asp Thr Thr Leu Ser Gln
 50                  55                  60

Phe Thr Asp Leu Asn Val Tyr Leu Trp Asp Val His His Ser Lys Arg
 65                  70                  75                  80

Leu Ile Lys Val Asp Gly Val Val Thr Lys Lys Arg Lys Ser Tyr Cys
                 85                  90                  95

Val Asp Phe Ala Ala Ile Gln Pro Gln Ile Ala Leu Leu Gln Glu Met
                100                 105                 110

His Val Thr His Phe Arg Phe Ser Leu Asp Trp Ala Leu Ile Leu Pro
                115                 120                 125

Leu Gly Asn Gln Ser Gln Val Asn His Thr Ile Leu Gln Tyr Tyr Arg
            130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
            195                 200                 205

Ile Thr Met Asn Glu Pro Tyr Thr Arg Asn Met Thr Tyr Ser Ala Gly
            210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
            275                 280                 285

Phe Gly Ser Gly Asp Tyr Pro Trp Val Met Arg Asp Trp Leu Asn Gln
290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
            355                 360                 365

Val Ala Val Val Pro Trp Gly Leu Arg Lys Val Leu Asn Trp Leu Lys
            370                 375                 380

Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
                405                 410                 415

Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
```

```
                435                 440                 445
        Phe Gly Leu Tyr Arg Tyr Ala Ala Asp Gln Phe Glu Pro Lys Ala Ser
        450                 455                 460

Met Lys His Tyr Arg Lys Ile Ile Asp Ser Asn Gly Phe Pro Gly Pro
        465                 470                 475                 480

Glu Thr Leu Glu Arg Phe Cys Pro Glu Phe Thr Val Cys Thr Glu
                            485                 490                 495

Cys Ser Phe Phe His Thr Arg Lys Ser Leu Gly Thr Phe Pro Cys Asp
                        500                 505                 510

Phe Ala Trp Gly Val Val Asp Asn Tyr Ile Gln Val Asp Thr Thr Leu
                        515                 520                 525

Ser Gln Phe Thr Asp Leu Asn Val Tyr Leu Trp Asp Val His His Ser
                        530                 535                 540

Lys Arg Leu Ile Lys Val Asp Gly Val Val Thr Lys Lys Arg Lys Ser
        545                 550                 555                 560

Tyr Cys Val Asp Phe Ala Ala Ile Gln Pro Gln Ile Ala Leu Leu Gln
                        565                 570                 575

Glu Met His Val Thr His Phe Arg Phe Ser Leu Asp Trp Ala Leu Ile
                        580                 585                 590

Leu Pro Leu Gly Asn Gln Ser Gln Val Asn His Thr Ile Leu Gln Tyr
                        595                 600                 605

Tyr Arg Cys Met Ala Ser Glu Leu Val Arg Val Asn Ile Thr Pro Val
                        610                 615                 620

Val Ala Leu Trp Gln Pro Met Ala Pro Asn Gln Gly Leu Pro Arg Leu
        625                 630                 635                 640

Leu Ala Arg Gln Gly Ala Trp Glu Asn Pro Tyr Thr Ala Leu Ala Phe
                        645                 650                 655

Ala Glu Tyr Ala Arg Leu Cys Phe Gln Glu Leu Gly His His Val Lys
                        660                 665                 670

Leu Trp Ile Thr Met Asn Glu Pro Tyr Thr Arg Asn Met Thr Tyr Ser
                        675                 680                 685

Ala Gly His Asn Leu Leu Lys Ala His Ala Leu Ala Trp His Val Tyr
                        690                 695                 700

Asn Glu Lys Phe Arg His Ala Gln Asn Gly Lys Ile Ser Ile Ala Leu
        705                 710                 715                 720

Gln Ala Asp Trp Ile Glu Pro Ala Cys Pro Phe Ser Gln Lys Asp Lys
                        725                 730                 735

Glu Val Ala Glu Arg Val Leu Glu Phe Asp Ile Gly Trp Leu Ala Glu
                        740                 745                 750

Pro Ile Phe Gly Ser Gly Asp Tyr Pro Trp Val Met Arg Asp Trp Leu
                        755                 760                 765

Asn Gln Arg Asn Asn Phe Leu Leu Pro Tyr Phe Thr Glu Asp Glu Lys
                        770                 775                 780

Lys Leu Ile Gln Gly Thr Phe Asp Phe Leu Ala Leu Ser His Tyr Thr
        785                 790                 795                 800

Thr Ile Leu Val Asp Ser Glu Lys Glu Asp Pro Ile Lys Tyr Asn Asp
                        805                 810                 815

Tyr Leu Glu Val Gln Glu Met Thr Asp Ile Thr Trp Leu Asn Ser Pro
                        820                 825                 830

Ser Gln Val Ala Val Pro Trp Gly Leu Arg Lys Val Leu Asn Trp
                        835                 840                 845

Leu Lys Phe Lys Tyr Gly Asp Leu Pro Met Tyr Ile Ile Ser Asn Gly
        850                 855                 860
```

```
Ile Asp Asp Gly Leu His Ala Glu Asp Gln Leu Arg Val Tyr Tyr
865                 870                 875                 880

Met Gln Asn Tyr Ile Asn Glu Ala Leu Lys Ala His Ile Leu Asp Gly
                885                 890                 895

Ile Asn Leu Cys Gly Tyr Phe Ala Tyr Ser Phe Asn Asp Arg Thr Ala
            900                 905                 910

Pro Arg Phe Gly Leu Tyr Arg Tyr Ala Ala Asp Gln Phe Glu Pro Lys
        915                 920                 925

Ala Ser Met Lys His Tyr Arg Lys Ile Ile Asp Ser Asn Gly Phe Gly
    930                 935                 940

Ser Gly Gly Gly Gly Ser Gly Gly Gly Ser Gly Gly Gly Gly Ser
945                 950                 955                 960

Leu Lys Tyr Pro Asn Ala Ser Pro Leu Leu Gly Ser Ser Trp Gly Gly
                965                 970                 975

Leu Ile His Leu Tyr Thr Ala Thr Ala Arg Asn Ser Tyr His Leu Gln
            980                 985                 990

Ile His Lys Asn Gly His Val Asp Gly Ala Pro His Gln Thr Ile Tyr
        995                 1000                1005

Ser Ala Leu Met Ile Arg Ser Glu Asp Ala Gly Phe Val Val Ile
    1010                1015                1020

Thr Gly Val Met Ser Arg Arg Tyr Leu Cys Met Asp Phe Arg Gly
    1025                1030                1035

Asn Ile Phe Gly Ser His Tyr Phe Asp Pro Glu Asn Cys Arg Phe
    1040                1045                1050

Gln His Gln Thr Leu Glu Asn Gly Tyr Asp Val Tyr His Ser Pro
    1055                1060                1065

Gln Tyr His Phe Leu Val Ser Leu Gly Arg Ala Lys Arg Ala Phe
    1070                1075                1080

Leu Pro Gly Met Asn Pro Pro Tyr Ser Gln Phe Leu Ser Arg
    1085                1090                1095

Arg Asn Glu Ile Pro Leu Ile His Phe Asn Thr Pro Ile Pro Arg
    1100                1105                1110

Arg His Thr Gln Ser Ala Glu Asp Asp Ser Glu Arg Asp Pro Leu
    1115                1120                1125

Asn Val Leu Lys Pro Arg Ala Arg Met Thr Pro Ala Pro Ala Ser
    1130                1135                1140

Cys Ser Gln Glu Leu Pro Ser Ala Glu Asp Asn Ser Pro Met Ala
    1145                1150                1155

Ser Asp Pro Leu Gly Val Val Arg Gly Gly Arg Val Asn Thr His
    1160                1165                1170

Ala Gly Gly Thr Gly Pro Glu Gly Cys Arg Pro Phe Ala Lys Phe
    1175                1180                1185

Ile

<210> SEQ ID NO 25
<211> LENGTH: 1219
<212> TYPE: PRT
<213> ORGANISM: Homo Sapiens

<400> SEQUENCE: 25

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
```

-continued

```
            35                  40                  45
Asn Ser Tyr His Leu Gln Ile His Lys Asn Gly His Val Asp Gly Ala
 50                  55                  60
Pro His Gln Thr Ile Tyr Ser Ala Leu Met Ile Arg Ser Glu Asp Ala
 65                  70                  75                  80
Gly Phe Val Val Ile Thr Gly Val Met Ser Arg Arg Tyr Leu Cys Met
                     85                  90                  95
Asp Phe Arg Gly Asn Ile Phe Gly Ser His Tyr Phe Asp Pro Glu Asn
                100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Ser Glu Arg Asp Pro Leu Asn Val
            180                 185                 190
Leu Lys Pro Arg Ala Arg Met Thr Pro Ala Pro Ala Ser Cys Ser Gln
            195                 200                 205
Glu Leu Pro Ser Ala Glu Asp Asn Ser Pro Met Ala Ser Asp Pro Leu
210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gly Ser Gly Gly Gly
                245                 250                 255
Gly Ser Gly Gly Gly Ser Gly Gly Gly Ser Leu Lys Glu Pro
                260                 265                 270
Gly Asp Gly Ala Gln Thr Trp Ala Arg Phe Ser Arg Pro Pro Ala Pro
            275                 280                 285
Glu Ala Ala Gly Leu Phe Gln Gly Thr Phe Pro Asp Gly Phe Leu Trp
            290                 295                 300
Ala Val Gly Ser Ala Ala Tyr Gln Thr Glu Gly Gly Trp Gln Gln His
305                 310                 315                 320
Gly Lys Gly Ala Ser Ile Trp Asp Thr Phe Thr His His Pro Leu Ala
                325                 330                 335
Pro Pro Gly Asp Ser Arg Asn Ala Ser Leu Pro Leu Gly Ala Pro Ser
            340                 345                 350
Pro Leu Gln Pro Ala Thr Gly Asp Val Ala Ser Asp Ser Tyr Asn Asn
            355                 360                 365
Val Phe Arg Asp Thr Glu Ala Leu Arg Glu Leu Gly Val Thr His Tyr
370                 375                 380
Arg Phe Ser Ile Ser Trp Ala Arg Val Leu Pro Asn Gly Ser Ala Gly
385                 390                 395                 400
Val Pro Asn Arg Glu Gly Leu Arg Tyr Tyr Arg Arg Leu Leu Glu Arg
                405                 410                 415
Leu Arg Glu Leu Gly Val Gln Pro Val Val Thr Leu Tyr His Trp Asp
            420                 425                 430
Leu Pro Gln Arg Leu Gln Asp Ala Tyr Gly Gly Trp Ala Asn Arg Ala
            435                 440                 445
Leu Ala Asp His Phe Arg Asp Tyr Ala Glu Leu Cys Phe Arg His Phe
            450                 455                 460
```

```
Gly Gly Gln Val Lys Tyr Trp Ile Thr Ile Asp Asn Pro Tyr Val Val
465                 470                 475                 480

Ala Trp His Gly Tyr Ala Thr Gly Arg Leu Ala Pro Gly Ile Arg Gly
            485                 490                 495

Ser Pro Arg Leu Gly Tyr Leu Val Ala His Asn Leu Leu Leu Ala His
                500                 505                 510

Ala Lys Val Trp His Leu Tyr Asn Thr Ser Phe Arg Pro Thr Gln Gly
            515                 520                 525

Gly Gln Val Ser Ile Ala Leu Ser Ser His Trp Ile Asn Pro Arg Arg
                530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
            565                 570                 575

Ser Met Lys Asn Asn Leu Ser Ser Ile Leu Pro Asp Phe Thr Glu Ser
                580                 585                 590

Glu Lys Lys Phe Ile Lys Gly Thr Ala Asp Phe Phe Ala Leu Cys Phe
            595                 600                 605

Gly Pro Thr Leu Ser Phe Gln Leu Leu Asp Pro His Met Lys Phe Arg
610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
                645                 650                 655

Ser Gly Thr Thr Lys Arg Asp Asp Ala Lys Tyr Met Tyr Tyr Leu Lys
                660                 665                 670

Lys Phe Ile Met Glu Thr Leu Lys Ala Ile Lys Leu Asp Gly Val Asp
            675                 680                 685

Val Ile Gly Tyr Thr Ala Trp Ser Leu Met Asp Gly Phe Glu Trp His
    690                 695                 700

Arg Gly Tyr Ser Ile Arg Arg Gly Leu Phe Tyr Val Asp Phe Leu Ser
705                 710                 715                 720

Gln Asp Lys Met Leu Leu Pro Lys Ser Ser Ala Leu Phe Tyr Gln Lys
                725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
                755                 760                 765

Ile Gln Val Asp Thr Thr Leu Ser Gln Phe Thr Asp Leu Asn Val Tyr
                770                 775                 780

Leu Trp Asp Val His His Ser Lys Arg Leu Ile Lys Val Asp Gly Val
785                 790                 795                 800

Val Thr Lys Lys Arg Lys Ser Tyr Cys Val Asp Phe Ala Ala Ile Gln
                805                 810                 815

Pro Gln Ile Ala Leu Leu Gln Glu Met His Val Thr His Phe Arg Phe
                820                 825                 830

Ser Leu Asp Trp Ala Leu Ile Leu Pro Leu Gly Asn Gln Ser Gln Val
                835                 840                 845

Asn His Thr Ile Leu Gln Tyr Tyr Arg Cys Met Ala Ser Glu Leu Val
                850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
                885                 890                 895
```

-continued

```
Pro Tyr Thr Ala Leu Ala Phe Ala Glu Tyr Ala Arg Leu Cys Phe Gln
            900                 905                 910
Glu Leu Gly His His Val Lys Leu Trp Ile Thr Met Asn Glu Pro Tyr
            915                 920                 925
Thr Arg Asn Met Thr Tyr Ser Ala Gly His Asn Leu Leu Lys Ala His
        930                 935                 940
Ala Leu Ala Trp His Val Tyr Asn Glu Lys Phe Arg His Ala Gln Asn
945                 950                 955                 960
Gly Lys Ile Ser Ile Ala Leu Gln Ala Asp Trp Ile Glu Pro Ala Cys
                965                 970                 975
Pro Phe Ser Gln Lys Asp Lys Glu Val Ala Glu Arg Val Leu Glu Phe
            980                 985                 990
Asp Ile Gly Trp Leu Ala Glu Pro Ile Phe Gly Ser Gly Asp Tyr Pro
            995                 1000                1005
Trp Val Met Arg Asp Trp Leu Asn Gln Arg Asn Phe Leu Leu
            1010                1015                1020
Pro Tyr Phe Thr Glu Asp Glu Lys Lys Leu Ile Gln Gly Thr Phe
            1025                1030                1035
Asp Phe Leu Ala Leu Ser His Tyr Thr Thr Ile Leu Val Asp Ser
            1040                1045                1050
Glu Lys Glu Asp Pro Ile Lys Tyr Asn Asp Tyr Leu Glu Val Gln
            1055                1060                1065
Glu Met Thr Asp Ile Thr Trp Leu Asn Ser Pro Ser Gln Val Ala
            1070                1075                1080
Val Val Pro Trp Gly Leu Arg Lys Val Leu Asn Trp Leu Lys Phe
            1085                1090                1095
Lys Tyr Gly Asp Leu Pro Met Tyr Ile Ile Ser Asn Gly Ile Asp
            1100                1105                1110
Asp Gly Leu His Ala Glu Asp Asp Gln Leu Arg Val Tyr Tyr Met
            1115                1120                1125
Gln Asn Tyr Ile Asn Glu Ala Leu Lys Ala His Ile Leu Asp Gly
            1130                1135                1140
Ile Asn Leu Cys Gly Tyr Phe Ala Tyr Ser Phe Asn Asp Arg Thr
            1145                1150                1155
Ala Pro Arg Phe Gly Leu Tyr Arg Tyr Ala Ala Asp Gln Phe Glu
            1160                1165                1170
Pro Lys Ala Ser Met Lys His Tyr Arg Lys Ile Ile Asp Ser Asn
            1175                1180                1185
Gly Phe Pro Gly Pro Glu Thr Leu Glu Arg Phe Cys Pro Glu Glu
            1190                1195                1200
Phe Thr Val Cys Thr Glu Cys Ser Phe Phe His Thr Arg Lys Ser
            1205                1210                1215
Leu

<210> SEQ ID NO 26
<211> LENGTH: 700
<212> TYPE: PRT
<213> ORGANISM: Homo Sapiens

<400> SEQUENCE: 26

Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
            20                  25                  30
```

```
Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                     85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
                115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
                180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
                260                 265                 270

Gly Trp Gln Gln His Gly Lys Gly Ala Ser Ile Trp Asp Thr Phe Thr
                275                 280                 285

His His Pro Leu Ala Pro Pro Gly Asp Ser Arg Asn Ala Ser Leu Pro
        290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
                340                 345                 350

Asn Gly Ser Ala Gly Val Pro Asn Arg Glu Gly Leu Arg Tyr Tyr Arg
                355                 360                 365

Arg Leu Leu Glu Arg Leu Arg Glu Leu Gly Val Gln Pro Val Val Thr
        370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
                420                 425                 430

Asn Pro Tyr Val Val Ala Trp His Gly Tyr Ala Thr Gly Arg Leu Ala
                435                 440                 445

Pro Gly Ile Arg Gly Ser Pro Arg Leu Gly Tyr Leu Val Ala His Asn
450                 455                 460
```

Leu Leu Leu Ala His Ala Lys Val Trp His Leu Tyr Asn Thr Ser Phe
465                 470                 475                 480

Arg Pro Thr Gln Gly Gln Val Ser Ile Ala Leu Ser Ser His Trp
            485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
            515                 520                 525

Gly Asp Tyr Pro Glu Ser Met Lys Asn Asn Leu Ser Ser Ile Leu Pro
            530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
            565                 570                 575

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
            595                 600                 605

Asn Gly Trp Phe Val Ser Gly Thr Thr Lys Arg Asp Asp Ala Lys Tyr
            610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
            645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
            675                 680                 685

Leu Phe Tyr Gln Lys Leu Ile Glu Lys Asn Gly Phe
690                 695                 700

<210> SEQ ID NO 27
<211> LENGTH: 688
<212> TYPE: PRT
<213> ORGANISM: Homo Sapiens

<400> SEQUENCE: 27

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
            85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
            130                 135                 140

-continued

```
Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
        210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                245                 250                 255

Asp Phe Ala Trp Gly Val Val Asp Asn Tyr Ile Gln Val Asp Thr Thr
                260                 265                 270

Leu Ser Gln Phe Thr Asp Leu Asn Val Tyr Leu Trp Asp Val His His
            275                 280                 285

Ser Lys Arg Leu Ile Lys Val Asp Gly Val Val Thr Lys Lys Arg Lys
290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                325                 330                 335

Ile Leu Pro Leu Gly Asn Gln Ser Gln Val Asn His Thr Ile Leu Gln
                340                 345                 350

Tyr Tyr Arg Cys Met Ala Ser Glu Leu Val Arg Val Asn Ile Thr Pro
            355                 360                 365

Val Val Ala Leu Trp Gln Pro Met Ala Pro Asn Gln Gly Leu Pro Arg
370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                405                 410                 415

Lys Leu Trp Ile Thr Met Asn Glu Pro Tyr Thr Arg Asn Met Thr Tyr
                420                 425                 430

Ser Ala Gly His Asn Leu Leu Lys Ala His Ala Leu Ala Trp His Val
            435                 440                 445

Tyr Asn Glu Lys Phe Arg His Ala Gln Asn Gly Lys Ile Ser Ile Ala
450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
                500                 505                 510

Leu Asn Gln Arg Asn Asn Phe Leu Leu Pro Tyr Phe Thr Glu Asp Glu
            515                 520                 525

Lys Lys Leu Ile Gln Gly Thr Phe Asp Phe Leu Ala Leu Ser His Tyr
            530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
```

```
                       565                 570                 575
Pro Ser Gln Val Ala Val Val Pro Trp Gly Leu Arg Lys Val Leu Asn
            580                 585                 590

Trp Leu Lys Phe Lys Tyr Gly Asp Leu Pro Met Tyr Ile Ile Ser Asn
            595                 600                 605

Gly Ile Asp Asp Gly Leu His Ala Glu Asp Asp Gln Leu Arg Val Tyr
            610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
            675                 680                 685

<210> SEQ ID NO 28
<211> LENGTH: 1149
<212> TYPE: PRT
<213> ORGANISM: Homo Sapiens

<400> SEQUENCE: 28

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val Leu
            180                 185                 190

Lys Pro Arg Ala Arg Met Thr Pro Ala Pro Ala Ser Cys Ser Gln Glu
        195                 200                 205

Leu Pro Ser Ala Glu Asp Asn Ser Pro Met Ala Ser Asp Pro Leu Gly
    210                 215                 220

Val Val Arg Gly Gly Arg Val Asn Thr His Ala Gly Gly Thr Gly Pro
225                 230                 235                 240

Glu Gly Cys Arg Pro Phe Ala Lys Phe Ile Gln Gly Thr Phe Pro Asp
                245                 250                 255

Gly Phe Leu Trp Ala Val Gly Ser Ala Ala Tyr Gln Thr Glu Gly
```

```
                260              265              270
Gly Trp Gln Gln His Gly Lys Gly Ala Ser Ile Trp Asp Thr Phe Thr
            275              280              285
His His Pro Leu Ala Pro Pro Gly Asp Ser Arg Asn Ala Ser Leu Pro
        290              295              300
Leu Gly Ala Pro Ser Pro Leu Gln Pro Ala Thr Gly Asp Val Ala Ser
305              310              315              320
Asp Ser Tyr Asn Asn Val Phe Arg Asp Thr Glu Ala Leu Arg Glu Leu
            325              330              335
Gly Val Thr His Tyr Arg Phe Ser Ile Ser Trp Ala Arg Val Leu Pro
            340              345              350
Asn Gly Ser Ala Gly Val Pro Asn Arg Glu Gly Leu Arg Tyr Tyr Arg
            355              360              365
Arg Leu Leu Glu Arg Leu Arg Glu Leu Gly Val Gln Pro Val Val Thr
        370              375              380
Leu Tyr His Trp Asp Leu Pro Gln Arg Leu Gln Asp Ala Tyr Gly Gly
385              390              395              400
Trp Ala Asn Arg Ala Leu Ala Asp His Phe Arg Asp Tyr Ala Glu Leu
            405              410              415
Cys Phe Arg His Phe Gly Gly Gln Val Lys Tyr Trp Ile Thr Ile Asp
            420              425              430
Asn Pro Tyr Val Val Ala Trp His Gly Tyr Ala Thr Gly Arg Leu Ala
            435              440              445
Pro Gly Ile Arg Gly Ser Pro Arg Leu Gly Tyr Leu Val Ala His Asn
        450              455              460
Leu Leu Leu Ala His Ala Lys Val Trp His Leu Tyr Asn Thr Ser Phe
465              470              475              480
Arg Pro Thr Gln Gly Gly Gln Val Ser Ile Ala Leu Ser Ser His Trp
            485              490              495
Ile Asn Pro Arg Arg Met Thr Asp His Ser Ile Lys Glu Cys Gln Lys
            500              505              510
Ser Leu Asp Phe Val Leu Gly Trp Phe Ala Lys Pro Val Phe Ile Asp
            515              520              525
Gly Asp Tyr Pro Glu Ser Met Lys Asn Asn Leu Ser Ser Ile Leu Pro
        530              535              540
Asp Phe Thr Glu Ser Glu Lys Lys Phe Ile Lys Gly Thr Ala Asp Phe
545              550              555              560
Phe Ala Leu Cys Phe Gly Pro Thr Leu Ser Phe Gln Leu Leu Asp Pro
            565              570              575
His Met Lys Phe Arg Gln Leu Glu Ser Pro Asn Leu Arg Gln Leu Leu
            580              585              590
Ser Trp Ile Asp Leu Glu Phe Asn His Pro Gln Ile Phe Ile Val Glu
            595              600              605
Asn Gly Trp Phe Val Ser Gly Thr Thr Lys Arg Asp Asp Ala Lys Tyr
            610              615              620
Met Tyr Tyr Leu Lys Lys Phe Ile Met Glu Thr Leu Lys Ala Ile Lys
625              630              635              640
Leu Asp Gly Val Asp Val Ile Gly Tyr Thr Ala Trp Ser Leu Met Asp
            645              650              655
Gly Phe Glu Trp His Arg Gly Tyr Ser Ile Arg Arg Gly Leu Phe Tyr
            660              665              670
Val Asp Phe Leu Ser Gln Asp Lys Met Leu Leu Pro Lys Ser Ser Ala
        675              680              685
```

-continued

Leu Phe Tyr Gln Lys Leu Ile Glu Lys Asn Gly Phe Gln Gly Thr Phe
690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
            725                 730                 735

Thr His His Pro Leu Ala Pro Pro Gly Asp Ser Arg Asn Ala Ser Leu
        740                 745                 750

Pro Leu Gly Ala Pro Ser Pro Leu Gln Pro Ala Thr Gly Asp Val Ala
    755                 760                 765

Ser Asp Ser Tyr Asn Asn Val Phe Arg Asp Thr Glu Ala Leu Arg Glu
770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
            805                 810                 815

Arg Arg Leu Leu Glu Arg Leu Arg Glu Leu Gly Val Gln Pro Val Val
        820                 825                 830

Thr Leu Tyr His Trp Asp Leu Pro Gln Arg Leu Gln Asp Ala Tyr Gly
    835                 840                 845

Gly Trp Ala Asn Arg Ala Leu Ala Asp His Phe Arg Asp Tyr Ala Glu
850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
            885                 890                 895

Ala Pro Gly Ile Arg Gly Ser Pro Arg Leu Gly Tyr Leu Val Ala His
        900                 905                 910

Asn Leu Leu Leu Ala His Ala Lys Val Trp His Leu Tyr Asn Thr Ser
    915                 920                 925

Phe Arg Pro Thr Gln Gly Gly Gln Val Ser Ile Ala Leu Ser Ser His
930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
            965                 970                 975

Asp Gly Asp Tyr Pro Glu Ser Met Lys Asn Asn Leu Ser Ser Ile Leu
        980                 985                 990

Pro Asp Phe Thr Glu Ser Glu Lys Lys Phe Ile Lys Gly Thr Ala Asp
    995                 1000                1005

Phe Phe Ala Leu Cys Phe Gly Pro Thr Leu Ser Phe Gln Leu Leu
    1010                1015                1020

Asp Pro His Met Lys Phe Arg Gln Leu Glu Ser Pro Asn Leu Arg
    1025                1030                1035

Gln Leu Leu Ser Trp Ile Asp Leu Glu Phe Asn His Pro Gln Ile
    1040                1045                1050

Phe Ile Val Glu Asn Gly Trp Phe Val Ser Gly Thr Thr Lys Arg
    1055                1060                1065

Asp Asp Ala Lys Tyr Met Tyr Leu Lys Lys Phe Ile Met Glu
    1070                1075                1080

Thr Leu Lys Ala Ile Lys Leu Asp Gly Val Asp Val Ile Gly Tyr
    1085                1090                1095

Thr Ala Trp Ser Leu Met Asp Gly Phe Glu Trp His Arg Gly Tyr
    1100                1105                1110

Ser Ile Arg Arg Gly Leu Phe Tyr Val Asp Phe Leu Ser Gln Asp
    1115                1120                1125

Lys Met Leu Leu Pro Lys Ser Ser Ala Leu Phe Tyr Gln Lys Leu
    1130                1135                1140

Ile Glu Lys Asn Gly Phe
    1145

<210> SEQ ID NO 29
<211> LENGTH: 1125
<212> TYPE: PRT
<213> ORGANISM: Homo Sapiens

<400> SEQUENCE: 29

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                245                 250                 255

Asp Phe Ala Trp Gly Val Val Asp Asn Tyr Ile Gln Val Asp Thr Thr
            260                 265                 270

Leu Ser Gln Phe Thr Asp Leu Asn Val Tyr Leu Trp Asp Val His His
            275                 280                 285

Ser Lys Arg Leu Ile Lys Val Asp Gly Val Val Thr Lys Lys Arg Lys
    290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                325                 330                 335

-continued

```
Ile Leu Pro Leu Gly Asn Gln Ser Gln Val Asn His Thr Ile Leu Gln
            340                 345                 350
Tyr Tyr Arg Cys Met Ala Ser Glu Leu Val Arg Val Asn Ile Thr Pro
            355                 360                 365
Val Val Ala Leu Trp Gln Pro Met Ala Pro Asn Gln Gly Leu Pro Arg
            370                 375                 380
Leu Leu Ala Arg Gln Gly Ala Trp Glu Asn Pro Tyr Thr Ala Leu Ala
385                 390                 395                 400
Phe Ala Glu Tyr Ala Arg Leu Cys Phe Gln Glu Leu Gly His Val
                    405                 410                 415
Lys Leu Trp Ile Thr Met Asn Glu Pro Tyr Thr Arg Asn Met Thr Tyr
                    420                 425                 430
Ser Ala Gly His Asn Leu Leu Lys Ala His Ala Leu Ala Trp His Val
                    435                 440                 445
Tyr Asn Glu Lys Phe Arg His Ala Gln Asn Gly Lys Ile Ser Ile Ala
                    450                 455                 460
Leu Gln Ala Asp Trp Ile Glu Pro Ala Cys Pro Phe Ser Gln Lys Asp
465                 470                 475                 480
Lys Glu Val Ala Glu Arg Val Leu Glu Phe Asp Ile Gly Trp Leu Ala
                    485                 490                 495
Glu Pro Ile Phe Gly Ser Gly Asp Tyr Pro Trp Val Met Arg Asp Trp
                    500                 505                 510
Leu Asn Gln Arg Asn Asn Phe Leu Leu Pro Tyr Phe Thr Glu Asp Glu
                    515                 520                 525
Lys Lys Leu Ile Gln Gly Thr Phe Asp Phe Leu Ala Leu Ser His Tyr
530                 535                 540
Thr Thr Ile Leu Val Asp Ser Glu Lys Glu Asp Pro Ile Lys Tyr Asn
545                 550                 555                 560
Asp Tyr Leu Glu Val Gln Glu Met Thr Asp Ile Thr Trp Leu Asn Ser
                    565                 570                 575
Pro Ser Gln Val Ala Val Val Pro Trp Gly Leu Arg Lys Val Leu Asn
                    580                 585                 590
Trp Leu Lys Phe Lys Tyr Gly Asp Leu Pro Met Tyr Ile Ile Ser Asn
                    595                 600                 605
Gly Ile Asp Asp Gly Leu His Ala Glu Asp Asp Gln Leu Arg Val Tyr
            610                 615                 620
Tyr Met Gln Asn Tyr Ile Asn Glu Ala Leu Lys Ala His Ile Leu Asp
625                 630                 635                 640
Gly Ile Asn Leu Cys Gly Tyr Phe Ala Tyr Ser Phe Asn Asp Arg Thr
                    645                 650                 655
Ala Pro Arg Phe Gly Leu Tyr Arg Tyr Ala Ala Asp Gln Phe Glu Pro
                    660                 665                 670
Lys Ala Ser Met Lys His Tyr Arg Lys Ile Ile Asp Ser Asn Gly Phe
                    675                 680                 685
Gly Thr Phe Pro Cys Asp Phe Ala Trp Gly Val Val Asp Asn Tyr Ile
            690                 695                 700
Gln Val Asp Thr Thr Leu Ser Gln Phe Thr Asp Leu Asn Val Tyr Leu
705                 710                 715                 720
Trp Asp Val His His Ser Lys Arg Leu Ile Lys Val Asp Gly Val Val
                    725                 730                 735
Thr Lys Lys Arg Lys Ser Tyr Cys Val Asp Phe Ala Ala Ile Gln Pro
            740                 745                 750
Gln Ile Ala Leu Leu Gln Glu Met His Val Thr His Phe Arg Phe Ser
```

```
                    755                 760                 765
Leu Asp Trp Ala Leu Ile Leu Pro Leu Gly Asn Gln Ser Gln Val Asn
    770                 775                 780

His Thr Ile Leu Gln Tyr Tyr Arg Cys Met Ala Ser Glu Leu Val Arg
785                 790                 795                 800

Val Asn Ile Thr Pro Val Ala Leu Trp Gln Pro Met Ala Pro Asn
                805                 810                 815

Gln Gly Leu Pro Arg Leu Leu Ala Arg Gln Gly Ala Trp Glu Asn Pro
                820                 825                 830

Tyr Thr Ala Leu Ala Phe Ala Glu Tyr Ala Arg Leu Cys Phe Gln Glu
                835                 840                 845

Leu Gly His His Val Lys Leu Trp Ile Thr Met Asn Glu Pro Tyr Thr
850                 855                 860

Arg Asn Met Thr Tyr Ser Ala Gly His Asn Leu Leu Lys Ala His Ala
865                 870                 875                 880

Leu Ala Trp His Val Tyr Asn Glu Lys Phe Arg His Ala Gln Asn Gly
                885                 890                 895

Lys Ile Ser Ile Ala Leu Gln Ala Asp Trp Ile Glu Pro Ala Cys Pro
                900                 905                 910

Phe Ser Gln Lys Asp Lys Glu Val Ala Glu Arg Val Leu Glu Phe Asp
                915                 920                 925

Ile Gly Trp Leu Ala Glu Pro Ile Phe Gly Ser Gly Asp Tyr Pro Trp
                930                 935                 940

Val Met Arg Asp Trp Leu Asn Gln Arg Asn Asn Phe Leu Leu Pro Tyr
945                 950                 955                 960

Phe Thr Glu Asp Glu Lys Lys Leu Ile Gln Gly Thr Phe Asp Phe Leu
                965                 970                 975

Ala Leu Ser His Tyr Thr Thr Ile Leu Val Asp Ser Glu Lys Glu Asp
                980                 985                 990

Pro Ile Lys Tyr Asn Asp Tyr Leu Glu Val Gln Glu Met Thr Asp Ile
                995                 1000                1005

Thr Trp Leu Asn Ser Pro Ser Gln Val Ala Val Val Pro Trp Gly
                1010                1015                1020

Leu Arg Lys Val Leu Asn Trp Leu Lys Phe Lys Tyr Gly Asp Leu
                1025                1030                1035

Pro Met Tyr Ile Ile Ser Asn Gly Ile Asp Asp Gly Leu His Ala
                1040                1045                1050

Glu Asp Asp Gln Leu Arg Val Tyr Tyr Met Gln Asn Tyr Ile Asn
                1055                1060                1065

Glu Ala Leu Lys Ala His Ile Leu Asp Gly Ile Asn Leu Cys Gly
                1070                1075                1080

Tyr Phe Ala Tyr Ser Phe Asn Asp Arg Thr Ala Pro Arg Phe Gly
                1085                1090                1095

Leu Tyr Arg Tyr Ala Ala Asp Gln Phe Glu Pro Lys Ala Ser Met
                1100                1105                1110

Lys His Tyr Arg Lys Ile Ile Asp Ser Asn Gly Phe
                1115                1120                1125

<210> SEQ ID NO 30
<211> LENGTH: 2157
<212> TYPE: PRT
<213> ORGANISM: Homo Sapiens

<400> SEQUENCE: 30

Gly Cys Thr Cys Cys Cys Ala Gly Cys Cys Ala Ala Gly Ala Ala Cys
```

-continued

```
1               5                   10                  15

Cys Thr Cys Gly Gly Gly Gly Cys Cys Gly Cys Thr Gly Cys Gly Cys
            20                  25                  30

Gly Gly Thr Gly Gly Gly Gly Ala Gly Gly Ala Gly Thr Thr Cys Cys
        35                  40                  45

Cys Cys Gly Ala Ala Ala Cys Cys Cys Gly Gly Cys Cys Gly Cys Thr
    50                  55                  60

Ala Ala Gly Cys Gly Ala Gly Gly Cys Cys Thr Cys Cys Thr Cys Cys
65                  70                  75                  80

Thr Cys Cys Cys Gly Cys Ala Gly Ala Thr Cys Cys Gly Ala Ala Cys
                85                  90                  95

Gly Gly Cys Cys Thr Gly Gly Gly Cys Gly Gly Gly Gly Thr Cys Ala
            100                 105                 110

Cys Cys Cys Cys Gly Gly Cys Thr Gly Gly Gly Ala Cys Ala Ala Gly
        115                 120                 125

Ala Ala Gly Cys Cys Gly Cys Cys Gly Cys Cys Thr Gly Cys Cys Thr
    130                 135                 140

Gly Cys Cys Cys Gly Gly Gly Cys Cys Cys Gly Gly Gly Gly Ala Gly
145                 150                 155                 160

Gly Gly Gly Gly Cys Thr Gly Gly Gly Gly Cys Thr Gly Gly Gly Gly
                165                 170                 175

Cys Cys Gly Gly Ala Gly Gly Cys Gly Gly Gly Gly Thr Gly Thr Gly
            180                 185                 190

Ala Gly Thr Gly Gly Gly Thr Gly Thr Gly Thr Gly Cys Gly Gly Gly
        195                 200                 205

Gly Gly Gly Cys Gly Gly Ala Gly Gly Cys Thr Thr Gly Ala Thr Gly
    210                 215                 220

Cys Ala Ala Thr Cys Cys Cys Gly Ala Thr Ala Ala Gly Ala Ala Ala
225                 230                 235                 240

Thr Gly Cys Thr Cys Gly Gly Gly Thr Gly Thr Cys Thr Thr Gly Gly
                245                 250                 255

Gly Cys Ala Cys Cys Thr Ala Cys Cys Cys Gly Thr Gly Gly Gly Gly
            260                 265                 270

Cys Cys Cys Gly Thr Ala Ala Gly Gly Cys Gly Cys Thr Ala Cys Thr
        275                 280                 285

Ala Thr Ala Thr Ala Ala Gly Gly Cys Thr Gly Cys Cys Gly Gly Cys
    290                 295                 300

Cys Cys Gly Gly Ala Gly Cys Cys Gly Cys Cys Gly Cys Gly Cys Cys
305                 310                 315                 320

Gly Thr Cys Ala Gly Ala Gly Cys Ala Gly Gly Ala Gly Cys Gly Cys
                325                 330                 335

Thr Gly Cys Gly Thr Cys Cys Ala Gly Gly Ala Thr Cys Thr Ala Gly
            340                 345                 350

Gly Gly Cys Cys Ala Cys Gly Ala Cys Cys Ala Thr Cys Cys Cys Ala
        355                 360                 365

Ala Cys Cys Cys Gly Gly Cys Ala Cys Thr Cys Ala Cys Ala Gly Cys
    370                 375                 380

Cys Cys Cys Gly Cys Ala Gly Cys Gly Cys Ala Thr Cys Cys Cys Gly
385                 390                 395                 400

Gly Thr Cys Gly Cys Cys Gly Cys Cys Cys Ala Gly Cys Cys Thr Cys
                405                 410                 415

Cys Cys Gly Cys Ala Cys Cys Cys Cys Cys Ala Thr Cys Gly Cys Cys
            420                 425                 430
```

```
Gly Gly Ala Gly Cys Thr Cys Gly Cys Cys Gly Ala Gly
        435                 440                 445

Cys Cys Cys Cys Ala Gly Gly Ala Gly Gly Thr Gly Cys Cys Ala
450                 455                 460

Thr Gly Cys Gly Gly Ala Gly Cys Gly Gly Gly Thr Gly Thr Gly Thr
465                 470                 475                 480

Gly Gly Thr Gly Gly Thr Cys Cys Ala Cys Gly Thr Ala Thr Gly Gly
                485                 490                 495

Ala Thr Cys Cys Thr Gly Gly Cys Cys Gly Gly Cys Cys Thr Cys Thr
                500                 505                 510

Gly Gly Cys Thr Gly Gly Cys Cys Gly Thr Gly Cys Cys Gly Gly
        515                 520                 525

Gly Cys Gly Cys Cys Cys Cys Thr Cys Gly Cys Cys Thr Thr Cys
        530                 535                 540

Thr Cys Gly Gly Ala Cys Gly Cys Gly Gly Gly Cys Cys Cys Cys
545                 550                 555                 560

Ala Cys Gly Thr Gly Cys Ala Cys Thr Ala Cys Gly Gly Cys Thr Gly
                565                 570                 575

Gly Gly Gly Cys Gly Ala Cys Cys Cys Ala Thr Cys Cys Gly Cys
        580                 585                 590

Cys Thr Gly Cys Gly Gly Cys Ala Cys Cys Thr Gly Thr Ala Cys Ala
        595                 600                 605

Cys Cys Thr Cys Cys Gly Gly Cys Cys Cys Cys Ala Cys Gly Gly
        610                 615                 620

Gly Cys Thr Cys Thr Cys Cys Ala Gly Cys Thr Gly Cys Thr Thr Cys
625                 630                 635                 640

Cys Thr Gly Cys Gly Cys Ala Thr Cys Cys Gly Thr Gly Cys Cys Gly
                645                 650                 655

Ala Cys Gly Gly Cys Gly Thr Cys Gly Thr Gly Gly Ala Cys Thr Gly
                660                 665                 670

Cys Gly Cys Gly Cys Gly Gly Gly Cys Cys Ala Gly Ala Gly Cys
        675                 680                 685

Gly Cys Gly Cys Ala Cys Ala Gly Thr Thr Thr Gly Cys Thr Gly Gly
        690                 695                 700

Ala Gly Ala Thr Cys Ala Ala Gly Gly Cys Ala Gly Thr Cys Gly Cys
705                 710                 715                 720

Thr Cys Thr Gly Cys Gly Gly Ala Cys Cys Gly Thr Gly Gly Cys Cys
                725                 730                 735

Ala Thr Cys Ala Ala Gly Gly Gly Cys Gly Thr Cys Ala Cys Cys Ala
                740                 745                 750

Gly Cys Gly Thr Gly Cys Gly Gly Thr Ala Cys Cys Thr Cys Thr Gly
        755                 760                 765

Cys Ala Thr Gly Gly Gly Cys Gly Cys Cys Gly Ala Cys Gly Gly Cys
770                 775                 780

Ala Ala Gly Ala Thr Gly Cys Ala Gly Gly Gly Cys Thr Gly Cys
785                 790                 795                 800

Thr Thr Cys Ala Gly Thr Ala Cys Thr Cys Gly Gly Ala Gly Gly Ala
                805                 810                 815

Ala Gly Ala Cys Thr Gly Thr Gly Cys Thr Thr Cys Gly Ala Gly
        820                 825                 830

Gly Ala Gly Gly Ala Gly Ala Thr Cys Cys Cys Cys Cys Ala Gly
        835                 840                 845

Ala Thr Gly Gly Cys Thr Ala Cys Ala Ala Thr Gly Thr Gly Thr Ala
850                 855                 860
```

Cys Cys Gly Ala Thr Cys Cys Gly Ala Ala Gly Ala Cys
865                 870                 875                 880

Cys Gly Cys Cys Thr Cys Cys Gly Gly Thr Cys Thr Cys Cys
                    885                 890                 895

Thr Gly Ala Gly Cys Ala Gly Thr Gly Cys Cys Ala Ala Cys Ala
            900                 905                 910

Gly Cys Gly Gly Cys Ala Gly Cys Thr Gly Thr Ala Cys Ala Ala Gly
        915                 920                 925

Ala Ala Cys Ala Gly Ala Gly Gly Cys Thr Thr Cys Thr Thr Cys
        930                 935                 940

Cys Ala Cys Thr Cys Thr Cys Thr Cys Ala Thr Thr Thr Cys Cys Thr
945                 950                 955                 960

Gly Cys Cys Cys Ala Thr Gly Cys Thr Gly Cys Cys Ala Thr Gly
            965                 970                 975

Gly Thr Cys Cys Cys Ala Gly Ala Gly Gly Ala Gly Cys Cys Thr Gly
            980                 985                 990

Ala Gly Gly Ala Cys Cys Thr Cys Ala Gly Gly Gly Gly Cys Cys Ala
            995                 1000                1005

Cys Thr Thr Gly Gly Ala Ala Thr Cys Thr Gly Ala Cys Ala Thr
1010                1015                1020

Gly Thr Thr Cys Thr Cys Thr Thr Cys Gly Cys Cys Cys Cys Thr
1025                1030                1035

Gly Gly Ala Gly Ala Cys Cys Gly Ala Cys Ala Gly Cys Ala Thr
1040                1045                1050

Gly Gly Ala Cys Cys Cys Ala Thr Thr Gly Gly Gly Cys Thr
1055                1060                1065

Thr Gly Thr Cys Ala Cys Cys Gly Gly Ala Cys Thr Gly Gly Ala
1070                1075                1080

Gly Gly Cys Cys Gly Thr Gly Ala Gly Gly Ala Gly Thr Cys Cys
1085                1090                1095

Cys Ala Gly Cys Thr Thr Gly Ala Gly Ala Ala Gly Thr Ala
1100                1105                1110

Ala Cys Thr Gly Ala Gly Ala Cys Cys Ala Thr Gly Cys Cys Cys
1115                1120                1125

Gly Gly Gly Cys Cys Thr Cys Thr Thr Cys Ala Cys Thr Gly Cys
1130                1135                1140

Thr Gly Cys Cys Ala Gly Gly Gly Cys Thr Gly Thr Gly Gly
1145                1150                1155

Thr Ala Cys Cys Thr Gly Cys Ala Gly Cys Gly Thr Gly Gly Gly
1160                1165                1170

Gly Gly Ala Cys Gly Thr Gly Cys Thr Cys Thr Ala Cys Ala
1175                1180                1185

Ala Gly Ala Ala Cys Ala Gly Thr Cys Cys Thr Gly Ala Gly Thr
1190                1195                1200

Cys Cys Ala Cys Gly Thr Cys Thr Gly Thr Thr Ala Gly
1205                1210                1215

Cys Thr Thr Thr Ala Gly Gly Ala Ala Gly Ala Ala Ala Cys Ala
1220                1225                1230

Thr Cys Thr Ala Gly Ala Ala Gly Thr Gly Thr Ala Cys Ala
1235                1240                1245

Thr Ala Thr Thr Cys Ala Gly Ala Gly Thr Thr Thr Cys Cys
1250                1255                1260

Ala Thr Thr Gly Gly Cys Ala Gly Thr Gly Cys Cys Ala Gly Thr

-continued

```
    1265                1270                1275

Thr Thr  Cys Thr Ala Gly Cys  Cys Ala Ala Thr Ala  Gly Ala Cys
    1280                1285                1290

Thr Thr  Gly Thr Cys Thr Gly  Ala Thr Cys Ala Thr  Ala Ala Cys
    1295                1300                1305

Ala Thr  Thr Gly Thr Ala Ala  Gly Cys Cys Thr Gly  Thr Ala Gly
    1310                1315                1320

Cys Thr  Thr Gly Cys Cys Cys  Ala Gly Cys Thr Gly  Cys Thr Gly
    1325                1330                1335

Cys Cys  Thr Gly Gly Gly Cys  Cys Cys Cys Cys Ala  Thr Thr Cys
    1340                1345                1350

Thr Gly  Cys Thr Cys Cys Cys  Thr Cys Gly Ala Gly  Gly Thr Thr
    1355                1360                1365

Gly Cys  Thr Gly Gly Ala Cys  Ala Ala Gly Cys Thr  Gly Cys Thr
    1370                1375                1380

Gly Cys  Ala Cys Thr Gly Thr  Cys Thr Cys Ala Gly  Thr Thr Cys
    1385                1390                1395

Thr Gly  Cys Thr Thr Gly Ala  Ala Thr Ala Cys Cys  Thr Cys Cys
    1400                1405                1410

Ala Thr  Cys Gly Ala Thr Gly  Gly Gly Gly Ala Ala  Cys Thr Cys
    1415                1420                1425

Ala Cys  Thr Thr Cys Cys Thr  Thr Thr Gly Gly Ala  Ala Ala Ala
    1430                1435                1440

Ala Thr  Thr Cys Thr Thr Ala  Thr Gly Thr Cys Ala  Ala Gly Cys
    1445                1450                1455

Thr Gly  Ala Ala Ala Thr Thr  Cys Thr Cys Thr Ala  Ala Thr Thr
    1460                1465                1470

Thr Thr  Thr Thr Cys Thr Cys  Ala Thr Cys Ala Cys  Thr Thr Cys
    1475                1480                1485

Cys Cys  Cys Ala Gly Gly Ala  Gly Cys Ala Gly Cys  Cys Ala Gly
    1490                1495                1500

Ala Ala  Gly Ala Cys Ala Gly  Gly Cys Ala Gly Thr  Ala Gly Thr
    1505                1510                1515

Thr Thr  Thr Ala Ala Thr Thr  Thr Cys Ala Gly Gly  Ala Ala Cys
    1520                1525                1530

Ala Gly  Gly Thr Gly Ala Thr  Cys Cys Ala Cys Thr  Cys Thr Gly
    1535                1540                1545

Thr Ala  Ala Ala Ala Cys Ala  Gly Cys Ala Gly Gly  Thr Ala Ala
    1550                1555                1560

Ala Thr  Thr Thr Cys Ala Cys  Thr Cys Ala Ala Cys  Cys Cys Cys
    1565                1570                1575

Ala Thr  Gly Thr Gly Gly Gly  Ala Ala Thr Thr Gly  Ala Thr Cys
    1580                1585                1590

Thr Ala  Thr Ala Thr Cys Thr  Cys Thr Ala Cys Thr  Thr Cys Cys
    1595                1600                1605

Ala Gly  Gly Gly Ala Cys Cys  Ala Thr Thr Thr Gly  Cys Cys Cys
    1610                1615                1620

Thr Thr  Cys Cys Cys Ala Ala  Ala Thr Cys Cys Cys  Thr Cys Cys
    1625                1630                1635

Ala Gly  Gly Cys Cys Ala Gly  Ala Ala Cys Thr Gly  Ala Cys Thr
    1640                1645                1650

Gly Gly  Ala Gly Cys Ala Gly  Gly Cys Ala Thr Gly  Gly Cys Cys
    1655                1660                1665
```

```
Cys Ala Cys Cys Ala Gly Gly Cys Thr Thr Cys Ala Gly Gly Ala
    1670                1675                1680
Gly Thr Ala Gly Gly Gly Ala Ala Gly Cys Cys Thr Gly Gly
    1685                1690                1695
Ala Gly Cys Cys Cys Cys Ala Cys Thr Cys Cys Ala Gly Cys Cys
    1700                1705                1710
Cys Thr Gly Gly Gly Ala Cys Ala Ala Cys Thr Gly Ala Gly
    1715                1720                1725
Ala Ala Thr Thr Cys Cys Cys Cys Thr Gly Ala Gly Gly Cys
    1730                1735                1740
Cys Ala Gly Thr Thr Cys Thr Gly Thr Cys Ala Thr Gly Gly Ala
    1745                1750                1755
Thr Gly Cys Thr Gly Thr Cys Cys Thr Gly Ala Gly Ala Ala Thr
    1760                1765                1770
Ala Ala Cys Thr Thr Gly Cys Thr Gly Thr Cys Cys Gly Gly
    1775                1780                1785
Thr Gly Thr Cys Ala Cys Cys Thr Gly Cys Thr Thr Cys Cys Ala
    1790                1795                1800
Thr Cys Thr Cys Cys Cys Ala Gly Cys Cys Ala Cys Cys Ala
    1805                1810                1815
Gly Cys Cys Cys Thr Cys Thr Gly Cys Cys Ala Cys Cys Thr
    1820                1825                1830
Cys Ala Cys Ala Thr Gly Cys Cys Thr Cys Cys Cys Ala Thr
    1835                1840                1845
Gly Gly Ala Thr Thr Gly Gly Gly Cys Cys Thr Cys Cys Cys
    1850                1855                1860
Ala Gly Gly Cys Cys Cys Cys Cys Ala Cys Thr Thr Ala
    1865                1870                1875
Thr Gly Thr Cys Ala Ala Cys Cys Thr Gly Cys Ala Cys Thr Thr
    1880                1885                1890
Cys Thr Thr Gly Thr Thr Cys Ala Ala Ala Ala Thr Cys Ala
    1895                1900                1905
Gly Gly Ala Ala Ala Ala Gly Ala Ala Ala Gly Ala Thr Thr
    1910                1915                1920
Thr Gly Ala Ala Gly Ala Cys Cys Cys Ala Ala Gly Thr Cys
    1925                1930                1935
Thr Thr Gly Thr Cys Ala Ala Thr Ala Ala Cys Thr Thr Gly Cys
    1940                1945                1950
Thr Gly Thr Gly Thr Gly Gly Ala Ala Gly Cys Ala Gly Cys Gly
    1955                1960                1965
Gly Gly Gly Gly Ala Ala Gly Ala Cys Cys Thr Ala Gly Ala Ala
    1970                1975                1980
Cys Cys Cys Thr Thr Cys Cys Cys Ala Gly Cys Ala Cys
    1985                1990                1995
Thr Thr Gly Gly Thr Thr Thr Cys Ala Ala Cys Ala Thr
    2000                2005                2010
Gly Ala Thr Ala Thr Thr Ala Thr Gly Ala Gly Thr Ala Ala
    2015                2020                2025
Thr Thr Thr Ala Thr Thr Thr Gly Ala Thr Ala Thr Gly Thr
    2030                2035                2040
Ala Cys Ala Thr Cys Thr Cys Thr Thr Ala Thr Thr Thr Cys
    2045                2050                2055
Thr Thr Ala Cys Ala Thr Thr Ala Thr Thr Ala Thr Gly Cys
    2060                2065                2070
```

```
Cys Cys Cys Cys Ala Ala Thr Thr Ala Thr Ala Thr Thr Thr
    2075            2080            2085

Ala Thr Gly Thr Ala Thr Gly Thr Ala Ala Gly Thr Gly Ala Gly
    2090            2095            2100

Gly Thr Thr Thr Gly Thr Thr Thr Thr Gly Thr Ala Thr Ala Thr
    2105            2110            2115

Thr Ala Ala Ala Ala Thr Gly Gly Ala Gly Thr Thr Thr Gly Thr
    2120            2125            2130

Thr Thr Gly Thr Ala Ala Ala Ala Ala Ala Ala Ala Ala Ala
    2135            2140            2145

Ala Ala Ala Ala Ala Ala Ala Ala Ala
    2150            2155

<210> SEQ ID NO 31
<211> LENGTH: 216
<212> TYPE: PRT
<213> ORGANISM: Homo Sapiens

<400> SEQUENCE: 31

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                    20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
    115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
    195                 200                 205

Val Arg Ser Pro Ser Phe Glu Lys
    210                 215

<210> SEQ ID NO 32
<211> LENGTH: 940
<212> TYPE: PRT
<213> ORGANISM: Homo Sapiens

<400> SEQUENCE: 32

Cys Thr Gly Thr Cys Ala Gly Cys Thr Gly Ala Gly Gly Ala Thr Cys
1               5                   10                  15
```

-continued

```
Cys Ala Gly Cys Cys Gly Ala Ala Ala Gly Ala Gly Gly Ala Gly Cys
            20                  25                  30

Cys Ala Gly Gly Cys Ala Cys Thr Cys Ala Gly Gly Cys Cys Ala Cys
        35                  40                  45

Cys Thr Gly Ala Gly Thr Cys Thr Ala Cys Thr Cys Ala Cys Cys Thr
    50                  55                  60

Gly Gly Ala Cys Ala Ala Cys Thr Gly Gly Ala Ala Thr Cys Thr Gly
65                  70                  75                  80

Gly Cys Ala Cys Cys Ala Ala Thr Thr Cys Thr Ala Ala Ala Cys Cys
                85                  90                  95

Ala Cys Thr Cys Ala Gly Cys Thr Thr Cys Thr Cys Cys Gly Ala Gly
            100                 105                 110

Cys Thr Cys Ala Cys Ala Cys Cys Cys Cys Gly Gly Ala Gly Ala Thr
        115                 120                 125

Cys Ala Cys Cys Thr Gly Ala Gly Gly Ala Cys Cys Cys Gly Ala Gly
    130                 135                 140

Cys Cys Ala Thr Thr Gly Ala Thr Gly Gly Ala Cys Thr Cys Gly Gly
145                 150                 155                 160

Ala Cys Gly Ala Gly Ala Cys Cys Gly Gly Gly Thr Thr Cys Gly Ala
                165                 170                 175

Gly Cys Ala Cys Thr Cys Ala Gly Gly Ala Cys Thr Gly Thr Gly Gly
            180                 185                 190

Gly Thr Thr Thr Cys Thr Gly Thr Gly Cys Thr Gly Gly Cys Thr Gly
        195                 200                 205

Gly Thr Cys Thr Thr Cys Thr Gly Cys Thr Gly Gly Gly Ala Gly Cys
    210                 215                 220

Cys Thr Gly Cys Cys Ala Gly Gly Cys Ala Cys Ala Cys Cys Cys Cys
225                 230                 235                 240

Ala Thr Cys Cys Cys Thr Gly Ala Cys Thr Cys Cys Ala Gly Thr Cys
                245                 250                 255

Cys Thr Cys Thr Cys Cys Thr Gly Cys Ala Ala Thr Thr Cys Gly Gly
            260                 265                 270

Gly Gly Gly Cys Cys Ala Ala Gly Thr Cys Cys Gly Gly Cys Ala Gly
        275                 280                 285

Cys Gly Gly Thr Ala Cys Cys Thr Cys Thr Ala Cys Ala Cys Ala Gly
    290                 295                 300

Ala Thr Gly Ala Thr Gly Cys Cys Cys Ala Gly Cys Ala Gly Ala Cys
305                 310                 315                 320

Ala Gly Ala Ala Gly Cys Cys Cys Ala Cys Cys Thr Gly Gly Ala Gly
                325                 330                 335

Ala Thr Cys Ala Gly Gly Gly Ala Gly Gly Ala Thr Gly Gly Gly Ala
            340                 345                 350

Cys Gly Gly Thr Gly Gly Gly Gly Gly Gly Cys Gly Cys Thr Gly Cys
        355                 360                 365

Thr Gly Ala Cys Cys Ala Gly Ala Gly Cys Cys Cys Gly Ala Ala
    370                 375                 380

Ala Gly Thr Cys Thr Cys Cys Thr Gly Cys Ala Gly Cys Thr Gly Ala
385                 390                 395                 400

Ala Ala Gly Cys Cys Thr Thr Gly Ala Ala Gly Cys Cys Gly Gly Gly
                405                 410                 415

Ala Gly Thr Thr Ala Thr Thr Cys Ala Ala Ala Thr Cys Thr Thr Gly
            420                 425                 430

Gly Gly Ala Gly Thr Cys Ala Ala Gly Ala Cys Ala Thr Cys Cys Ala
        435                 440                 445
```

```
Gly Gly Thr Thr Cys Cys Thr Gly Thr Gly Cys Cys Ala Cys Gly
        450             455             460
Gly Cys Cys Ala Gly Ala Thr Gly Gly Gly Cys Cys Cys Thr Gly
465             470             475             480
Thr Ala Thr Gly Gly Ala Thr Cys Gly Cys Thr Cys Cys Ala Cys Thr
                485             490             495
Thr Thr Gly Ala Cys Cys Cys Thr Gly Ala Gly Gly Cys Cys Thr Gly
            500             505             510
Cys Ala Gly Cys Thr Thr Cys Cys Gly Gly Gly Ala Gly Cys Thr Gly
            515             520             525
Cys Thr Thr Cys Thr Thr Gly Ala Gly Gly Ala Cys Gly Gly Ala Thr
        530             535             540
Ala Cys Ala Ala Thr Gly Thr Thr Thr Ala Cys Cys Ala Gly Thr Cys
545             550             555             560
Cys Gly Ala Ala Gly Cys Cys Ala Cys Gly Gly Cys Cys Thr Cys
            565             570             575
Cys Cys Gly Cys Thr Gly Cys Ala Cys Cys Thr Gly Cys Cys Ala Gly
            580             585             590
Gly Gly Ala Ala Cys Ala Ala Gly Thr Cys Cys Cys Ala Cys Ala
        595             600             605
Cys Cys Gly Gly Gly Ala Cys Cys Cys Thr Gly Cys Ala Cys Cys
610             615             620
Cys Gly Ala Gly Gly Ala Cys Ala Gly Cys Thr Cys Gly Cys Thr
625             630             635             640
Thr Cys Cys Thr Gly Cys Cys Ala Cys Thr Ala Cys Cys Ala Gly Gly
            645             650             655
Cys Cys Thr Gly Cys Cys Cys Cys Cys Gly Cys Ala Cys Thr Cys
            660             665             670
Cys Cys Gly Gly Ala Gly Cys Cys Ala Cys Cys Gly Gly Ala Ala
            675             680             685
Thr Cys Cys Thr Gly Gly Cys Cys Cys Cys Cys Ala Gly Cys Cys
            690             695             700
Cys Cys Cys Cys Gly Ala Thr Gly Thr Gly Gly Cys Thr Cys Cys
705             710             715             720
Thr Cys Gly Gly Ala Cys Cys Cys Thr Cys Thr Gly Ala Gly Cys Ala
                725             730             735
Thr Gly Gly Thr Gly Gly Gly Ala Cys Cys Thr Thr Cys Cys Cys Ala
            740             745             750
Gly Gly Gly Cys Cys Gly Ala Ala Gly Cys Cys Cys Ala Gly Cys
        755             760             765
Thr Ala Cys Gly Cys Thr Thr Cys Cys Thr Gly Ala Ala Gly Cys Cys
        770             775             780
Ala Gly Ala Gly Gly Cys Thr Gly Thr Thr Ala Cys Thr Ala Thr
785             790             795             800
Gly Ala Cys Ala Thr Cys Thr Cys Cys Thr Cys Thr Thr Ala Thr
        805             810             815
Thr Thr Ala Thr Thr Ala Gly Gly Thr Thr Ala Thr Thr Ala Thr
            820             825             830
Cys Thr Thr Ala Thr Thr Thr Ala Thr Thr Thr Thr Thr Thr Ala
        835             840             845
Thr Thr Thr Thr Thr Cys Thr Thr Ala Cys Thr Gly Ala Gly Ala
        850             855             860
Thr Ala Ala Thr Ala Ala Ala Gly Ala Gly Thr Thr Cys Cys Ala Gly
```

```
                865                 870                 875                 880
Ala Gly Gly Ala Gly Ala Ala Ala Ala Ala Ala Ala Ala Ala Ala Ala
                    885                 890                 895

Ala Ala Ala Ala Ala Ala Ala Ala Ala Ala Ala Ala Ala Ala Ala Ala
            900                 905                 910

Ala Ala Ala Ala Ala Ala Ala Ala Ala Ala Ala Ala Ala Ala Ala Ala
        915                 920                 925

Ala Ala Ala Ala Ala Ala Ala Ala Ala Ala
    930                 935                 940

<210> SEQ ID NO 33
<211> LENGTH: 209
<212> TYPE: PRT
<213> ORGANISM: Homo Sapiens

<400> SEQUENCE: 33

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 34
<211> LENGTH: 3018
<212> TYPE: PRT
<213> ORGANISM: Homo Sapiens

<400> SEQUENCE: 34

Cys Gly Gly Cys Ala Ala Ala Ala Gly Gly Ala Gly Gly Gly Gly Ala
1               5                   10                  15

Ala Thr Cys Cys Ala Gly Thr Cys Thr Ala Gly Gly Ala Thr Cys Cys
            20                  25                  30

Thr Cys Ala Cys Ala Cys Cys Ala Gly Cys Thr Ala Cys Thr Thr Gly
        35                  40                  45
```

```
Cys Ala Ala Gly Gly Ala Gly Ala Gly Ala Ala Ala
     50                  55                  60
Gly Gly Cys Cys Ala Gly Thr Ala Ala Gly Gly Cys Cys Thr Gly Gly
 65              70                  75                  80
Gly Cys Cys Ala Gly Gly Ala Gly Ala Gly Thr Cys Cys Cys Gly Ala
                 85                  90                  95
Cys Ala Gly Gly Ala Gly Thr Gly Thr Cys Ala Gly Gly Thr Thr Thr
                100                 105                 110
Cys Ala Ala Thr Cys Thr Cys Ala Gly Cys Ala Cys Cys Ala Gly Cys
             115                 120                 125
Cys Ala Cys Thr Cys Ala Gly Ala Gly Cys Ala Gly Gly Gly Cys Ala
         130                 135                 140
Cys Gly Ala Thr Gly Thr Thr Gly Gly Gly Gly Cys Cys Cys Gly
145                 150                 155                 160
Cys Cys Thr Cys Ala Gly Gly Cys Thr Cys Thr Gly Gly Gly Thr Cys
             165                 170                 175
Thr Gly Thr Gly Cys Cys Thr Cys Thr Gly Cys Ala Gly Cys Cys Gly
         180                 185                 190
Thr Cys Thr Gly Cys Ala Gly Cys Ala Thr Gly Ala Gly Cys Gly Thr
         195                 200                 205
Cys Cys Thr Cys Ala Gly Ala Gly Cys Cys Thr Ala Thr Cys Cys Cys
         210                 215                 220
Ala Ala Thr Gly Cys Cys Thr Cys Cys Cys Ala Cys Thr Gly Cys
225                 230                 235                 240
Thr Cys Gly Gly Cys Thr Cys Cys Ala Gly Cys Thr Gly Gly Gly Gly
             245                 250                 255
Thr Gly Gly Cys Cys Thr Gly Ala Thr Cys Cys Ala Cys Cys Thr Gly
         260                 265                 270
Thr Ala Cys Ala Cys Ala Gly Cys Cys Ala Cys Ala Gly Cys Cys Ala
         275                 280                 285
Gly Gly Ala Ala Cys Ala Gly Cys Thr Ala Cys Cys Ala Cys Cys Thr
         290                 295                 300
Gly Cys Ala Gly Ala Thr Cys Ala Cys Ala Ala Gly Ala Ala Thr
305                 310                 315                 320
Gly Gly Cys Cys Ala Thr Gly Thr Gly Gly Ala Thr Gly Gly Cys Gly
             325                 330                 335
Cys Ala Cys Cys Cys Ala Thr Cys Ala Gly Ala Cys Cys Ala Thr
         340                 345                 350
Cys Thr Ala Cys Ala Gly Thr Gly Cys Cys Thr Gly Ala Thr Gly
         355                 360                 365
Ala Thr Cys Ala Gly Ala Thr Cys Ala Gly Ala Gly Gly Ala Thr Gly
         370                 375                 380
Cys Thr Gly Gly Cys Thr Thr Gly Thr Gly Gly Thr Gly Ala Thr
385                 390                 395                 400
Thr Ala Cys Ala Gly Gly Thr Gly Thr Gly Ala Thr Gly Ala Gly Cys
             405                 410                 415
Ala Gly Ala Ala Gly Ala Thr Ala Cys Cys Thr Cys Thr Gly Cys Ala
         420                 425                 430
Thr Gly Gly Ala Thr Thr Cys Ala Gly Ala Gly Gly Cys Ala Ala
         435                 440                 445
Cys Ala Thr Thr Thr Thr Gly Gly Ala Thr Cys Ala Cys Ala Cys
         450                 455                 460
Thr Ala Thr Thr Thr Cys Gly Ala Cys Cys Cys Gly Gly Ala Gly Ala
465                 470                 475                 480
```

-continued

```
Ala Cys Thr Gly Cys Ala Gly Gly Thr Cys Cys Ala Cys Ala
            485                 490                 495
Cys Cys Ala Gly Ala Cys Gly Cys Thr Gly Ala Ala Ala Cys
            500                 505                 510
Gly Gly Gly Thr Ala Cys Gly Ala Cys Gly Thr Cys Thr Ala Cys Cys
            515                 520                 525
Ala Cys Thr Cys Thr Cys Cys Thr Cys Ala Gly Thr Ala Thr Cys Ala
            530                 535                 540
Cys Thr Thr Cys Thr Gly Thr Cys Ala Gly Thr Cys Thr Gly
545                 550                 555                 560
Gly Gly Cys Cys Gly Gly Cys Gly Ala Ala Gly Ala Gly Ala Gly
                565                 570                 575
Cys Cys Thr Thr Cys Cys Thr Gly Cys Cys Ala Gly Gly Cys Ala Thr
            580                 585                 590
Gly Ala Ala Cys Cys Cys Ala Cys Cys Cys Cys Gly Thr Ala Cys
            595                 600                 605
Thr Cys Cys Cys Ala Gly Thr Thr Cys Thr Gly Thr Cys Cys Cys
610                 615                 620
Gly Gly Ala Gly Gly Ala Ala Cys Gly Ala Gly Ala Thr Cys Cys Cys
625                 630                 635                 640
Cys Cys Thr Ala Ala Thr Thr Cys Ala Cys Thr Thr Cys Ala Ala Cys
            645                 650                 655
Ala Cys Cys Cys Cys Ala Thr Ala Cys Cys Ala Cys Gly Gly Cys
            660                 665                 670
Gly Gly Cys Ala Cys Ala Cys Cys Gly Gly Ala Gly Cys Gly Cys
            675                 680                 685
Cys Gly Ala Gly Gly Ala Cys Gly Ala Cys Thr Cys Gly Gly Ala Gly
            690                 695                 700
Cys Gly Gly Gly Ala Cys Cys Cys Cys Thr Gly Ala Ala Cys Gly
705                 710                 715                 720
Thr Gly Cys Thr Gly Ala Ala Gly Cys Cys Cys Cys Gly Gly Gly Cys
            725                 730                 735
Cys Cys Gly Gly Ala Thr Gly Ala Cys Cys Cys Cys Gly Gly Cys Cys
            740                 745                 750
Cys Cys Gly Gly Cys Cys Thr Cys Cys Thr Gly Thr Thr Cys Ala Cys
            755                 760                 765
Ala Gly Gly Ala Gly Cys Thr Cys Cys Gly Ala Gly Cys Gly Cys
            770                 775                 780
Cys Gly Ala Gly Gly Ala Cys Ala Ala Cys Ala Gly Cys Cys Cys Gly
785                 790                 795                 800
Ala Thr Gly Gly Cys Cys Ala Gly Thr Gly Ala Cys Cys Cys Ala Thr
            805                 810                 815
Thr Ala Gly Gly Gly Gly Thr Gly Gly Thr Cys Ala Gly Gly Gly
            820                 825                 830
Cys Gly Gly Thr Cys Gly Ala Gly Thr Gly Ala Ala Cys Ala Cys Gly
            835                 840                 845
Cys Ala Cys Gly Cys Thr Gly Gly Gly Gly Ala Ala Cys Gly Gly
            850                 855                 860
Gly Cys Cys Cys Gly Gly Ala Ala Gly Cys Thr Gly Cys Cys Gly
865                 870                 875                 880
Cys Cys Cys Cys Thr Thr Cys Gly Cys Ala Ala Gly Thr Thr Cys
            885                 890                 895
Ala Thr Cys Thr Ala Gly Gly Gly Thr Cys Gly Cys Thr Gly Gly Ala
```

```
            900                 905                 910

Ala Gly Gly Gly Cys Ala Cys Cys Cys Thr Cys Thr Thr Thr Ala Ala
        915                 920                 925

Cys Cys Cys Ala Thr Cys Cys Cys Thr Cys Ala Gly Cys Ala Ala Ala
    930                 935                 940

Cys Gly Cys Ala Gly Cys Thr Cys Thr Thr Cys Cys Cys Ala Ala Gly
945                 950                 955                 960

Gly Ala Cys Cys Ala Gly Gly Thr Cys Cys Cys Thr Thr Gly Ala Cys
                965                 970                 975

Gly Thr Thr Cys Cys Gly Ala Gly Gly Ala Thr Gly Gly Gly Ala Ala
            980                 985                 990
Ala Gly Gly Thr Gly Ala Cys Ala  Gly Gly Gly Gly Cys  Ala Thr Gly
        995                 1000                1005

Thr Ala  Thr Gly Gly Ala Ala  Thr Thr Thr Gly Cys  Thr Gly Cys
    1010                1015                1020

Thr Thr  Cys Thr Cys Thr Gly  Gly Gly Gly Thr Cys  Cys Cys Thr
    1025                1030                1035

Thr Cys  Cys Ala Cys Ala Gly  Gly Ala Gly Gly Thr  Cys Cys Thr
    1040                1045                1050

Gly Thr  Gly Ala Gly Ala Ala  Cys Cys Ala Ala Cys  Cys Thr Thr
    1055                1060                1065
Thr Gly  Ala Gly Gly Cys Cys  Cys Ala Ala Gly Thr  Cys Ala Thr
    1070                1075                1080
Gly Gly  Gly Gly Thr Thr Thr  Cys Ala Cys Cys Gly  Cys Cys Thr
    1085                1090                1095

Thr Cys  Cys Thr Cys Ala Cys  Thr Cys Cys Ala Thr  Ala Thr Ala
    1100                1105                1110

Gly Ala  Ala Cys Ala Cys Cys  Thr Thr Thr Cys Cys  Cys Ala Ala
    1115                1120                1125

Thr Ala  Gly Gly Ala Ala Ala  Cys Cys Cys Cys Ala  Ala Cys Ala
    1130                1135                1140

Gly Gly  Thr Ala Ala Ala Cys  Thr Ala Gly Ala Ala  Ala Thr Thr
    1145                1150                1155

Thr Cys  Cys Cys Cys Thr Thr  Cys Ala Thr Gly Ala  Ala Gly Gly
    1160                1165                1170

Thr Ala  Gly Ala Gly Ala Gly  Ala Ala Gly Gly Gly  Gly Thr Cys
    1175                1180                1185

Thr Cys  Thr Cys Cys Cys Ala  Ala Cys Ala Thr Ala  Thr Thr Thr
    1190                1195                1200

Cys Thr  Cys Thr Thr Cys Cys  Thr Thr Gly Thr Gly  Cys Cys Thr
    1205                1210                1215

Cys Thr  Cys Cys Thr Cys Thr  Thr Thr Ala Thr Cys  Ala Cys Thr
    1220                1225                1230

Thr Thr  Thr Ala Ala Gly Cys  Ala Thr Ala Ala Ala  Ala Ala Ala
    1235                1240                1245

Ala Ala  Ala Ala Ala Ala Ala  Ala Ala Ala Ala Ala  Ala Ala Ala
    1250                1255                1260

Ala Ala  Ala Ala Ala Ala Ala  Ala Ala Ala Ala Gly  Cys Ala Gly
    1265                1270                1275

Thr Gly  Gly Gly Thr Thr Cys  Cys Thr Gly Ala Gly  Cys Thr Cys
    1280                1285                1290

Ala Ala  Gly Ala Cys Thr Thr  Thr Gly Ala Ala Gly  Gly Thr Gly
    1295                1300                1305
```

```
Thr Ala Gly Gly Gly Ala Ala Gly Ala Gly Ala Ala Ala Thr
1310                1315                1320

Cys Gly Gly Ala Gly Ala Thr Cys Cys Cys Ala Gly Ala Ala Gly
1325                1330                1335

Cys Thr Thr Cys Thr Cys Cys Ala Cys Thr Gly Cys Cys Cys Thr
1340                1345                1350

Ala Thr Gly Cys Ala Thr Thr Ala Thr Gly Thr Thr Ala Gly
1355                1360                1365

Ala Thr Gly Cys Cys Cys Gly Ala Thr Cys Cys Cys Ala Cys
1370                1375                1380

Thr Gly Gly Cys Ala Thr Thr Thr Gly Ala Gly Thr Gly Thr Gly
1385                1390                1395

Cys Ala Ala Ala Cys Cys Thr Thr Gly Ala Cys Ala Thr Thr Ala
1400                1405                1410

Ala Cys Ala Gly Cys Thr Gly Ala Ala Thr Gly Gly Gly Gly Cys
1415                1420                1425

Ala Ala Gly Thr Thr Gly Ala Thr Gly Ala Ala Ala Ala Cys Ala
1430                1435                1440

Cys Thr Ala Cys Thr Thr Thr Cys Ala Ala Gly Cys Cys Thr Thr
1445                1450                1455

Cys Gly Thr Thr Cys Thr Thr Cys Cys Thr Thr Gly Ala Gly Cys
1460                1465                1470

Ala Thr Cys Thr Cys Thr Gly Gly Gly Gly Ala Ala Gly Ala Gly
1475                1480                1485

Cys Thr Gly Thr Cys Ala Ala Ala Ala Gly Ala Cys Thr Gly Gly
1490                1495                1500

Thr Gly Gly Thr Ala Gly Gly Cys Thr Gly Gly Thr Gly Ala Ala
1505                1510                1515

Ala Ala Cys Thr Thr Gly Ala Cys Ala Gly Cys Thr Ala Gly Ala
1520                1525                1530

Cys Thr Thr Gly Ala Thr Gly Cys Thr Thr Gly Cys Thr Gly Ala
1535                1540                1545

Ala Ala Thr Gly Ala Gly Gly Cys Ala Gly Gly Ala Ala Thr Cys
1550                1555                1560

Ala Thr Ala Ala Thr Ala Gly Ala Ala Ala Ala Cys Thr Cys Ala
1565                1570                1575

Gly Cys Cys Thr Cys Cys Thr Ala Cys Ala Gly Gly Gly Thr
1580                1585                1590

Gly Ala Gly Cys Ala Cys Cys Thr Thr Cys Thr Gly Thr Cys Thr
1595                1600                1605

Cys Gly Cys Thr Gly Thr Cys Thr Cys Cys Cys Thr Cys Thr Gly
1610                1615                1620

Thr Gly Cys Ala Gly Cys Cys Ala Cys Ala Gly Cys Cys Ala Gly
1625                1630                1635

Ala Gly Gly Gly Cys Cys Cys Ala Gly Ala Ala Thr Gly Gly Cys
1640                1645                1650

Cys Cys Cys Ala Cys Thr Cys Thr Gly Thr Thr Cys Cys Cys Ala
1655                1660                1665

Ala Gly Cys Ala Gly Thr Thr Cys Ala Thr Gly Ala Thr Ala Cys
1670                1675                1680

Ala Gly Cys Cys Thr Cys Ala Cys Cys Thr Thr Thr Gly Gly
1685                1690                1695

Cys Cys Cys Cys Ala Thr Cys Thr Cys Thr Gly Gly Thr Thr Thr
1700                1705                1710
```

```
Thr Thr Gly Ala Ala Ala Thr Thr Thr Gly Gly Thr Cys Thr
    1715            1720            1725

Ala Ala Gly Gly Ala Gly Ala Thr Ala Ala Ala Thr Ala Gly Cys Thr
    1730            1735            1740

Thr Thr Thr Ala Cys Ala Cys Thr Gly Gly Cys Thr Cys Ala Cys
    1745            1750            1755

Gly Ala Ala Ala Ala Thr Cys Thr Gly Cys Cys Cys Thr Gly Cys
    1760            1765            1770

Thr Ala Gly Ala Ala Thr Thr Thr Gly Cys Thr Thr Thr Thr Cys
    1775            1780            1785

Ala Ala Ala Ala Thr Gly Gly Ala Ala Ala Thr Ala Ala Ala Thr
    1790            1795            1800

Thr Cys Cys Ala Ala Cys Thr Cys Thr Cys Cys Thr Ala Ala Gly
    1805            1810            1815

Ala Gly Gly Cys Ala Thr Thr Thr Ala Ala Thr Ala Ala Ala Gly
    1820            1825            1830

Gly Cys Thr Cys Thr Ala Cys Thr Thr Cys Cys Ala Gly Gly Thr
    1835            1840            1845

Thr Gly Ala Gly Thr Ala Gly Gly Ala Ala Thr Cys Cys Ala Thr
    1850            1855            1860

Thr Cys Thr Gly Ala Ala Cys Ala Ala Ala Cys Thr Ala Cys Ala
    1865            1870            1875

Ala Ala Ala Ala Thr Gly Thr Gly Ala Cys Thr Gly Gly Gly Ala
    1880            1885            1890

Ala Gly Gly Gly Gly Gly Cys Thr Thr Thr Gly Ala Gly Ala Gly
    1895            1900            1905

Ala Cys Thr Gly Gly Gly Ala Cys Thr Gly Cys Thr Cys Thr Gly
    1910            1915            1920

Gly Gly Thr Thr Ala Gly Gly Thr Thr Thr Thr Cys Thr Gly Thr
    1925            1930            1935

Gly Gly Ala Cys Thr Gly Ala Ala Ala Ala Ala Thr Cys Gly Thr
    1940            1945            1950

Gly Thr Cys Cys Thr Thr Thr Thr Cys Thr Cys Thr Ala Ala Ala
    1955            1960            1965

Thr Gly Ala Ala Gly Thr Gly Gly Cys Ala Thr Cys Ala Ala Gly
    1970            1975            1980

Gly Ala Cys Thr Cys Ala Gly Gly Gly Gly Gly Ala Ala Ala Gly
    1985            1990            1995

Ala Ala Ala Thr Cys Ala Gly Gly Gly Gly Ala Cys Ala Thr Gly
    2000            2005            2010

Thr Thr Ala Thr Ala Gly Ala Ala Gly Thr Thr Ala Thr Gly Ala
    2015            2020            2025

Ala Ala Ala Gly Ala Cys Ala Ala Cys Cys Ala Cys Ala Thr Gly
    2030            2035            2040

Gly Thr Cys Ala Gly Gly Cys Thr Cys Thr Thr Gly Thr Cys Thr
    2045            2050            2055

Gly Thr Gly Gly Thr Cys Thr Cys Thr Ala Gly Gly Gly Cys Thr
    2060            2065            2070

Cys Thr Gly Cys Ala Gly Cys Ala Gly Cys Ala Gly Thr Gly Gly
    2075            2080            2085

Cys Thr Cys Thr Thr Cys Gly Ala Thr Thr Ala Gly Thr Thr Ala
    2090            2095            2100

Ala Ala Ala Cys Thr Cys Thr Cys Cys Thr Ala Gly Gly Cys Thr
```

2105 2110 2115

Gly Ala Cys Ala Cys Ala Thr Cys Thr Gly Gly Gly Thr Cys Thr
2120 2125 2130

Cys Ala Ala Thr Cys Cys Cys Cys Thr Thr Gly Gly Ala Ala Ala
2135 2140 2145

Thr Thr Cys Thr Thr Gly Gly Thr Gly Cys Ala Thr Thr Ala Ala
2150 2155 2160

Ala Thr Gly Ala Ala Gly Cys Cys Thr Thr Ala Cys Cys Cys Cys
2165 2170 2175

Ala Thr Thr Ala Cys Thr Gly Cys Gly Gly Thr Thr Cys Thr Thr
2180 2185 2190

Cys Cys Thr Gly Thr Ala Ala Gly Gly Gly Gly Gly Cys Thr Cys
2195 2200 2205

Cys Ala Thr Thr Thr Thr Cys Cys Thr Cys Cys Cys Thr Cys Thr
2210 2215 2220

Cys Thr Thr Thr Ala Ala Ala Thr Gly Ala Cys Cys Ala Cys Cys
2225 2230 2235

Thr Ala Ala Ala Gly Gly Ala Cys Ala Gly Thr Ala Thr Ala Thr
2240 2245 2250

Thr Ala Ala Cys Ala Ala Gly Cys Ala Ala Ala Gly Thr Cys Gly
2255 2260 2265

Ala Thr Thr Cys Ala Ala Cys Ala Ala Cys Ala Gly Cys Thr Thr
2270 2275 2280

Cys Thr Thr Cys Cys Cys Ala Gly Thr Cys Ala Cys Thr Thr Thr
2285 2290 2295

Thr Thr Thr Thr Thr Thr Thr Cys Thr Cys Ala Cys Thr Gly Cys
2300 2305 2310

Cys Ala Thr Cys Ala Cys Ala Thr Ala Cys Thr Ala Ala Cys Cys
2315 2320 2325

Thr Thr Ala Thr Ala Cys Thr Thr Thr Gly Ala Thr Cys Thr Ala
2330 2335 2340

Thr Thr Cys Thr Thr Thr Thr Thr Gly Gly Thr Thr Ala Thr Gly
2345 2350 2355

Ala Gly Ala Gly Ala Ala Ala Thr Gly Thr Thr Gly Gly Gly Cys
2360 2365 2370

Ala Ala Cys Thr Gly Thr Thr Thr Thr Thr Ala Cys Cys Thr Gly
2375 2380 2385

Ala Thr Gly Gly Thr Thr Thr Thr Ala Ala Gly Cys Thr Gly Ala
2390 2395 2400

Ala Cys Thr Thr Gly Ala Ala Gly Gly Ala Cys Thr Gly Gly Thr
2405 2410 2415

Thr Cys Cys Thr Ala Thr Thr Cys Thr Gly Ala Ala Ala Cys Ala
2420 2425 2430

Gly Thr Ala Ala Ala Ala Cys Thr Ala Thr Gly Thr Ala Thr Ala
2435 2440 2445

Ala Thr Ala Gly Thr Ala Thr Ala Thr Ala Gly Cys Cys Ala Thr
2450 2455 2460

Gly Cys Ala Thr Gly Gly Cys Ala Ala Ala Thr Ala Thr Thr Thr
2465 2470 2475

Thr Ala Ala Thr Ala Thr Thr Thr Cys Thr Gly Thr Thr Thr Thr
2480 2485 2490

Cys Ala Thr Thr Thr Cys Cys Thr Gly Thr Thr Gly Gly Ala Ala
2495 2500 2505

-continued

```
Ala Thr Ala Thr Thr Ala Thr Cys Cys Thr Gly Cys Ala Thr Ala
2510                2515                2520
Ala Thr Ala Gly Cys Thr Ala Thr Thr Gly Gly Ala Gly Gly Cys
2525                2530                2535
Thr Cys Cys Thr Cys Ala Gly Thr Gly Ala Ala Ala Gly Ala Thr
2540                2545                2550
Cys Cys Cys Ala Ala Ala Gly Gly Ala Thr Thr Thr Thr Thr Gly
2555                2560                2565
Gly Thr Gly Gly Ala Ala Ala Ala Cys Thr Ala Gly Thr Thr Gly
2570                2575                2580
Thr Ala Ala Thr Cys Thr Cys Ala Cys Ala Ala Ala Cys Thr Cys
2585                2590                2595
Ala Ala Cys Ala Cys Thr Ala Cys Cys Ala Thr Cys Ala Gly Gly
2600                2605                2610
Gly Gly Thr Thr Thr Thr Cys Thr Thr Ala Thr Gly Gly Cys
2615                2620                2625
Ala Ala Ala Gly Cys Cys Ala Ala Ala Thr Ala Gly Cys Thr
2630                2635                2640
Cys Cys Thr Ala Cys Ala Ala Thr Thr Thr Cys Thr Thr Ala Thr
2645                2650                2655
Ala Thr Cys Cys Cys Thr Cys Gly Thr Cys Ala Thr Gly Thr Gly
2660                2665                2670
Gly Cys Ala Gly Thr Ala Thr Thr Ala Thr Thr Ala Thr
2675                2680                2685
Thr Thr Ala Thr Thr Thr Gly Gly Ala Ala Gly Thr Thr Thr Gly
2690                2695                2700
Cys Cys Thr Ala Thr Cys Thr Thr Cys Thr Ala Thr Ala Thr
2705                2710                2715
Thr Thr Ala Thr Ala Gly Ala Thr Ala Thr Thr Ala Thr Ala
2720                2725                2730
Ala Ala Ala Ala Thr Gly Thr Ala Ala Cys Cys Cys Cys Thr Thr
2735                2740                2745
Thr Thr Thr Cys Cys Thr Thr Thr Cys Thr Thr Thr Cys Thr Gly Thr
2750                2755                2760
Thr Thr Ala Ala Ala Ala Thr Ala Ala Ala Ala Thr Ala Ala
2765                2770                2775
Ala Ala Thr Thr Thr Ala Thr Cys Thr Cys Ala Gly Cys Thr Thr
2780                2785                2790
Cys Thr Gly Thr Thr Ala Gly Cys Thr Thr Ala Thr Cys Cys Thr
2795                2800                2805
Cys Thr Thr Thr Gly Thr Ala Gly Thr Ala Cys Thr Ala Cys Thr
2810                2815                2820
Thr Ala Ala Ala Ala Gly Cys Ala Thr Gly Thr Cys Gly Gly Ala
2825                2830                2835
Ala Thr Ala Thr Ala Ala Gly Ala Ala Thr Ala Ala Ala Ala
2840                2845                2850
Gly Gly Ala Thr Thr Ala Thr Gly Gly Gly Ala Gly Gly Gly
2855                2860                2865
Ala Ala Cys Ala Thr Thr Ala Gly Gly Gly Ala Ala Ala Thr Cys
2870                2875                2880
Cys Ala Gly Ala Gly Ala Ala Gly Gly Cys Ala Ala Ala Ala Thr
2885                2890                2895
Thr Gly Ala Ala Ala Ala Ala Ala Ala Gly Ala Thr Thr Thr Thr
2900                2905                2910
```

```
Ala Gly Ala Ala Thr Thr Thr Ala Ala Ala Thr Thr Thr
        2915                2920                2925

Thr Cys Ala Ala Ala Gly Ala Thr Thr Cys Thr Thr Cys Cys
        2930                2935                2940

Ala Thr Thr Cys Ala Thr Ala Ala Gly Gly Ala Gly Ala Cys Thr
        2945                2950                2955

Cys Ala Ala Thr Gly Ala Thr Thr Thr Ala Ala Thr Thr Gly
        2960                2965                2970

Ala Thr Cys Thr Ala Gly Ala Cys Ala Gly Ala Ala Thr Thr Ala
        2975                2980                2985

Thr Thr Thr Ala Ala Gly Thr Thr Thr Thr Ala Thr Cys Ala Ala
        2990                2995                3000

Thr Ala Thr Thr Gly Gly Ala Thr Thr Thr Cys Thr Gly Gly Thr
        3005                3010                3015

<210> SEQ ID NO 35
<211> LENGTH: 251
<212> TYPE: PRT
<213> ORGANISM: Homo Sapiens

<400> SEQUENCE: 35

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 36
```

```
<211> LENGTH: 251
<212> TYPE: PRT
<213> ORGANISM: Homo Sapiens

<400> SEQUENCE: 36
```

| | | | | | | | | | | | | | | | |
|---|---|---|---|---|---|---|---|---|---|---|---|---|---|---|---|
| Met | Leu | Gly | Ala | Arg | Leu | Arg | Leu | Trp | Val | Cys | Ala | Leu | Cys | Ser | Val |
| 1 | | | | 5 | | | | | 10 | | | | | 15 | |
| Cys | Ser | Met | Ser | Val | Leu | Arg | Ala | Tyr | Pro | Asn | Ala | Ser | Pro | Leu | Leu |
| | | | 20 | | | | | 25 | | | | | 30 | | |
| Gly | Ser | Ser | Trp | Gly | Gly | Leu | Ile | His | Leu | Tyr | Thr | Ala | Thr | Ala | Arg |
| | | 35 | | | | | 40 | | | | | 45 | | | |
| Asn | Ser | Tyr | His | Leu | Gln | Ile | His | Lys | Asn | Gly | His | Val | Asp | Gly | Ala |
| | 50 | | | | | 55 | | | | | 60 | | | | |
| Pro | His | Gln | Thr | Ile | Tyr | Ser | Ala | Leu | Met | Ile | Arg | Ser | Glu | Asp | Ala |
| 65 | | | | | 70 | | | | | 75 | | | | | 80 |
| Gly | Phe | Val | Val | Ile | Thr | Gly | Val | Met | Ser | Arg | Arg | Tyr | Leu | Cys | Met |
| | | | | 85 | | | | | 90 | | | | | 95 | |
| Asp | Phe | Arg | Gly | Asn | Ile | Phe | Gly | Ser | His | Tyr | Phe | Asp | Pro | Glu | Asn |
| | | | 100 | | | | | 105 | | | | | 110 | | |
| Cys | Arg | Phe | Gln | His | Gln | Thr | Leu | Glu | Asn | Gly | Tyr | Asp | Val | Tyr | His |
| | | 115 | | | | | 120 | | | | | 125 | | | |
| Ser | Pro | Gln | Tyr | His | Phe | Leu | Val | Ser | Leu | Gly | Arg | Ala | Lys | Arg | Ala |
| | 130 | | | | | 135 | | | | | 140 | | | | |
| Phe | Leu | Pro | Gly | Met | Asn | Pro | Pro | Tyr | Ser | Gln | Phe | Leu | Ser | Arg |
| 145 | | | | | 150 | | | | | 155 | | | | | 160 |
| Arg | Asn | Glu | Ile | Pro | Leu | Ile | His | Phe | Asn | Thr | Pro | Ile | Pro | Arg | Arg |
| | | | | 165 | | | | | 170 | | | | | 175 | |
| His | Thr | Gln | Ser | Ala | Glu | Asp | Asp | Ser | Glu | Arg | Asp | Pro | Leu | Asn | Val |
| | | | 180 | | | | | 185 | | | | | 190 | | |
| Leu | Lys | Pro | Arg | Ala | Arg | Met | Thr | Pro | Ala | Pro | Ala | Ser | Cys | Ser | Gln |
| | | | 195 | | | | | 200 | | | | | 205 | | |
| Glu | Leu | Pro | Ser | Ala | Glu | Asp | Asn | Ser | Pro | Met | Ala | Ser | Asp | Pro | Leu |
| | 210 | | | | | 215 | | | | | 220 | | | | |
| Gly | Val | Val | Arg | Gly | Gly | Arg | Val | Asn | Thr | His | Ala | Gly | Gly | Thr | Gly |
| 225 | | | | | 230 | | | | | 235 | | | | | 240 |
| Pro | Glu | Gly | Cys | Arg | Pro | Phe | Ala | Lys | Phe | Ile | | | | | |
| | | | | 245 | | | | | 250 | | | | | | |

```
<210> SEQ ID NO 37
<211> LENGTH: 431
<212> TYPE: PRT
<213> ORGANISM: Homo Sapiens

<400> SEQUENCE: 37
```

| | | | | | | | | | | | | | | | |
|---|---|---|---|---|---|---|---|---|---|---|---|---|---|---|---|
| Tyr | Asp | Thr | Phe | Pro | Lys | Asn | Phe | Phe | Trp | Gly | Ile | Gly | Thr | Gly | Ala |
| 1 | | | | 5 | | | | | 10 | | | | | 15 | |
| Leu | Gln | Val | Glu | Gly | Ser | Trp | Lys | Lys | Asp | Gly | Lys | Gly | Pro | Ser | Ile |
| | | | 20 | | | | | 25 | | | | | 30 | | |
| Trp | Asp | His | Phe | Ile | His | Thr | His | Leu | Lys | Asn | Val | Ser | Ser | Thr | Asn |
| | | | 35 | | | | | 40 | | | | | 45 | | |
| Gly | Ser | Ser | Asp | Ser | Tyr | Ile | Phe | Leu | Glu | Lys | Asp | Leu | Ser | Ala | Leu |
| | 50 | | | | | 55 | | | | | 60 | | | | |
| Asp | Phe | Ile | Gly | Val | Ser | Phe | Tyr | Gln | Phe | Ser | Ile | Ser | Trp | Pro | Arg |
| 65 | | | | | 70 | | | | | 75 | | | | | 80 |
| Leu | Phe | Pro | Asp | Gly | Ile | Val | Thr | Val | Ala | Asn | Ala | Lys | Gly | Leu | Gln |
| | | | | 85 | | | | | 90 | | | | | 95 | |

Tyr Tyr Ser Thr Leu Leu Asp Ala Leu Val Leu Arg Asn Ile Glu Pro
            100                 105                 110

Ile Val Thr Leu Tyr His Trp Asp Leu Pro Leu Ala Leu Gln Glu Lys
            115                 120                 125

Tyr Gly Gly Trp Lys Asn Asp Thr Ile Ile Asp Ile Phe Asn Asp Tyr
        130                 135                 140

Ala Thr Tyr Cys Phe Gln Met Phe Gly Asp Arg Val Lys Tyr Trp Ile
145                 150                 155                 160

Thr Ile His Asn Pro Tyr Leu Val Ala Trp His Gly Tyr Gly Thr Gly
                165                 170                 175

Met His Ala Pro Gly Glu Lys Gly Asn Leu Ala Ala Val Tyr Thr Val
            180                 185                 190

Gly His Asn Leu Ile Lys Ala His Ser Lys Val Trp His Asn Tyr Asn
        195                 200                 205

Thr His Phe Arg Pro His Gln Lys Gly Trp Leu Ser Ile Thr Leu Gly
    210                 215                 220

Ser His Trp Ile Glu Pro Asn Arg Ser Glu Asn Thr Met Asp Ile Phe
225                 230                 235                 240

Lys Cys Gln Gln Ser Met Val Ser Val Leu Gly Trp Phe Ala Asn Pro
                245                 250                 255

Ile His Gly Asp Gly Asp Tyr Pro Glu Gly Met Arg Lys Lys Leu Phe
            260                 265                 270

Ser Val Leu Pro Ile Phe Ser Glu Ala Glu Lys His Glu Met Arg Gly
        275                 280                 285

Thr Ala Asp Phe Phe Ala Phe Ser Phe Gly Pro Asn Asn Phe Lys Pro
    290                 295                 300

Leu Asn Thr Met Ala Lys Met Gly Gln Asn Val Ser Leu Asn Leu Arg
305                 310                 315                 320

Glu Ala Leu Asn Trp Ile Lys Leu Glu Tyr Asn Asn Pro Arg Ile Leu
                325                 330                 335

Ile Ala Glu Asn Gly Trp Phe Thr Asp Ser Arg Val Lys Thr Glu Asp
            340                 345                 350

Thr Thr Ala Ile Tyr Met Met Lys Asn Phe Leu Ser Gln Val Leu Gln
        355                 360                 365

Ala Ile Arg Leu Asp Glu Ile Arg Val Phe Gly Tyr Thr Ala Trp Ser
    370                 375                 380

Leu Leu Asp Gly Phe Glu Trp Gln Asp Ala Tyr Thr Ile Arg Arg Gly
385                 390                 395                 400

Leu Phe Tyr Val Asp Phe Asn Ser Lys Gln Lys Glu Arg Lys Pro Lys
                405                 410                 415

Ser Ser Ala His Tyr Tyr Lys Gln Ile Ile Arg Glu Asn Gly Phe
            420                 425                 430

<210> SEQ ID NO 38
<211> LENGTH: 397
<212> TYPE: PRT
<213> ORGANISM: Homo Sapiens

<400> SEQUENCE: 38

Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
            20                  25                  30

Trp Ala Ser Val Leu Pro Thr Gly Asn Leu Ser Ala Val Asn Arg Gln
        35                  40                  45

Ala Leu Arg Tyr Tyr Arg Cys Val Ser Glu Gly Leu Lys Leu Gly
         50                  55                  60

Ile Ser Ala Met Val Thr Leu Tyr Tyr Pro Thr His Ala His Leu Gly
 65                  70                  75                  80

Leu Pro Glu Pro Leu Leu His Ala Asp Gly Trp Leu Asn Pro Ser Thr
                 85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
        115                 120                 125

Asp Ile Tyr Asn Arg Ser Gly Asn Asp Thr Tyr Gly Ala Ala His Asn
130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
210                 215                 220

Arg Arg Gly Leu Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
370                 375                 380

Ile Gln Phe Tyr Asn Lys Val Ile Ser Ser Arg Gly Phe
385                 390                 395

<210> SEQ ID NO 39
<211> LENGTH: 946
<212> TYPE: PRT
<213> ORGANISM: Homo Sapiens

<400> SEQUENCE: 39

Gly Phe Ser Gly Asp Gly Arg Ala Ile Trp Ser Lys Asn Pro Asn Phe
 1               5                  10                  15

Thr Pro Val Asn Glu Ser Gln Leu Phe Leu Tyr Asp Thr Phe Pro Lys
                20                  25                  30

```
            Asn Phe Phe Trp Gly Ile Gly Thr Gly Ala Leu Gln Val Glu Gly Ser
                     35                  40                  45

Trp Lys Lys Asp Gly Lys Gly Pro Ser Ile Trp Asp His Phe Ile His
             50                  55                  60

Thr His Leu Lys Asn Val Ser Ser Thr Asn Gly Ser Ser Asp Ser Tyr
             65                  70                  75                  80

Ile Phe Leu Glu Lys Asp Leu Ser Ala Leu Asp Phe Ile Gly Val Ser
                             85                  90                  95

Phe Tyr Gln Phe Ser Ile Ser Trp Pro Arg Leu Phe Pro Asp Gly Ile
                            100                 105                 110

Val Thr Val Ala Asn Ala Lys Gly Leu Gln Tyr Tyr Ser Thr Leu Leu
                        115                 120                 125

Asp Ala Leu Val Leu Arg Asn Ile Glu Pro Ile Val Thr Leu Tyr His
                    130                 135                 140

Trp Asp Leu Pro Leu Ala Leu Gln Glu Lys Tyr Gly Gly Trp Lys Asn
            145                 150                 155                 160

Asp Thr Ile Ile Asp Ile Phe Asn Asp Tyr Ala Thr Tyr Cys Phe Gln
                            165                 170                 175

Met Phe Gly Asp Arg Val Lys Tyr Trp Ile Thr Ile His Asn Pro Tyr
                        180                 185                 190

Leu Val Ala Trp His Gly Tyr Gly Thr Gly Met His Ala Pro Gly Glu
                    195                 200                 205

Lys Gly Asn Leu Ala Ala Val Tyr Thr Val Gly His Asn Leu Ile Lys
            210                 215                 220

Ala His Ser Lys Val Trp His Asn Tyr Asn Thr His Phe Arg Pro His
            225                 230                 235                 240

Gln Lys Gly Trp Leu Ser Ile Thr Leu Gly Ser His Trp Ile Glu Pro
                            245                 250                 255

Asn Arg Ser Glu Asn Thr Met Asp Ile Phe Lys Cys Gln Gln Ser Met
                        260                 265                 270

Val Ser Val Leu Gly Trp Phe Ala Asn Pro Ile His Gly Asp Gly Asp
                    275                 280                 285

Tyr Pro Glu Gly Met Arg Lys Lys Leu Phe Ser Val Leu Pro Ile Phe
            290                 295                 300

Ser Glu Ala Glu Lys His Glu Met Arg Gly Thr Ala Asp Phe Phe Ala
            305                 310                 315                 320

Phe Ser Phe Gly Pro Asn Asn Phe Lys Pro Leu Asn Thr Met Ala Lys
                            325                 330                 335

Met Gly Gln Asn Val Ser Leu Asn Leu Arg Glu Ala Leu Asn Trp Ile
                        340                 345                 350

Lys Leu Glu Tyr Asn Asn Pro Arg Ile Leu Ile Ala Glu Asn Gly Trp
                    355                 360                 365

Phe Thr Asp Ser Arg Val Lys Thr Glu Asp Thr Thr Ala Ile Tyr Met
            370                 375                 380

Met Lys Asn Phe Leu Ser Gln Val Leu Gln Ala Ile Arg Leu Asp Glu
            385                 390                 395                 400

Ile Arg Val Phe Gly Tyr Thr Ala Trp Ser Leu Leu Asp Gly Phe Glu
                            405                 410                 415

Trp Gln Asp Ala Tyr Thr Ile Arg Arg Gly Leu Phe Tyr Val Asp Phe
                        420                 425                 430

Asn Ser Lys Gln Lys Glu Arg Lys Pro Lys Ser Ser Ala His Tyr Tyr
                    435                 440                 445

Lys Gln Ile Ile Arg Glu Asn Gly Phe Ser Leu Lys Glu Ser Thr Pro
            450                 455                 460
```

```
Asp Val Gln Gly Gln Phe Pro Cys Asp Phe Ser Trp Gly Val Thr Glu
465                 470                 475                 480

Ser Val Leu Lys Pro Glu Ser Val Ala Ser Pro Gln Phe Ser Asp
            485                 490                 495

Pro His Leu Tyr Val Trp Asn Ala Thr Gly Asn Arg Leu Leu His Arg
                500                 505                 510

Val Glu Gly Val Arg Leu Lys Thr Arg Pro Ala Gln Cys Thr Asp Phe
            515                 520                 525

Val Asn Ile Lys Lys Gln Leu Glu Met Leu Ala Arg Met Lys Val Thr
530                 535                 540

His Tyr Arg Phe Ala Leu Asp Trp Ala Ser Val Leu Pro Thr Gly Asn
545                 550                 555                 560

Leu Ser Ala Val Asn Arg Gln Ala Leu Arg Tyr Tyr Arg Cys Val Val
                565                 570                 575

Ser Glu Gly Leu Lys Leu Gly Ile Ser Ala Met Val Thr Leu Tyr Tyr
            580                 585                 590

Pro Thr His Ala His Leu Gly Leu Pro Glu Pro Leu Leu His Ala Asp
            595                 600                 605

Gly Trp Leu Asn Pro Ser Thr Ala Glu Ala Phe Gln Ala Tyr Ala Gly
            610                 615                 620

Leu Cys Phe Gln Glu Leu Gly Asp Leu Val Lys Leu Trp Ile Thr Ile
625                 630                 635                 640

Asn Glu Pro Asn Arg Leu Ser Asp Ile Tyr Asn Arg Ser Gly Asn Asp
                645                 650                 655

Thr Tyr Gly Ala Ala His Asn Leu Leu Val Ala His Ala Leu Ala Trp
                660                 665                 670

Arg Leu Tyr Asp Arg Gln Phe Arg Pro Ser Gln Arg Gly Ala Val Ser
            675                 680                 685

Leu Ser Leu His Ala Asp Trp Ala Glu Pro Ala Asn Pro Tyr Ala Asp
            690                 695                 700

Ser His Trp Arg Ala Ala Glu Arg Phe Leu Gln Phe Glu Ile Ala Trp
705                 710                 715                 720

Phe Ala Glu Pro Leu Phe Lys Thr Gly Asp Tyr Pro Ala Ala Met Arg
                725                 730                 735

Glu Tyr Ile Ala Ser Lys His Arg Arg Gly Leu Ser Ser Ser Ala Leu
                740                 745                 750

Pro Arg Leu Thr Glu Ala Glu Arg Arg Leu Leu Lys Gly Thr Val Asp
            755                 760                 765

Phe Cys Ala Leu Asn His Phe Thr Thr Arg Phe Val Met His Glu Gln
770                 775                 780

Leu Ala Gly Ser Arg Tyr Asp Ser Asp Arg Asp Ile Gln Phe Leu Gln
785                 790                 795                 800

Asp Ile Thr Arg Leu Ser Ser Pro Thr Arg Leu Ala Val Ile Pro Trp
                805                 810                 815

Gly Val Arg Lys Leu Leu Arg Trp Val Arg Arg Asn Tyr Gly Asp Met
            820                 825                 830

Asp Ile Tyr Ile Thr Ala Ser Gly Ile Asp Asp Gln Ala Leu Glu Asp
            835                 840                 845

Asp Arg Leu Arg Lys Tyr Tyr Leu Gly Lys Tyr Leu Gln Glu Val Leu
            850                 855                 860

Lys Ala Tyr Leu Ile Asp Lys Val Arg Ile Lys Gly Tyr Tyr Ala Phe
865                 870                 875                 880

Lys Leu Ala Glu Glu Lys Ser Lys Pro Arg Phe Gly Phe Phe Thr Ser
```

```
                      885                 890                 895
Asp Phe Lys Ala Lys Ser Ser Ile Gln Phe Tyr Asn Lys Val Ile Ser
                900                 905                 910

Ser Arg Gly Phe Pro Phe Glu Asn Ser Ser Ser Arg Cys Ser Gln Thr
            915                 920                 925

Gln Glu Asn Thr Glu Cys Thr Val Cys Leu Phe Leu Val Gln Lys Lys
        930                 935                 940

Pro Leu
945

<210> SEQ ID NO 40
<211> LENGTH: 1195
<212> TYPE: PRT
<213> ORGANISM: Homo Sapiens

<400> SEQUENCE: 40

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
```

```
                305                 310                 315                 320
Glu Ser Glu Lys Lys Phe Ile Lys Gly Thr Ala Asp Phe Phe Ala Leu
                    325                 330                 335
Cys Phe Gly Pro Thr Leu Ser Phe Gln Leu Leu Asp Pro His Met Lys
                    340                 345                 350
Phe Arg Gln Leu Glu Ser Pro Asn Leu Arg Gln Leu Leu Ser Trp Ile
                    355                 360                 365
Asp Leu Glu Phe Asn His Pro Gln Ile Phe Ile Val Glu Asn Gly Trp
                    370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                    405                 410                 415
Val Asp Val Ile Gly Tyr Thr Ala Trp Ser Leu Met Asp Gly Phe Glu
                    420                 425                 430
Trp His Arg Gly Tyr Ser Ile Arg Arg Gly Leu Phe Tyr Val Asp Phe
                    435                 440                 445
Leu Ser Gln Asp Lys Met Leu Leu Pro Lys Ser Ser Ala Leu Phe Tyr
                    450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                    485                 490                 495
Asn Tyr Ile Gln Val Asp Thr Thr Leu Ser Gln Phe Thr Asp Leu Asn
                    500                 505                 510
Val Tyr Leu Trp Asp Val His His Ser Lys Arg Leu Ile Lys Val Asp
                    515                 520                 525
Gly Val Val Thr Lys Lys Arg Lys Ser Tyr Cys Val Asp Phe Ala Ala
                    530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                    565                 570                 575
Gln Val Asn His Thr Ile Leu Gln Tyr Tyr Arg Cys Met Ala Ser Glu
                    580                 585                 590
Leu Val Arg Val Asn Ile Thr Pro Val Val Ala Leu Trp Gln Pro Met
                    595                 600                 605
Ala Pro Asn Gln Gly Leu Pro Arg Leu Leu Ala Arg Gln Gly Ala Trp
                    610                 615                 620
Glu Asn Pro Tyr Thr Ala Leu Ala Phe Ala Glu Tyr Ala Arg Leu Cys
625                 630                 635                 640
Phe Gln Glu Leu Gly His His Val Lys Leu Trp Ile Thr Met Asn Glu
                    645                 650                 655
Pro Tyr Thr Arg Asn Met Thr Tyr Ser Ala Gly His Asn Leu Leu Lys
                    660                 665                 670
Ala His Ala Leu Ala Trp His Val Tyr Asn Glu Lys Phe Arg His Ala
                    675                 680                 685
Gln Asn Gly Lys Ile Ser Ile Ala Leu Gln Ala Asp Trp Ile Glu Pro
                    690                 695                 700
Ala Cys Pro Phe Ser Gln Lys Asp Lys Glu Val Ala Glu Arg Val Leu
705                 710                 715                 720
Glu Phe Asp Ile Gly Trp Leu Ala Glu Pro Ile Phe Gly Ser Gly Asp
                    725                 730                 735
```

```
Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
            755                 760                 765

Asp Phe Leu Ala Leu Ser His Tyr Thr Thr Ile Leu Val Asp Ser Glu
            770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
            850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
            885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
            915                 920                 925

Phe Cys Pro Glu Glu Phe Thr Val Cys Thr Glu Cys Ser Phe Phe His
            930                 935                 940

Thr Arg Lys Ser Leu Gly Ser Gly Gly Gly Ser Gly Gly Gly Gly
945                 950                 955                 960

Ser Gly Gly Gly Gly Ser Leu Lys Tyr Pro Asn Ala Ser Pro Leu Leu
            965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
            995                 1000                1005

Pro His  Gln Thr Ile Tyr Ser  Ala Leu Met Ile Arg  Ser Glu Asp
            1010                1015                1020

Ala Gly  Phe Val Val Ile Thr  Gly Val Met Ser Arg  Arg Tyr Leu
            1025                1030                1035

Cys Met  Asp Phe Arg Gly Asn  Ile Phe Gly Ser His  Tyr Phe Asp
            1040                1045                1050

Pro Glu  Asn Cys Arg Phe Gln  His Gln Thr Leu Glu  Asn Gly Tyr
            1055                1060                1065

Asp Val  Tyr His Ser Pro Gln  Tyr His Phe Leu Val  Ser Leu Gly
            1070                1075                1080

Arg Ala  Lys Arg Ala Phe Leu  Pro Gly Met Asn Pro  Pro Pro Tyr
            1085                1090                1095

Ser Gln  Phe Leu Ser Arg Arg  Asn Glu Ile Pro Leu  Ile His Phe
            1100                1105                1110

Asn Thr  Pro Ile Pro Arg Arg  His Thr Arg Ser Ala  Glu Asp Asp
            1115                1120                1125

Ser Glu  Arg Asp Pro Leu Asn  Val Leu Lys Pro Arg  Ala Arg Met
            1130                1135                1140

Thr Pro  Ala Pro Ala Ser Cys  Ser Gln Glu Leu Pro  Ser Ala Glu
            1145                1150                1155
```

```
Asp Asn Ser Pro Met Ala Ser Asp Pro Leu Gly Val Val Arg Gly
    1160                1165                1170

Gly Arg Val Asn Thr His Ala Gly Gly Thr Pro Glu Gly Cys
    1175                1180                1185

Arg Pro Phe Ala Lys Phe Ile
    1190            1195

<210> SEQ ID NO 41
<211> LENGTH: 1195
<212> TYPE: PRT
<213> ORGANISM: Homo Sapiens

<400> SEQUENCE: 41

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
            35                  40                  45

Gln His Gly Lys Gly Ala Ser Ile Trp Asp Thr Phe Thr His His Pro
        50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
        130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335
```

```
Cys Phe Gly Pro Thr Leu Ser Phe Gln Leu Leu Asp Pro His Met Lys
            340                 345                 350
Phe Arg Gln Leu Glu Ser Pro Asn Leu Arg Gln Leu Leu Ser Trp Ile
            355                 360                 365
Asp Leu Glu Phe Asn His Pro Gln Ile Phe Ile Val Glu Asn Gly Trp
        370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                405                 410                 415
Val Asp Val Ile Gly Tyr Thr Ala Trp Ser Leu Met Asp Gly Phe Glu
            420                 425                 430
Trp His Arg Gly Tyr Ser Ile Arg Arg Gly Leu Phe Tyr Val Asp Phe
            435                 440                 445
Leu Ser Gln Asp Lys Met Leu Leu Pro Lys Ser Ser Ala Leu Phe Tyr
        450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                485                 490                 495
Asn Tyr Ile Gln Val Asp Thr Thr Leu Ser Gln Phe Thr Asp Leu Asn
            500                 505                 510
Val Tyr Leu Trp Asp Val His His Ser Lys Arg Leu Ile Lys Val Asp
        515                 520                 525
Gly Val Val Thr Lys Lys Arg Lys Ser Tyr Cys Val Asp Phe Ala Ala
530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
            565                 570                 575
Gln Val Asn His Thr Ile Leu Gln Tyr Tyr Arg Cys Met Ala Ser Glu
        580                 585                 590
Leu Val Arg Val Asn Ile Thr Pro Val Val Ala Leu Trp Gln Pro Met
        595                 600                 605
Ala Pro Asn Gln Gly Leu Pro Arg Leu Leu Ala Arg Gln Gly Ala Trp
610                 615                 620
Glu Asn Pro Tyr Thr Ala Leu Ala Phe Ala Glu Tyr Ala Arg Leu Cys
625                 630                 635                 640
Phe Gln Glu Leu Gly His His Val Lys Leu Trp Ile Thr Met Asn Glu
                645                 650                 655
Pro Tyr Thr Arg Asn Met Thr Tyr Ser Ala Gly His Asn Leu Leu Lys
            660                 665                 670
Ala His Ala Leu Ala Trp His Val Tyr Asn Glu Lys Phe Arg His Ala
        675                 680                 685
Gln Asn Gly Lys Ile Ser Ile Ala Leu Gln Ala Asp Trp Ile Glu Pro
690                 695                 700
Ala Cys Pro Phe Ser Gln Lys Asp Lys Glu Val Ala Glu Arg Val Leu
705                 710                 715                 720
Glu Phe Asp Ile Gly Trp Leu Ala Glu Pro Ile Phe Gly Ser Gly Asp
                725                 730                 735
Tyr Pro Trp Val Met Arg Asp Trp Leu Asn Gln Arg Asn Asn Phe Leu
            740                 745                 750
Leu Pro Tyr Phe Thr Glu Asp Glu Lys Lys Leu Ile Gln Gly Thr Phe
```

```
              755                 760                 765
Asp Phe Leu Ala Leu Ser His Tyr Thr Thr Ile Leu Val Asp Ser Glu
770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
                820                 825                 830

Leu Pro Met Tyr Ile Ile Ser Asn Gly Ile Asp Asp Gly Leu His Ala
                835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
                900                 905                 910

Lys Ile Ile Asp Ser Asn Gly Phe Pro Gly Pro Glu Thr Leu Glu Arg
                915                 920                 925

Phe Cys Pro Glu Glu Phe Thr Val Cys Thr Glu Cys Ser Phe Phe His
930                 935                 940

Thr Arg Lys Ser Leu Gly Ser Gly Gly Gly Ser Gly Gly Gly Gly
945                 950                 955                 960

Ser Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
                980                 985                 990

Asn Ser Tyr His Leu Gln Ile His Lys Asn Gly His Val Asp Gly Ala
                995                 1000                1005

Pro His Gln Thr Ile Tyr Ser Ala Leu Met Ile Arg Ser Glu Asp
      1010                1015                1020

Ala Gly Phe Val Val Ile Thr Gly Val Met Ser Arg Arg Tyr Leu
      1025                1030                1035

Cys Met Asp Phe Arg Gly Asn Ile Phe Gly Ser His Tyr Phe Asp
      1040                1045                1050

Pro Glu Asn Cys Arg Phe Gln His Gln Thr Leu Glu Asn Gly Tyr
      1055                1060                1065

Asp Val Tyr His Ser Pro Gln Tyr His Phe Leu Val Ser Leu Gly
      1070                1075                1080

Arg Ala Lys Arg Ala Phe Leu Pro Gly Met Asn Pro Pro Pro Tyr
      1085                1090                1095

Ser Gln Phe Leu Ser Arg Arg Asn Glu Ile Pro Leu Ile His Phe
      1100                1105                1110

Asn Thr Pro Ile Pro Arg Arg His Thr Gln Ser Ala Glu Asp Asp
      1115                1120                1125

Ser Glu Arg Asp Pro Leu Asn Val Leu Lys Pro Arg Ala Arg Met
      1130                1135                1140

Thr Pro Ala Pro Ala Ser Cys Ser Gln Glu Leu Pro Ser Ala Glu
      1145                1150                1155

Asp Asn Ser Pro Met Ala Ser Asp Pro Leu Gly Val Val Arg Gly
      1160                1165                1170
```

-continued

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 42
<211> LENGTH: 227
<212> TYPE: PRT
<213> ORGANISM: Homo Sapiens

<400> SEQUENCE: 42

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 43
<211> LENGTH: 227
<212> TYPE: PRT
<213> ORGANISM: Homo Sapiens

<400> SEQUENCE: 43

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly

```
            65                  70                  75                  80
Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Gln Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 44
<211> LENGTH: 982
<212> TYPE: PRT
<213> ORGANISM: Homo Sapiens

<400> SEQUENCE: 44

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
```

-continued

```
            210                 215                 220
Arg His Phe Gly Gly Gln Val Lys Tyr Trp Ile Thr Ile Asp Asn Pro
225                 230                 235                 240

Tyr Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
290                 295                 300

Pro Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
                610                 615                 620

Glu Leu Val Arg Val Asn Ile Thr Pro Val Val Ala Leu Trp Gln Pro
625                 630                 635                 640
```

```
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
        835                 840                 845
Pro Trp Gly Leu Arg Lys Val Leu Asn Trp Leu Lys Phe Lys Tyr Gly
    850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
            900                 905                 910
Phe Ala Tyr Ser Phe Asn Asp Arg Thr Ala Pro Arg Phe Gly Leu Tyr
        915                 920                 925
Arg Tyr Ala Ala Asp Gln Phe Glu Pro Lys Ala Ser Met Lys His Tyr
    930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
His Thr Arg Lys Ser Leu
            980

<210> SEQ ID NO 45
<211> LENGTH: 974
<212> TYPE: PRT
<213> ORGANISM: Homo Sapiens

<400> SEQUENCE: 45

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
                20                  25                  30
```

-continued

```
Thr Trp Ala Arg Phe Ser Arg Pro Ala Pro Glu Ala Ala Gly Leu
             35                  40                  45
Phe Gln Gly Thr Phe Pro Asp Gly Phe Leu Trp Ala Val Gly Ser Ala
 50                  55                  60
Ala Tyr Gln Thr Glu Gly Gly Trp Gln His Gly Lys Gly Ala Ser
 65                  70                  75                  80
Ile Trp Asp Thr Phe Thr His His Pro Leu Ala Pro Pro Gly Asp Ser
                     85                  90                  95
Arg Asn Ala Ser Leu Pro Leu Gly Ala Pro Ser Pro Leu Gln Pro Ala
                100                 105                 110
Thr Gly Asp Val Ala Ser Asp Ser Tyr Asn Asn Val Phe Arg Asp Thr
                115                 120                 125
Glu Ala Leu Arg Glu Leu Gly Val Thr His Tyr Arg Phe Ser Ile Ser
 130                 135                 140
Trp Ala Arg Val Leu Pro Asn Gly Ser Ala Gly Val Pro Asn Arg Glu
145                 150                 155                 160
Gly Leu Arg Tyr Tyr Arg Arg Leu Leu Glu Arg Leu Arg Glu Leu Gly
                165                 170                 175
Val Gln Pro Val Val Thr Leu Tyr His Trp Asp Leu Pro Gln Arg Leu
                180                 185                 190
Gln Asp Ala Tyr Gly Gly Trp Ala Asn Arg Ala Leu Ala Asp His Phe
                195                 200                 205
Arg Asp Tyr Ala Glu Leu Cys Phe Arg His Phe Gly Gly Gln Val Lys
 210                 215                 220
Tyr Trp Ile Thr Ile Asp Asn Pro Tyr Val Val Ala Trp His Gly Tyr
225                 230                 235                 240
Ala Thr Gly Arg Leu Ala Pro Gly Ile Arg Gly Ser Pro Arg Leu Gly
                245                 250                 255
Tyr Leu Val Ala His Asn Leu Leu Ala His Ala Lys Val Trp His
                260                 265                 270
Leu Tyr Asn Thr Ser Phe Arg Pro Thr Gln Gly Gly Gln Val Ser Ile
                275                 280                 285
Ala Leu Ser Ser His Trp Ile Asn Pro Arg Arg Met Thr Asp His Ser
 290                 295                 300
Ile Lys Glu Cys Gln Lys Ser Leu Asp Phe Val Leu Gly Trp Phe Ala
305                 310                 315                 320
Lys Pro Val Phe Ile Asp Gly Asp Tyr Pro Glu Ser Met Lys Asn Asn
                325                 330                 335
Leu Ser Ser Ile Leu Pro Asp Phe Thr Glu Ser Glu Lys Lys Phe Ile
                340                 345                 350
Lys Gly Thr Ala Asp Phe Phe Ala Leu Cys Phe Gly Pro Thr Leu Ser
                355                 360                 365
Phe Gln Leu Leu Asp Pro His Met Lys Phe Arg Gln Leu Glu Ser Pro
 370                 375                 380
Asn Leu Arg Gln Leu Leu Ser Trp Ile Asp Leu Glu Phe Asn His Pro
385                 390                 395                 400
Gln Ile Phe Ile Val Glu Asn Gly Trp Phe Val Ser Gly Thr Thr Lys
                405                 410                 415
Arg Asp Asp Ala Lys Tyr Met Tyr Tyr Leu Lys Lys Phe Ile Met Glu
                420                 425                 430
Thr Leu Lys Ala Ile Lys Leu Asp Gly Val Asp Val Ile Gly Tyr Thr
                435                 440                 445
Ala Trp Ser Leu Met Asp Gly Phe Glu Trp His Arg Gly Tyr Ser Ile
 450                 455                 460
```

```
Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
            500                 505                 510

Cys Asp Phe Ala Trp Gly Val Val Asp Asn Tyr Ile Gln Val Asp Thr
            515                 520                 525

Thr Leu Ser Gln Phe Thr Asp Leu Asn Val Tyr Leu Trp Asp Val His
        530                 535                 540

His Ser Lys Arg Leu Ile Lys Val Asp Gly Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
        595                 600                 605

Gln Tyr Tyr Arg Cys Met Ala Ser Glu Leu Val Arg Val Asn Ile Thr
        610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
            660                 665                 670

Val Lys Leu Trp Ile Thr Met Asn Glu Pro Tyr Thr Arg Asn Met Thr
        675                 680                 685

Tyr Ser Ala Gly His Asn Leu Leu Lys Ala His Ala Leu Ala Trp His
        690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
            755                 760                 765

Trp Leu Asn Gln Arg Asn Asn Phe Leu Leu Pro Tyr Phe Thr Glu Asp
        770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Pro Trp Gly Leu Arg Lys Val Leu
        835                 840                 845

Asn Trp Leu Lys Phe Lys Tyr Gly Asp Leu Pro Met Tyr Ile Ile Ser
        850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
```

-continued

```
                885                 890                 895
Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
            915                 920                 925

Pro Lys Ala Ser Met Lys His Tyr Arg Lys Ile Ile Asp Ser Asn Gly
            930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu
                965                 970
```

METHODS AND COMPOSITIONS USING KLOTHO-FGF FUSION POLYPEPTIDES

This application claims priority to U.S. Provisional Application Ser. No. 61/063,015 filed 28 Jan. 2008, the contents of which are incorporated herein by reference in their entirety.

1. BACKGROUND

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029 38034 (2005)).

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FG-FRs) are tyrosine kinase receptors that activate signal transduction through autophosphorylation of FGFR, phosphorylation of FRS2 (FGF receptor substrate 2) and ERK1/2 (extracellular signal-regulated protein kinase ½), and activating Egr-1 (early growth response-1). FGFs also have a high affinity for heparin sulfate proteoglycans. When bound to FGFs, heparin sulfate enhances the activation of FGFRs.

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling through their respective cognate FGF receptors (Ogawa et al., Proc. Natl. Acad. Sci. USA 104:7432-7 (2007); Lin et al., J. Biol. Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August; 115(8): 2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

2. SUMMARY OF THE INVENTION

The present invention is directed to methods, kits and compositions for preventing or treating age-related conditions or metabolic disorders with Klotho fusion polypeptides or soluble Klotho polypeptides. The Klotho fusion polypeptides of the present invention are formed of a Klotho protein or an active fragment thereof (e.g., sKlotho). In some embodiments, the present invention provides a Klotho fusion polypeptide comprising a Klotho protein or an active fragment thereof and a fibroblast growth factor or an active fragment thereof.

In a first aspect, the invention provides a fusion polypeptide having at least one extracellular subdomain of a Klotho protein and a fibroblast growth factor or an active fragment thereof. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the invention. The reader of the instant application may assume that each of every combination of alpha or beta extracellular domain with each human FGF protein or an active fragment thereof are individually and specifically contemplated.

According to the present invention, the extracellular domain of the Klotho protein can include one or both of the KL-D1 and KL-D2 domains of a Klotho protein. In some embodiments, the Klotho fusion polypeptide of the invention has at least two extracellular subdomains of a Klotho protein. For example, the two extracellular subdomains can be two KL-D1 domains in tandem repeats, two KL-D2 domains in tandem repeats, or one KL-D1 domain and one KL-D2 domain. In one embodiment, the fusion polypeptide of the invention comprises amino acids 28-292 of the full length alpha Klotho protein. In another embodiment, the fusion polypeptide of the invention comprises amino acids 52-997 of the full length beta Klotho protein.

According to the present invention, a polypeptide comprising at least one extracellular subdomain of a Klotho protein and a FGF or an active fragment thereof may be linked together covalently, for example, chemically linked or fused in frame by a peptide bond. They may also linked via a linker. Non-limiting examples of polypeptide linker are SEQ ID NOs:11, 12, 13, 14, 15, 16, 17, and 18. Such linkers may comprise at least one and up to about 30 repeats of SEQ ID NOs:11, 12, 13, 14, 15, 16, 17 and 18.

According to the present invention, the extracellular subdomain of a Klotho protein and the fibroblast growth factor can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present invention provides a fusion polypeptide comprising a sKlotho of a Klotho protein and a linker. In another embodiment, the present invention provides a fusion polypeptide comprising a sKlotho of the alpha Klotho protein and a linker. In another embodiment, the present invention provides a fusion polypeptide comprising a sKlotho of the beta Klotho protein and a linker. In yet another embodiment, the present invention provides a human FGF protein or an active fragment thereof (e.g., without signal peptide) and a linker. Pharmaceutical compositions comprising the fusion proteins of the invention and their uses for treating or preventing age-related conditions or metabolic disorders are also encompassed by the present invention.

In one embodiment, the present invention provides a fusion polypeptide comprising a sKlotho of alpha Klotho protein with signal peptide fused (directly or indirectly via a linker) to FGF-23. In another embodiment, the present invention provides a fusion polypeptide comprising a sKlotho of alpha Klotho protein without signal peptide fused (directly or indirectly via a linker) to FGF-23. In another embodiment, the present invention provides sKlotho of alpha Klotho protein with signal peptide fused (directly or indirectly via a linker) to FGF-23 without signal peptide. In another embodiment, the present invention provides a fusion polypeptide comprising sKlotho of alpha Klotho protein without signal peptide fused (directly or indirectly via a linker) to FGF-23 without signal peptide.

In one embodiment, the present invention provides a fusion polypeptide comprising a sKlotho of alpha Klotho protein with signal peptide fused (directly or indirectly via a linker) to FGF-23 (R179Q) variant. In another embodiment, the present invention provides a fusion polypeptide comprising a sKlotho of alpha Klotho protein without signal peptide fused (directly or indirectly via a linker) to FGF-23 (R179Q) variant. In another embodiment, the present invention provides sKlotho of alpha Klotho protein with signal peptide fused (directly or indirectly via a linker) to FGF-23 (R179Q) variant without signal peptide. In another embodiment, the present invention provides a fusion polypeptide comprising sKlotho of alpha Klotho protein without signal peptide fused (directly or indirectly via a linker) to FGF-23 (R179Q) variant without signal peptide.

In one embodiment, the present invention provides a fusion polypeptide comprising (1) sKlotho of alpha Klotho protein with signal peptide; (2) a linker; and (3) FGF-23 (R179Q) variant without signal peptide. In another embodiment, the present invention provides a fusion polypeptide comprising (1) sKlotho of alpha Klotho protein without signal peptide; (2) a linker; and (3) FGF-23 (R179Q) variant without signal peptide. In some embodiments, the fusion polypeptides of the invention are glycosylated.

In one embodiment, the present invention provides a fusion polypeptide comprising (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43). In another embodiment, the present invention provides a fusion polypeptide comprising (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43). In one embodiment, the present invention provides a fusion polypeptide comprising the amino acid sequence of SEQ ID NO:19, 20, 40, or 41. In some embodiments, the fusion polypeptides of the invention are glycosylated.

In one embodiment, the present invention provides a fusion polypeptide comprising sKlotho of alpha Klotho protein with signal peptide (SEQ ID NO:44 or SEQ ID NO:45); and a linker comprising SEQ ID NO:11. In another embodiment, the present invention provides a fusion polypeptide comprising sKlotho of alpha Klotho protein without signal peptide (SEQ ID NO:7); and a linker comprising SEQ ID NO:11. In some embodiments, the fusion polypeptides of the invention are glycosylated.

In one embodiment, the present invention provides a fusion polypeptide comprising a human FGF protein or an active fragment thereof (e.g., without the signal peptide); and a linker comprising SEQ ID NO:11. In some embodiments, the fusion polypeptides of the invention are glycosylated.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43); and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43); and uses of the pharmaceutical composition for treating and/or preventing age-related conditions, such as muscular atrophy. In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO:19, 20, 40, or 41; and uses of the pharmaceutical composition for treating and/or preventing age-related conditions, such as muscular atrophy.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO:44 or SEQ ID NO:45); and a linker comprising SEQ ID NO:11; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO:7); and a linker comprising SEQ ID NO:11; and uses of the pharmaceutical composition for treating and/or preventing age-related conditions, such as muscular atrophy.

In one embodiment, the present invention provides a pharmaceuticals composition comprising (e.g., as a sole pharmaceutically active ingredient) a fusion polypeptide (e.g., glycosylated or non-glycosylated) that comprises a human FGF protein or an active fragment thereof (e.g., without the signal peptide); and a linker comprising SEQ ID NO:11.

Pharmaceutical compositions comprising the fusion proteins of the invention and their uses for treating or preventing age-related conditions (e.g., muscle atrophy) or metabolic disorders (e.g., diabete) are also encompassed by the present invention.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO:19. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present invention provides a fusion polypeptide comprising a sKlotho of beta Klotho protein with signal peptide fused (directly or indirectly via a linker) to FGF-19 or an active fragment thereof. In another embodiment, the present invention provides a fusion polypeptide comprising a sKlotho of beta Klotho protein without signal peptide fused (directly or indirectly via a linker) to FGF-19 or an active fragment thereof. In another embodiment, the present invention provides a fusion polypeptide comprising a sKlotho of beta Klotho protein with signal peptide fused (directly or indirectly via a linker) to FGF-21 or an active fragment thereof. In another embodiment, the present invention provides a fusion polypeptide comprising a sKlotho of beta Klotho protein without signal peptide fused (directly or indirectly via a linker) to FGF-21 or an active fragment thereof.

The invention provides nucleic acid sequences encoding any of the Klotho fusion polypeptides described herein and host cells containing the nucleic acids.

The invention also provides composition having any of the Klotho fusion polypeptides contemplated herein. The compositions of the invention can further include heparin.

The invention also provides a method for treating or preventing an age-related condition in an individual. An individual (e.g, human) is administered a therapeutically effective dose of a pharmaceutical composition containing a Klotho fusion polypeptide, having at least one extracellular subdomain of a Klotho protein (e.g., alpha Klotho protein) and a fibroblast growth factor or an active fragment thereof so as to treat or prevent the age-related condition. In particular, the invention provides a method of treating or preventing muscle wasting comprising administering to an individual (e.g., human) an therapeutically effective amount of a fusion polypeptide having at least one extracellular subdomain of an alpha Klotho protein and a fibroblast growth factor (or an active fragment thereof).

Additionally, the invention provides a method for treating or preventing a metabolic disorder in an individual. An individual is administered a therapeutically effective dose of a pharmaceutical composition containing a fusion polypeptide of the invention, having at least one extracellular subdomain of a Klotho protein and a fibroblast growth factor (or an active fragment thereof) so as to treat the metabolic disorder. In particular, a fusion polypeptide of the invention having at least one extracellular subdomain of a beta-Klotho protein and a fibroblast growth factor 21 is useful for treating a metabolic disorder.

Klotho-FGF23 fusion polypeptides of the invention can be used for treating or preventing hyperphosphatemia or calcinosis in an individual. A pharmacologically effective dose of a pharmaceutical composition containing the Klotho fusion polypeptide of the invention, having at least one extracellular subdomain of a Klotho protein and a fibroblast growth factor, is administered to treat or prevent hyperphosphatemia or calcinosis. In particular, a Klotho fusion polypeptide of the invention having at least one extracellular subdomain of an alpha Klotho protein and a fibroblast growth factor 23 is useful for treating hyperphosphatemia or calcinosis.

Klotho-FGF23 fusion polypeptides of the invention can be used for treating or preventing chronic renal disease or chronic renal failure in an individual. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the invention can be used for treating or preventing cancer (e.g., breast cancer) in an individual. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent cancer or breast cancer.

The present invention provides fusion polypeptides comprising at least one extracellular subdomain of Klotho protein and a FGF or an active fragment thereof for use in medicine. In one embodiment, the present invention provides fusion polypeptides comprising at least one extracellular subdomain of Klotho protein and a FGF or an active fragment thereof for use in treating or preventing muscle atrophy. The present invention also provides a method of treating or preventing an age related condition (e.g., muscle atrophy) comprising administering to an individual in need thereof a therapeutically effective dose of a pharmaceutical composition comprising a soluble Klotho protein.

The invention also includes kits for treating or preventing an age-related disorder or metabolic disorder in an individual. The kit includes instructions for use and a purified Klotho fusion polypeptide having at least one extracellular subdomain of a Klotho protein and a fibroblast growth factor.

The invention also provides a kit for producing a Klotho fusion polypeptide of the invention. The kit of the invention includes instructions for use and a nucleic acid encoding a Klotho fusion polypeptide, having at least one extracellular subdomain of Klotho protein and a fibroblast growth factor.

3. BRIEF DESCRIPTION OF THE DRAWINGS

FIG. 1 illustrates several different embodiments of the Klotho fusion polypeptides of the invention. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., a.a. 1 to 982 of human Klotho), or an active fragment of Klotho.

Figure 2A:
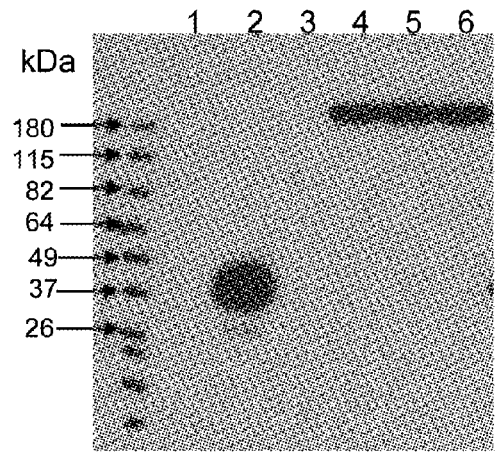
Figure 2B:
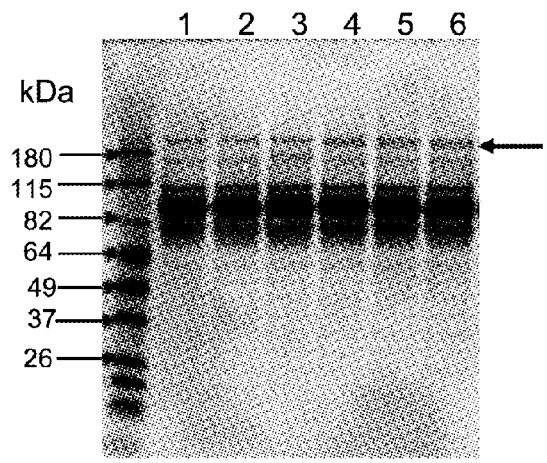
Figure 2C:
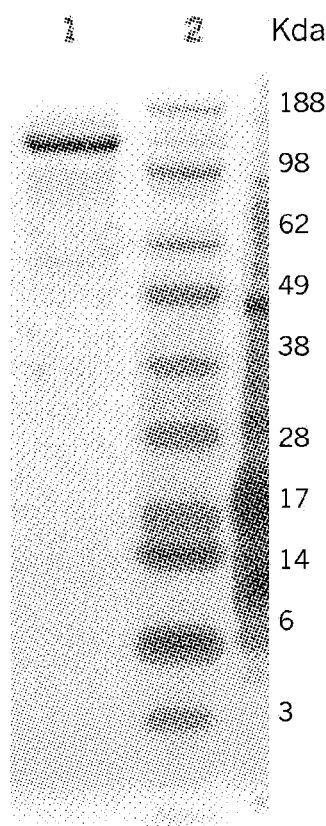

FIGS. 2A-2C depict protein expression of an sKlotho-FGF23 fusion protein. FIG. 2A shows that sKlotho-FGF23 fusion protein was detected in conditioned media by Western blotting with anti-FGF23 antibodies. FIG. 2B shows that sKlotho-FGF23 fusion protein was detected in conditioned media by SDS-PAGE and Coomassie blue staining FIG. 2C shows a highly purified sKlotho-FGF23-6×His fusion protein, analyzed by SDS-PAGE and Coomassie blue staining.

Figure 3:
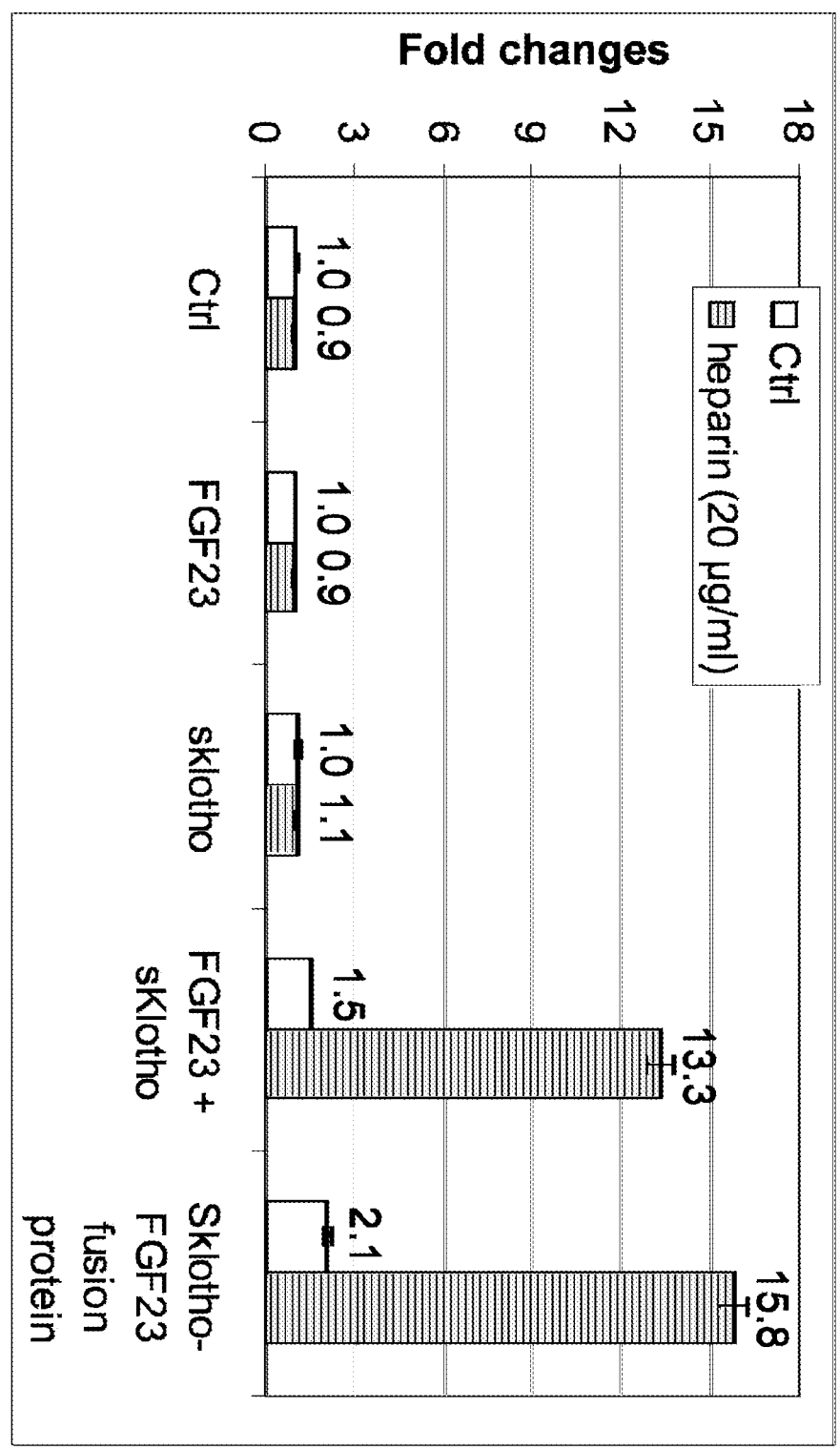

FIG. 3 illustrates the results of an Egr-1 luciferase assay comparing the activation level of Egr-1 in cells treated with conditioned media containing either a Klotho fusion polypeptide, a FGF23 polypeptide only, a soluble Klotho (sKlotho) polypeptide only, and a soluble Klotho polypeptide in combination with a FGF23 polypeptide in the absence or presence of heparin (20 μg/ml).

Figure 4A:
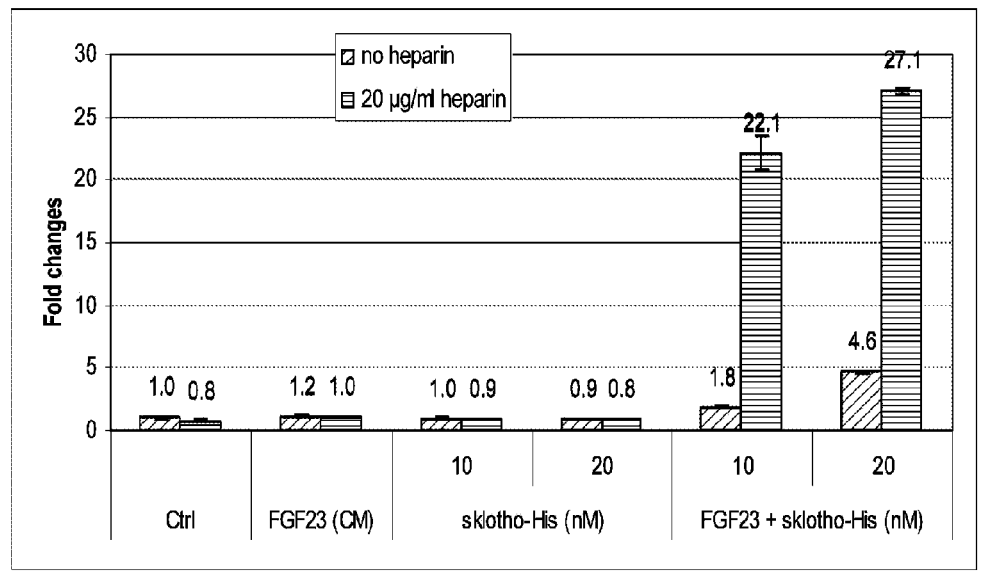
Figure 4B:
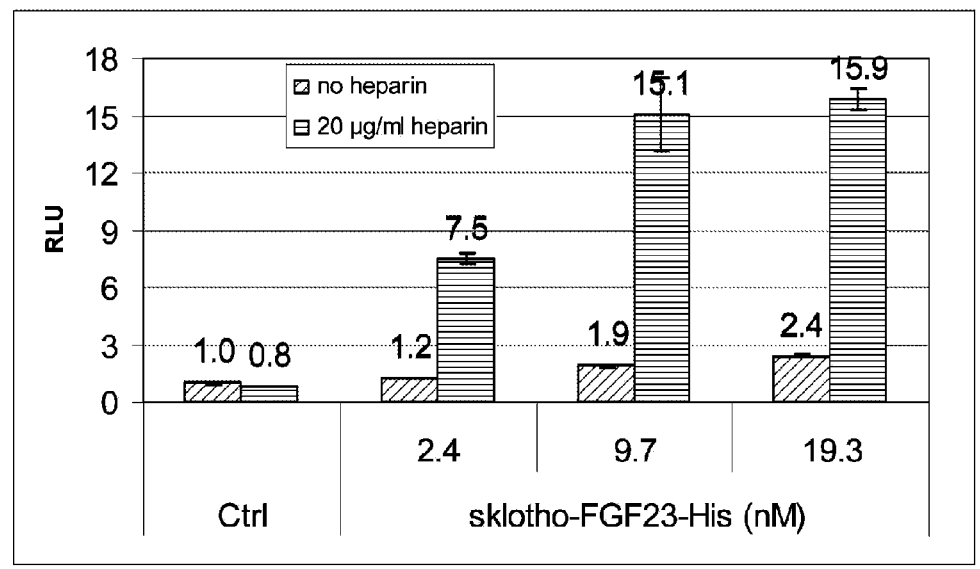

FIGS. 4A-4B depict the results of an Egr-1 luciferase assay comparing the activation level of Egr-1 in cells treated with purified Klotho fusion polypeptide, FGF23 polypeptide, or soluble Klotho polypeptide in the absence or presence of heparin. FIG. 4A shows a the results of an experiment comparing the activation level of Egr-1 in cells treated with FGF23 alone, sKlotho-His (10 nM or 20 nM) and a combination of FGF23 and sKlotho-His (10 nM or 20 nM) in the absence or presence of heparin (20 μg/ml). FIG. 4B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

Figure 5A:
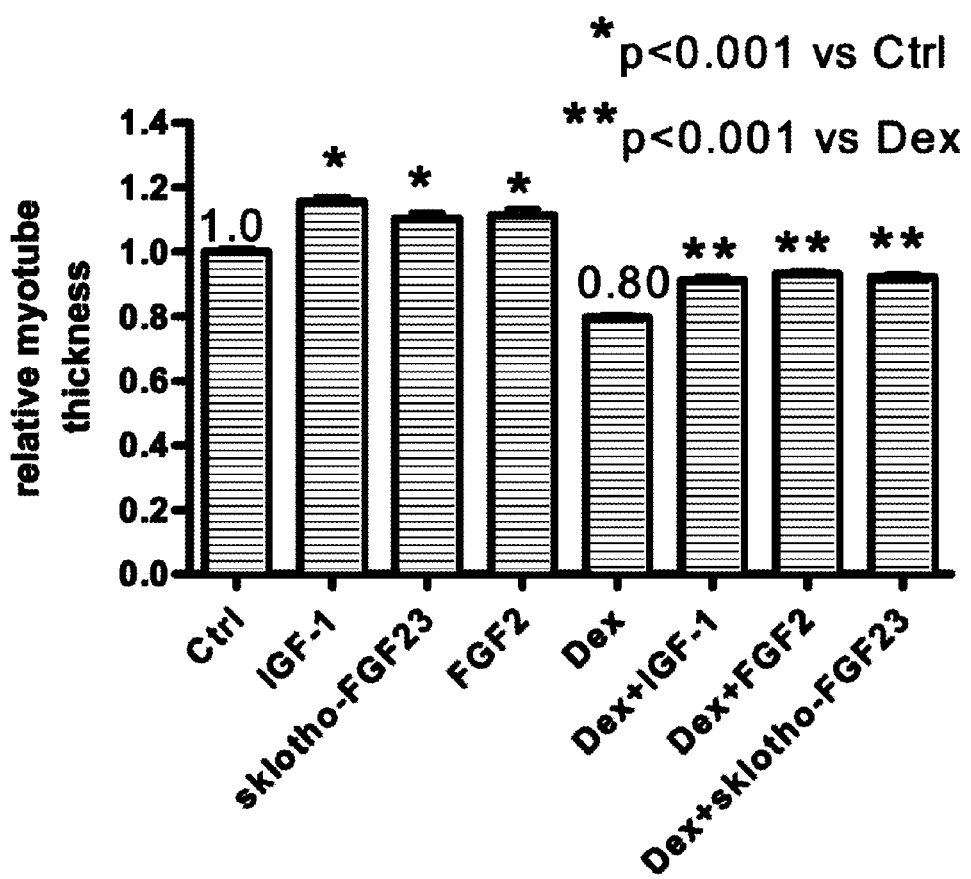
Figure 5B:
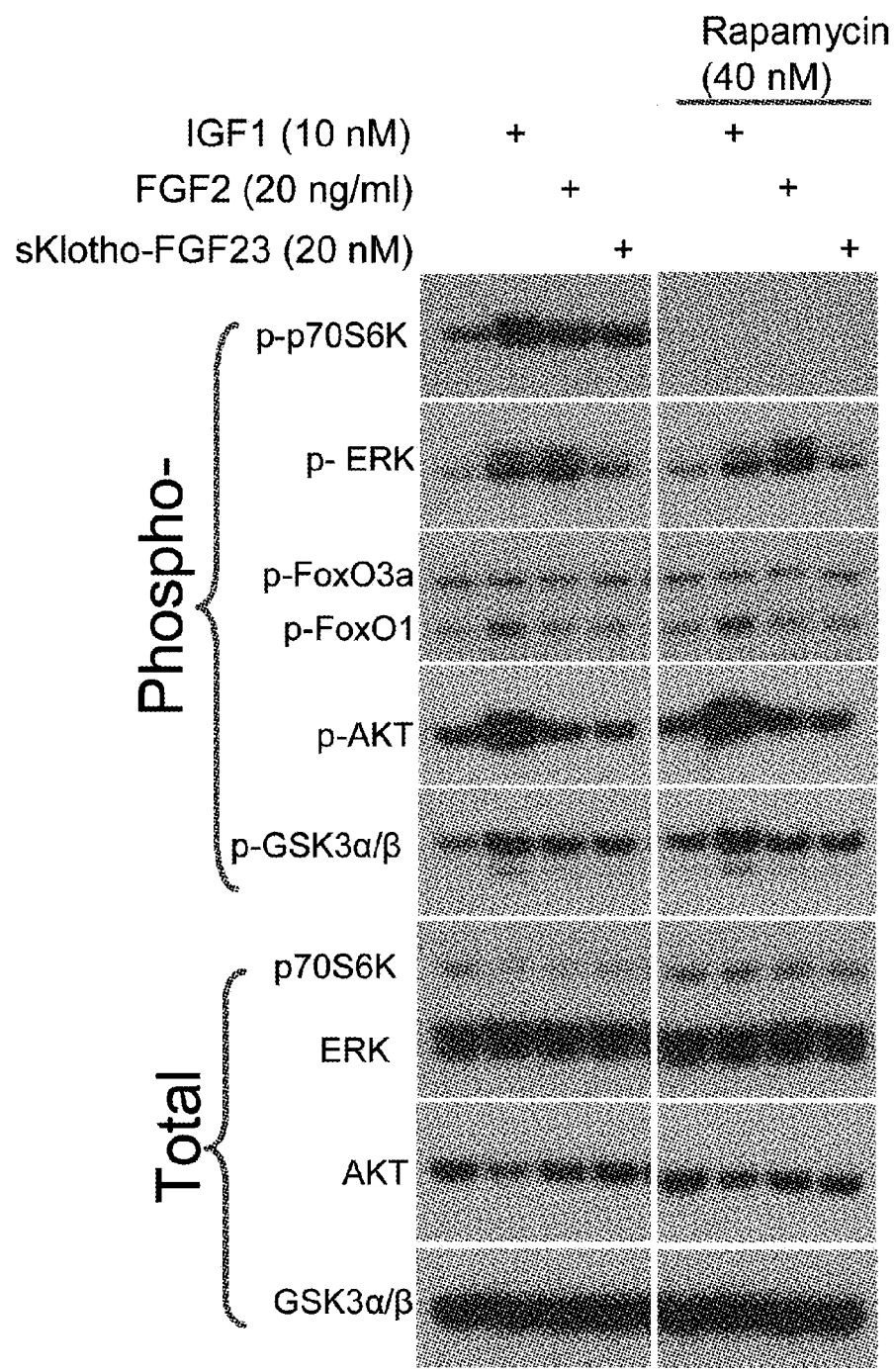

FIGS. 5A-5B illustrate the effect of treatment with a purified sKlotho fusion polypeptide on C2C12 muscle cells. FIG. 5A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 μM). FIG. 5B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

4. DETAILED DESCRIPTION

The present invention is directed to methods, kits and compositions for preventing or treating age-related conditions and metabolic disorders. The fusion polypeptides of the invention include a Klotho protein or active fragment thereof. In some embodiments, the fusion polypeptides of the invention include a Klotho protein or an active fragment thereof operatively linked to a fibroblast growth factor polypeptide or active fragment thereof. The Klotho fusion proteins or sKlotho of the present invention are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present invention, is based at least in part, on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be misoriented spatially if put together in a "cis" formation.

The Klotho-FGF fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Exemplary Klotho polypeptides suitable for use with the present invention include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP_783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP_526550), macaque (XP_001091413), horse (XP_001495248), dog (XP_536257), rat (XP_001078178), platypus (XP_001512722), and chicken (XP_423224). The Klotho polypeptides have an amino acid sequence that is substantially identical to the amino acid sequence of SEQ ID NO: 2 or SEQ ID NO:4; i.e., at least 70%, 75%, 80%, 85%, 90%, 95%, 96%, 97%, 98%, 99% or more identical at the amino acid sequences of SEQ ID NO:2 or SEQ ID NO:4, or active fragment thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment thereof.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase ½), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. No. 7,223,563 and U.S. Pat. No. 7,259,248, the contents of which are incorporated by reference in their entirety. Wild-type FGF has an amino acid sequence as is found in nature. Exemplary fibroblast growth factors suitable for use with the present invention include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO:33 or SEQ ID NO:35; i.e., having an amino acid sequence is which is at least 70%, 75%, 80%, 85%, 90%, 95%, 96%, 97%, 98%, 99% or more identical to the amino acid sequences of SEQ ID NO: 31 SEQ ID NO:33 or SEQ ID NO:35, or active fragments thereof.

The term "FGF", includes active fragments of the full-length polypeptide. Active FGF fragments that are able to bind to their corresponding FGF receptors are known in the art and also contemplated for use in the present invention. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Exemplary fibroblast growth factor receptors suitable for use with the present invention include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO:4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO:4) and are suitable for use with the present invention. Generally, a polypeptide that contains at least one Klotho subdomain is a Klotho active polypeptide. The Klotho extracellular subdomain for use with the polypeptide of the invention may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38.

"Signal peptide", as used herein, shall mean a peptide chain (3-60 amino acids long) that directs the post-translational transport of a protein to the endoplasmic reticulum and may be cleaved off. Exemplary signal peptides suitable for use with the present invention include the Klotho signal peptide (SEQ ID NO:19) and the IgG signal peptide (SEQ ID NO:20).

"Linker", as used herein, shall mean a functional group (e.g., chemical or polypeptide) that covalently attaches two or more polypeptides or nucleic acids so that they are connected with one another. As used herein, a "peptide linker" refers to one or more amino acids used to couple two proteins together (e.g., to couple the extracellular domain of Klotho and fibroblast growth factor-23). Peptide linkers suitable for use with the present invention include, but are not limited to, polypeptides with amino acid sequences represented by SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming noncovalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An exemplary variant of fibroblast growth factor-23 suitable for use with the present invention is the fibroblast growth factor-23 variant (R179Q).

"Pharmaceutical composition", as used herein, shall mean a composition containing a compound (e.g., a fusion polypeptide of the invention) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the invention, the administration of the polypeptides of the invention may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the invention, the administration of the polypeptides of the invention may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present invention.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present invention include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

An "effective dose" or "effective amount" is an amount sufficient to effect a beneficial or desired clinical result. In the context of the invention, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An exemplary human Klotho gene is provided at GenBank Accession No. NM_004795 (SEQ ID NO:1).

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present invention is directed to methods, kits and compositions for preventing or treating age-related conditions and metabolic disorders. The invention provides a fusion polypeptide having at least one extracellular subdomain of a Klotho protein. In some embodiments, the fusion polypeptides further comprise a fibroblast growth factor or an active fragment thereof. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment thereof can be used in practicing the invention.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the two extracellular subdomains can be two KL-D1 domains in tandem repeats, two KL-D2 domains in tandem repeats, or one KL-D1 domain and one KL-D2 domain.

The extracellular subdomain of a Klotho protein and the fibroblast growth factor (or an active fragment thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the invention may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO:4) and are suitable for use with the present invention. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the invention is soluble and is capable of binding to an FGF receptor.

The Klotho fusion polypeptides of the invention can contain a polypeptide linker which connects the polypeptide having at least one extracellular subdomain of a Klotho protein and the fibroblast growth factor. Suitable linkers are well known in the art and generally contain several Gly and several Ser residues, e.g., $(Gly_4 Ser)_3$ (SEQ ID NO:11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO: 12, SEQ ID NO: 13, SEQ ID NO:14, SEQ ID NO:15, SEQ ID NO:16, SEQ ID NO:17, or SEQ ID NO:18.

When a polypeptide linker is present in the Klotho fusion polypeptide of the invention, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker. A chemical linker can also be used to link the two polypeptides.

The Klotho fusion polypeptide of the invention may include a signal peptide. Exemplary signal peptides for use with the Klotho fusion polypeptide include, but are not limited to the Klotho signal peptide (SEQ ID NO: 8) and the IgG signal peptide (SEQ ID NO: 9).

4.1. Klotho and Fibroblast Growth Factor Polypeptides

The Klotho fusion polypeptides of the invention are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase ½) and activating Egr-1 (early growth response-1) gene. FGF is a secreted peptide growth factor that binds the FGF receptor. The amino acid and nucleic acid sequences of FGF are readily available to those of skill in the art. For example, exemplary nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Exemplary amino sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, exemplary nucleotide sequences for alpha-Klotho and beta-Klotho can be found in the GenBank database at Accession numbers: NM_004795 and NM_175737, respectively, and herein as SEQ ID NOs: 7 and 8, respectively. Exemplary amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the invention can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor-23 (SEQ ID NO: 35), or variants thereof (which include fibroblast growth factor-23 variant (R179Q) (SEQ ID NO: 36)).

Specifically, the Klotho fusion polypeptide of the invention may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the invention may have beta-Klotho (SEQ ID NO: 4), which is operatively coupled to fibroblast growth factor-19 (SEQ ID NO: 31). The Klotho fusion polypeptide of the invention may include a beta-Klotho (SEQ ID NO: 4), which is operatively coupled to fibroblast growth factor-21 (SEQ ID NO: 33).

The invention includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but, rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present invention further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the invention described herein have an amino acid sequence which is at least about 60%, 70%, 80%, 90%, 95%, 96%, 97%, 98%, 99% or more identical or homologous to an amino acid sequence described herein.

The nucleic acid sequences of molecules of the invention described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the invention may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. *Current Protocols in Molecular Biology*, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF Fusion Polypeptides of the Invention

In some embodiments of the invention, a Klotho fusion polypeptide has a polypeptide chain having a first polypeptide sequence of a Klotho polypeptide or an active fragment thereof and a second polypeptide sequence encoding FGF or an active fragment thereof.

The invention includes fusion polypeptides which are at least about 95% or more homologous to an amino acid sequence presented in SEQ ID NO:19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains.

The Klotho fusion polypeptide of the invention may include an amino acid sequence which is at least about 95% identical to the amino acid sequence set forth in SEQ ID NO:7. The amino acid sequence of SEQ ID NO: 7 encodes a Klotho extracellular domain lacking a signal peptide.

The subject fusion proteins are described herein and can be made using methods known in the art. For example, the fusion polypeptides of the invention may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. The nucleic acid encoding the Klotho-FGF fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present invention, a nucleic acid molecule encoding an extracellular subdomain of Klotho will be fused in frame to the nucleic acid molecule encoding FGF. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the invention have at least two polypeptides that are covalently linked, in which one polypeptide comes from one protein sequence or domain, e.g., Klotho, and the other polypeptide comes from another protein sequence or domain, e.g., FGF. Klotho and FGF, of the fusion polypeptides of the invention, can be joined by methods well known to those of skill in the art. These methods include both chemical and recombinant means.

Nucleic acids encoding the domains to be incorporated into the fusion polypeptides of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the invention, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the invention described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO:3, SEQ ID NO: 30, SEQ ID NO: 32, or SEQ ID NO: 34.

Nucleic acid sequences that encode Klotho and FGF peptides can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present invention, Klotho and FGF can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the invention. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present invention, the amino acid sequence of an extracellular subdomain of Klotho or a fragment thereof may be linked to the FGF via a peptide linker. Exemplary peptide linkers are well known in the art and described herein. For example, peptide linkers generally include several Gly and several Ser residues, such as: ($Gly_4$ $Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). Specifically, a peptide linker for use in a fusion protein of the invention may act as a flexible hinge.

The signal sequence of Klotho or FGF may be excluded prior to incorporation of Klotho into a fusion protein of the invention. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the invention will contain the mature form of Klotho and FGF.

Generally, introns are excluded from either one or both the Klotho or the FGF moieties prior to incorporation into a fusion polypeptide.

The fusion polypeptides of the invention may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the invention is expected to provide such improved properties as increased half-life, solubility, and protease resistance. The fusion polypeptides of the invention may alternatively be modified by the covalent addition of polymers to free amino groups such as the lysine epsilon or the N-terminal amino group. Preferred cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The invention is also directed to the expression of a fusion polypeptide that is at least about 95% or more homologous to an amino acid sequence presented in SEQ ID NO:19-28.

4.3. Expression of Fusion Polypeptides of the Invention

In order to express the fusion protein of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast ga14 gene promoter, etc. Transcriptional initiation regulatory signals may be selected which allow for repression or activation, so that expression of the genes can be modulated.

In some of the molecules of the invention described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the invention. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the fusion polypeptides of the invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the invention. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radioactive label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5 Pharmaceutical Compositions and Methods of Treatment

The invention also pertains to pharmaceutical compositions containing one or more fusion polypeptides of the invention and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition to the patient.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the invention may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the invention can be formulated so as to allow a polypeptide of the invention to be bioavailable upon administration of the composition to a subject. Compositions can take the form of one or more dosage units, where, for example, a tablet can be a single dosage unit, and a container of a polypeptide of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the invention and pharmaceutically acceptable carriers are sterile. Water is a preferred carrier when the polypeptide of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions contain an effective amount of a compound of the invention (e.g., fusion polypeptide) such that a suitable dosage will be obtained. The pharmaceutical compositions may contain the known effective amount of the compounds as currently prescribed for their respective disorders.

The route of administration of the polypeptide of the invention used in the prophylactic and/or therapeutic regimens which will be effective in the prevention, treatment, and/or management of a age-related condition or metabolic disorder can be based on the currently prescribed routes of administration for other therapeutics known in the art. The polypeptides of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the invention. More than one polypeptides of the invention may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the invention may be administered parenterally. Specifically, the polypeptides of the invention may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the invention can also be formulated as a suppository, with traditional binders and carriers such as triglycerides.

The polypeptides of the invention can be delivered in a controlled release system. For example, a pump can be used (see Sefton, *CRC Crit. Ref. Biomed. Eng.* 1987, 14, 201; Buchwald et al., Surgery 1980, 88: 507; Saudek et al., *N. Engl. J. Med.* 1989, 321: 574). Polymeric materials can also be used for controlled release of the polypeptides of the invention (see *Medical Applications of Controlled Release*, Langer and Wise (eds.), CRC Pres., Boca Raton, Fla., 1974;

*Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.,* 1989, 25, 3511; Howard et al., *J. Neurosurg.,* 1989, 71, 105). Specifically, a controlled-release system can be placed in proximity of the target of the polypeptides of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (Science 1990, 249, 1527-1533) can be used.

Polymeric materials used to achieve controlled or sustained release of the polypeptides of the invention are disclosed, e.g., in U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the invention, wherein the dose of an effective amount achieves a plasma level of at least 0.01 µg mL to at least 400 µg/mL of the polypeptide of the invention.

A prophylactic and/or therapeutic regimen may involve administering to a patient a plurality of doses of an effective amount of a polypeptide of the invention, wherein the plurality of doses maintains a plasma level of at least 0.01 µg/mL, to 400 µg/mL of the polypeptide of the invention. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the invention in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics,* 10*th ed*., Mc-Graw-Hill, New York, 2001; *Physician's Desk Reference* (60*th* ed., 2006), which is incorporated herein by reference in its entirety.

The invention includes methods of treating disorders wherein agonistic activity of Klotho protein and FGF are desirable. Examples of such methods of the invention include, but are not limited to age-related condition or metabolic disorders.

The invention includes methods for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat or prevent the age-related condition. In some embodiments, the Klotho fusion polypeptide is coadministered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The invention is also directed to a method for treating or preventing a metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder. In some embodiments, the Klotho fusion polypeptide is coadministered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The invention also provides methods for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat hyperphosphatemia or calcinosis. In some embodiments, the Klotho fusion polypeptide is coadministered with a pharmacologically effective dose of heparin. In a particular embodiment, a Klotho fusion protein containing at least one extracellular domain of an alpha Klotho protein and fibroblast growth factor 23 is administered to an individual in need of treatment for a hyperphosphatemia or calcinosis.

The invention is also directed to a method for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat chronic renal disease or chronic renal failure. In some embodiments, the Klotho fusion polypeptide is coadministered with a pharmacologically effective dose of heparin. In some embodiments, a Klotho fusion protein containing at least one extracellular domain of an alpha Klotho protein is administered to an individual in need of treatment for chronic renal disease or chronic renal failure.

The invention also includes methods for treating or preventing cancer in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat cancer. The method may be used in the treatment or prevention of breast cancer. In some embodiments, the Klotho fusion polypeptide is coadministered with a pharmacologically effective dose of heparin. In some embodiments, a Klotho fusion protein containing at least one extracellular domain of an alpha Klotho protein is administered to an individual in need of treatment for cancer.

In methods of treating disorders by administering a pharmaceutical composition containing a Klotho fusion polypeptide, the Klotho fusion polypeptide has at least one extracellular subdomain of a Klotho protein and a fibroblast growth factor. In a particular embodiment, the Klotho fusion protein contains at least one extracellular domain of a beta Klotho protein and fibroblast growth factor 21.

The Klotho fusion polypeptide composition can be administered according to any method of administration known to those of skill in the art and described herein. Preferred methods of administration include subcutaneous or intravenous. Other effective modes of administration are described herein.

4.6. Methods of Treatment and Assays for Assessing Efficacy

Methods of the invention which provide administering the Klotho fusion polypeptide to an individual can be used to treat a variety of disorders including an age-related disorder or a metabolic disorder. Without being limited by any particular theory, Klotho/FGF fusion polypeptides may be used to treat disorders in which there is dysregulation of Klotho or FGF. Exemplary disorders include metabolic disorders and age-related disorders. For example, both FGF23 or Klotho knockout mice display a variety of similar phenotypes including, low physical activity, growth retardation, muscle wasting, skin atrophy, atherosclerosis, short life spans, etc. (See Razzaque and Lanske, *J. of Endrocrinology*, 194:1-10 (2007), which is herein incorporated by reference).

In particular, Klotho/FGF23 fusion polypeptides of the invention are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, Klotho/FGF19 fusion polypeptides and Klotho/FGF21 fusion polypeptides of the invention may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and carciovascular diseases.

Based at least in part on the finding that FGF23 is able to stimulate excretion of phosphate in the urine and thereby reduce phosphate levels in the serum, Klotho-FGF23 fusion polypeptides of the invention can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117:2684-2691 (2007), which is herein incorporated by reference). An individual is administered a pharmacologically effective dose of a pharmaceutical composition containing the Klotho fusion polypeptide, having at least one extracellular subdomain of a Klotho protein and a fibroblast growth factor so as to treat or prevent hyperphosphatemia or calcinosis. In particular, a Klotho fusion polypeptide containing at least one extracellular domain of an alpha Klotho protein and a fibroblast growth factor is useful for treating hyperphosphatemia or calcinosis.

Klotho fusion polypeptides of the invention can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280: 1015-1020 (2001), which is herein incorporated by reference). An individual is administered a pharmacologically effective dose of a pharmaceutical composition containing the Klotho fusion polypeptide, having at least one extracellular subdomain of a Klotho protein and a fibroblast growth factor so as to treat or prevent chronic renal disease or chronic renal failure. In particular, a Klotho fusion polypeptide containing at least one extracellular domain of an alpha Klotho protein is useful for treating chronic renal disease or chronic renal failure.

Klotho fusion polypeptides of the invention can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein and a fibroblast growth factor so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the invention on an age-related disorder or metabolic disorder include organismal based assays, e.g., using a mammal (e.g., a mouse, rat, primate, or some other non-human), or other animal (e.g., *Xenopus*, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the invention may be evaluated using an animal that has a particular disorder, e.g., a disorder described herein, e.g., an age-related disorder, a metabolic disorder. These disorders can also provide a sensitized system in which the test polypeptide's effects on physiology can be observed. Exemplary disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the invention, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the invention for treating an age-related disorder, an animal having decreased Klotho expression may be used, e.g., mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Exemplary metabolic parameters include: glucose concentration, insulin concentration, and insulin sensitivity.

Another exemplary system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Exemplary age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (exemplary parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode *C. elegans*, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein).

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe exemplary markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, J Biol Chem 244, 3223-9 (1969).)

Exemplary animal models for AMD include: laser-induced mouse model simulating exudative (wet) macular degeneration Bora et al., Proc. Natl. Acad. Sci. USA., 100:2679-84 (2003); a transgenic mouse expressing a mutated form of cathepsin D resulting in features associated with the "geographic atrophy" form of AMD (Rakoczy et al., Am. J. Pathol., 161:1515-24 (2002)); and a transgenic mouse over expressing VEGF in the retinal pigment epithelium resulting in CNV. Schwesinger et al., Am. J. Pathol. 158:1161-72 (2001).

Exemplary animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem. 86:165-72 (2003) and Link, Mech. Ageing Dev., 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (U.S. Pat. No. 5,420,112) or rabbits (Ogawa et al., Neurotoxicology, 21:501-11 (2000)); a streptozotocin (STZ)-diabetic rat for study of autonomic neuropathy (Schmidt et al., Am. J. Pathol., 163:21-8 (2003)); and a progressive motor neuropathy (pmn) mouse (Martin et al., Genomics, 75:9-16 (2001)).

Exemplary animal models of hyperphosphatemia or tumoral calcinosis include Klotho knockout mice and FGF23 knockout mice (Yoshida et al., Endocrinology 143:683-689 (2002)).

Exemplary animal models of chronic renal disease or chronic renal failure include COL4A3+/−mice (Beirowski et al., J. Am. Soc. Nephrol. 17:1986-1994 (2006)).

Exemplary animal models of cancer include the transplantation or implantation of cancer cells or tissue into nude mice, as is known in the art (Giovanella et al., Adv. Cancer Res. 44:69-120 (1985)). For example, animal models of breast cancer include nude mice transplanted or implanted with breast cancer cells or tissue (e.g., Yue et al., Cancer Res. 54:5092-5095 (1994); Glinsky et al., Cancer Res. 56:5319-5324 (1996); Visonneau Am. J. Path. 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods of the invention which provide administering the Klotho fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., J. Biol. Chem., 265:8550-8557, 1990). The breakdown of these proteins can be followed, e.g., by measuring 3-methyl-histidine production, which is a specific constituent of actin, and in certain muscles of myosin (Goodman, Biochem. J. 241: 121-12, 1987 and Lowell, et al., Metabolism, 35:1121-112, 1986; Stein and Schluter, Am. J. Physiol. Endocrinol. Metab. 272: E688-E696, 1997). Release of creatine kinase (a cell damage marker) (Jackson, et al., Neurology, 41: 101104, 1991) can also be indicative.

Non-Insulin-Dependent Diabetes

Methods of the invention which provide administering the Klotho fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. No. 5,266,561 and U.S. Pat. No. 6,518, 069). For example, glucose-stimulated insulin levels typically fail to rise above 4.0 nmol/L. (U.S. Pat. No. 5,266,561). Exemplary symptoms of Type II diabetes include: hyperglycemia while fasting (U.S. Pat. No. 5,266,561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods of the invention which provide administering the Klotho fusion polypeptide to an individual can be used to treat Alzheimer's Disease (AD). Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42), which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5): 400-410 (2003). For example, p-amyloid induces caspase-2-dependent apoptosis in cultured neurons (Troy et al. *J, Neurosci.* 20(4): 1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14): 1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tan protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3r Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.* 270, 103-111; Ge, H. (2000). Nucleic Acids Res. 28, e3, I-VII; MacBeath, G., and Schreiber, S. L. (2000). *Science* 289, 1760 to 1 763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6,187,992.

Parkinson's Disease

Methods of the invention which provide administering the Klotho fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.,* 3:932-42 (2002)). Exemplary motor symptoms include: akinesia, stooped posture, gait difficulty, postural instability, catalepsy, muscle rigidity, and tremor. Exemplary non-motor symptoms include: depression, lack of motivation, passivity, dementia and gastrointestinal dysfunction (see, e.g., Fahn, *Ann. N.Y. Acad. Sci.*, 991:1-14 (2003) and Pfeiffer, *Lancet Neurol.*, 2:107-16 (2003)) Parkinson's has been observed in 0.5 to 1 percent of persons 65 to 69 years of age and 1 to 3 percent among persons 80 years of age and older. (see, e.g., Nussbaum et al., *N. Engl. J. Med.*, 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, *Ann. N.Y. Acad. Sci.*, 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:I3 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods of the invention which provide administering the Klotho fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol Genet.* 6(10): 1633-7 (1997); Hansson et al. *J. of Neurochemistry* 78: 694-703; and Rubinsztein, D. C., *Trends in Genetics*, Vol. 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci. USA* 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

Exemplary motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Cancer

Methods of the invention which provide administering the Klotho fusion polypeptide to an individual can be used to treat cancer. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyclocytic leukemia, acute myclomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

All patents, patent applications, and published references cited herein are hereby incorporated by reference in their entirety. While this invention has been particularly shown and described with references to embodiments thereof, it will be understood by those skilled in the art that various changes in form and details may be made therein without departing from the scope of the invention encompassed by the appended claims.

5. EXAMPLES

Example 1

Expression and Purification of Klotho Fusion Polypeptides

Expression of the Klotho Fusion Polypeptide

The polypeptides of the invention were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23 (R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 2A) or stained with Coomassie blue (FIG. 2B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 2B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 2A). An anti-FGF23 rat monoclonal IgG2A (R&D Systems, Cat# MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23 (R179Q) fusion protein.

Purification of the Klotho Fusion Polypeptide

The polypeptides of the invention were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6×His was transfected (500 µg DNA in 18 ml of OptiMEM 1 (GIBCO, Cat #11058) mixed with 18 ml of 2 µg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6×His bound tightly to the column and was eluted with 50 mM imidazole. The resulting purified material was then dialyzed in PBS to remove imidazole. A sample of the purified sKlotho-FGF23-6×His was separated by SDS-PAGE (lane 1, purified sKlotho-FGF23-6×His; lane 2, molecular weight marker) and analyzed by staining with Coomassie blue (FIG. 2C). The stained SDS-PAGE gel confirmed that the purified sKlotho-FGF23-6×His had the expected molecular weight. The inability to detect bands corresponding to proteins other than full-length sKlotho-FGF23-6×His in the lane loaded with the purified material also showed that the sKlotho-FGF23-6×His was purified.

Example 2

In Vitro Assay Assessing the Activity of the Klotho Fusion Polypeptide

Egr-1-Luciferase

The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene together with a transfection normalization reporter gene (*Renilla* luciferase). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho-FGF23 (R179Q) fusion protein) and 50% DMEM with 1% FBS in the presence or absence of 20 µg/ml heparin (Sigma, Cat#H8537; dissolved in DMEM as 2 mg/ml stock) were tested in the Egr-1-luciferase reporter assays (FIG. 3). Further experiments used defined quantities of the purified polypeptides (FIGS. 4A and 4B). Cells were lysed 20 hours later in passive lysis buffer (Promega, Cat #E194A) and luciferase activities were determined using Dual-Glo Luciferase Assay System (Promega, Cat #E2940).

In initial experiments, Klotho fusion polypeptide activity was demonstrated in unfractionated conditioned medium. Using the Egr-1-luciferase reporter gene (FIG. 3) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23 (R179Q) activated the Egr-1-luciferase reporter gene in contrast to conditioned media containing either FGF23 or Klotho alone. In these experiments, conditioned medium containing the fusion protein sKlotho-FGF23 (R179Q) activated the Egr-1-luciferase reporter gene significantly better than conditioned medium containing a combination of FGF23 and Klotho. In the presence of heparin, the inductions by conditioned medium containing the fusion protein sKlotho-FGF23 (R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

|   | sKlotho-FGF23 fusion constructs | Expression | Activity in Egr-1-luc reporter gene |
|---|---|---|---|
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692-965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 5A). The luciferase reporter activity from the combination of purified FGF23 and sKlotho was further dependent on the dose of purified sKlotho, and the effect could be enhanced by the presence of heparin (20 µg ml). An effect of the sKlotho-FGF23-6×His fusion polypeptide on luciferase activity could be detected at concentrations as low as about 1.21 nM (1.2 fold change) and at least up to about 19.3 nM (2.4 fold change) in Egr-1-luciferase reporter assays (FIG. 5B). The activity of the sKlotho-FGF23-6×His fusion polypeptide on luciferase activity was significantly enhanced in the presence of heparin (20 µg ml). In the presence of heparin, the effect of the sKlotho-FGF23-6×His fusion polypeptide on luciferase activity could be detected at a concentration as low as about 0.6 nM (2.0 fold change). The result showed that purified sKlotho-FGF23-6×His dose-dependently induced the EGR-1-luc reporter gene, and that treatment with sKlotho-FGF23-6×His.

Example 3

In Vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg ml), transferrin (5.5 mg ml), and selenium (5 ng ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng ml) or sKlotho-FGF23 (20 nM) in the absence or presence of dexamethasone (100 µM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 4A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 4B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

What is claimed is:

1. A fusion polypeptide comprising the sequence of amino acids 34 to 1228 of SEQ ID NO: 19.

2. The fusion polypeptide of claim 1, further comprising a signal peptide.

3. The fusion polypeptide of claim 2, wherein the signal peptide is the Klotho signal peptide.

4. The fusion polypeptide of claim 2, wherein the signal peptide is the IgG signal peptide.

5. A pharmaceutical composition comprising the fusion polypeptide of claim 1 and a pharmaceutically acceptable carrier.

6. A fusion polypeptide, wherein the sequence of the fusion polypeptide comprises the amino acid sequence of SEQ ID NO: 19.

7. A fusion polypeptide, wherein the sequence of the fusion polypeptide consists of the amino acid sequence of SEQ ID NO: 19.

8. A fusion polypeptide, wherein the sequence of the fusion polypeptide comprises the amino acid sequence of SEQ ID NO: 20.

9. A fusion polypeptide, wherein the sequence of the fusion polypeptide consists of the amino acid sequence of SEQ ID NO: 20.

10. A nucleic acid comprising a sequence that encodes a fusion polypeptide comprising the sequence of amino acids 34 to 1228 of SEQ ID NO: 19.

11. A host cell containing the nucleic acid of claim 10.

12. A vector comprising the nucleic acid of claim 10.

13. A method for activating Egr-1 in an individual, comprising the step of: administering to an individual a fusion polypeptide comprising the sequence of amino acids 34 to 1228 of SEQ ID NO: 19.

14. The method of claim 13, wherein the individual is in need of a treatment for an age-related condition selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

15. The method of claim 13, wherein the individual is in need of a treatment for muscle wasting.

16. The method of claim 13, wherein the individual is in need of a treatment for a metabolic disorder selected from the group consisting of Type II Diabetes, Metabolic Syndrome, hyperglycemia, and obesity.

17. The method of claim 13, wherein the individual is in need of a treatment for hyperphosphatemia or calcinosis.

18. The method of claim 13, wherein the individual is in need of a treatment for chronic renal disease or chronic renal failure.

19. The method of claim 13, wherein the individual is in need of a treatment for cancer.

20. The method of claim 19, wherein the cancer is breast cancer.

21. A method for activating Egr-1 in an individual, comprising the step of: administering to an individual a fusion polypeptide comprising the sequence of SEQ ID NO: 19 or 20.

* * * * *